US007422883B2

(12) United States Patent
Agrez et al.

(10) Patent No.: US 7,422,883 B2
(45) Date of Patent: Sep. 9, 2008

(54) MAP KINASE INTEGRIN-BINDING DOMAIN

(75) Inventors: Michael Valentine Agrez, Merewether (AU); Nuzhat Ahmed, Yallambie (AU)

(73) Assignee: Inter-K Pty Limited, Newcastle, NSW (AU)

( * ) Notice: Subject to any disclaimer, the term of this patent is extended or adjusted under 35 U.S.C. 154(b) by 279 days.

(21) Appl. No.: 10/451,291

(22) PCT Filed: Dec. 21, 2001

(86) PCT No.: PCT/AU01/01672

§ 371 (c)(1), (2), (4) Date: Apr. 16, 2004

(87) PCT Pub. No.: WO02/051993

PCT Pub. Date: Jul. 4, 2002

(65) Prior Publication Data

US 2005/0214755 A1 Sep. 29, 2005

(30) Foreign Application Priority Data

Dec. 22, 2000 (AU) .................................... PR2305

(51) Int. Cl.
*C12N 9/12* (2006.01)
*C07K 14/00* (2006.01)

(52) U.S. Cl. ...................................... 435/194; 530/324

(58) Field of Classification Search ................. 530/350, 530/324; 435/194
See application file for complete search history.

(56) References Cited

U.S. PATENT DOCUMENTS

| | | | | |
|---|---|---|---|---|
| 5,593,884 | A | 1/1997 | Karin et al. | 435/252.3 |
| 5,807,746 | A | 9/1998 | Lin et al. | |
| 5,962,643 | A | 10/1999 | Sheppard et al. | |
| 6,007,991 | A | 12/1999 | Sivaraman et al. | 435/6 |
| 6,043,339 | A | 3/2000 | Lin et al. | |
| 6,248,558 | B1 | 6/2001 | Lin et al. | |
| 6,312,956 | B1 | 11/2001 | Lane | |
| 6,339,148 | B1 | 1/2002 | Sheppard et al. | |
| 6,432,680 | B1 | 8/2002 | Lin et al. | |
| 6,495,518 | B1 | 12/2002 | Hawiger et al. | |
| 6,576,432 | B1 | 6/2003 | Sheppard et al. | |
| 6,596,277 | B1 | 7/2003 | Sheppard et al. | |
| 6,639,056 | B2 | 10/2003 | Sheppard et al. | |
| 6,692,741 | B2 | 2/2004 | Huang et al. | |
| 6,780,843 | B2 | 8/2004 | Lin et al. | |
| 6,787,322 | B2 | 9/2004 | Sheppard et al. | |

FOREIGN PATENT DOCUMENTS

| | | |
|---|---|---|
| WO | WO 91/19008 | 12/1991 |
| WO | WO 92/12236 | 7/1992 |
| WO | WO 95/34295 | 12/1995 |
| WO | WO 98/16241 | 4/1998 |
| WO | WO 98/16241 A1 | 4/1998 |
| WO | WO 99/09214 | 2/1999 |
| WO | WO 99/49879 | 10/1999 |
| WO | WO 00/59549 | 10/2000 |
| WO | WO 01/00677 | 1/2001 |
| WO | WO 01/37821 A1 | 5/2001 |
| WO | WO 01/97827 | 12/2001 |

OTHER PUBLICATIONS

Meloche, S., et al. 1992 Molecular Biology of the Cell 3: 63-71.*
Liu, S. et al., "Binding of paxillin to $\alpha_4$ integrins modifies integrin-dependent biological responses," Nature, vol. 402, pp. 676-681 (Dec. 9, 1999).
Liu, X. et al., "Identified of a functionally important sequence in the cytoplasmic tail of integrin $\beta_3$ by using cell-permeable peptide analogs," Proc. Natl Acad. USA, vol. 93, pp. 11819-11824 (Oct. 1996).
Mainiero, F. et al., "The coupling of $\alpha_6\beta_4$ integrin to Ras-MAP kinase pathways mediated by She controls keratinocyte proliferation," The EMBO Journal, Oxford University Press, vol. 16, No. 9, pp. 2365-2375 (1997).
Sebolt-Leopold, J. et al., "Blockade of the Map kinase pathway suppresses growth of colon tumors in vivo," Nature Medicine, vol. 5, No. 7, pp. 810-816 (Jul. 1999).
Gu et al (Journal of Cell biology, 1998, vol. 143, pp. 1375-1383).
Pillinger et al (PNAS, 1998, vol. 95, pp. 14540-14545).
Agrez, M.V. et al., "The αvβ6 integrin induces gelatinase B secretion in colon cancer cells," Int. J. Cancer: 81, 90-97 (1999).
Agrez, M., et al., "The αvβ6 integrin promotes proliferation of colon carcinoma cells through a unique region of the β6 cytoplasmic domain," J. Cell Biol.127, No. 2, pp. 547-556 (Oct. 1994).
Ahmed, N. et al., "Direct integrin αvβ6-ERK binding: implications for tumour growth," Oncogene 21, pp. 1370-1380 (Feb. 21, 2002).
Dedhar, S. et al., "Integrin cytoplasmic interactions and bidirectional transmembrane signalling," Current Opnion in Cell Biology, Current Science, London, vol. 8, No. 5, pp. 657-669 (Oct. 1, 1996).
Erker, J.C. et al., Database Genbank 'Online!, "polyprotein GB virus c/Hepatitis C virus," Database accession No. AAC55951 (Nov. 13, 1996).
Fodstad, O. et al., Database Geneseq 'Online!, "CAPL gene 5' splice site antisense oligonucleotide," Database accession No. AAT33333 (Nov. 12, 1996).
Hughes, P.E. et al., "Integrin affinity modulation," Trends in Cell Biology, England, vol. 8, No. 9, pp. 359-364 (Sep. 1998).
Kerr, J.S. et al., "Novel small molecule αv integrin antagonists: comparative anti-cancer efficacy with known angiogenesis inhibitors," Anticancer Research 19: 959-968 (1999).
Lub, M. et al., "Cytoplasmic tails of $\beta_1$, $\beta_2$, and $\beta_7$ integrins differentially regulate LFA-1 function in K562 cells," Molecular Biology of the Cell, vol. 8, No. 4, pp. 719-728 (Apr. 1997).

(Continued)

*Primary Examiner*—Maryam Monshipouri
*Assistant Examiner*—Marsha Tsay
(74) *Attorney, Agent, or Firm*—Weingarten, Schurgin, Gagnebin & Lebovici LLP

(57) ABSTRACT

Dislosed is the integrin-binding domain of MAP kinase. Interaction between MAP kinase and integrin via this domain activates MAP kinase and initiates cellular activity. Methods of modulating cellular activity by inhibiting direct MAP kinase-integrin binding are provided. These methods have particular use in inhibiting growth of cancer cells.

8 Claims, 41 Drawing Sheets

OTHER PUBLICATIONS

Figure 1:
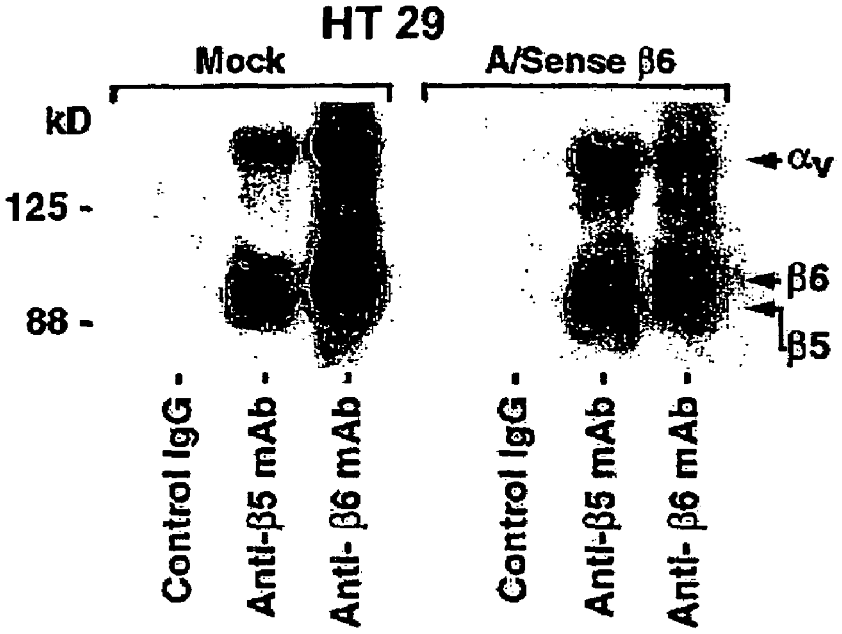

Marcantonio, E.E. et al., "Mapping of the functional determinants of the integrin $\beta_1$ cytoplasmic domain by site-directed mutagenesis," Cell Regulation, vol. 1, No. 8, pp. 597-604 (Jul. 1990).
Mastrangelo, A.M. et al., "Amino acid motifs required for isolated β cytoplasmic domains to regulate 'in trans' β1 integrin conformation and function in cell attachment,"J. Cell Science, vol. 112, No. 2, pp. 217-229 (Jan. 1999).
Meurers, B.H. et al., Database Genbank 'Online! "Myosin heavy chain 12 *Homo sapiens*!", Database accession No. CAA69036 (Jan. 8, 1997).
Niu, J. et al., "Integrin expression in colon cancer cells is regulated by the cytoplasmic domain of the β6 integrin subunit," Int. J. Cancer, vol. 99, No. 4, pp. 529-537 (Jun. 1, 2002).
Oda, K. et al., Database Genbank 'Online! "CoxII intron2 ORF *Marchantiapolymorpha*!", Database accession No. AAC09431 (Apr. 2, 1998).
O'Toole, T.E. et al., "Regulation of integrin affinity states through an NPXY motif in the β subunit cytoplasmic domain,"J. Biol. Chem. 270, No. 15, pp. 8553-8558 (Apr. 14, 1995).
Pardi, R. et al., "Conserved regions in the cytoplasmic domains of the leukocyte integrin $\alpha_L\beta_2$ are involved in endoplasmic reticulum retention, dimerization, and cytoskeletal association," Journal of Immunology, vol. 155, No. 3, pp. 1252-1263 (Aug. 1, 1995).
Patil, S. et al, "A double mutation of the NPLY motif in the integrin $\beta_3$ cytoplasmic tail abolishes post-ligand binding events of $\beta_3$ integrins," Molecular Biol. of the Cell, vol. 7, no. Suppl., p. 248A (Annual Mtg. of the 6th International Congress on Cell Biology and the 36th American Society for C; San Francisco, California, US, Dec. 7-11, 1996).
Roberts, M.S. et al., "ERK1 associates with $\alpha_v\beta_3$ integrin and regulates cell spreading on vitronectin," J. Biol. Chem., vol. 278, No. 3, pp. 1975-1985 (Jan. 17, 2003).
Swanson, R. et al., Database Genbank 'Online!, "UL97 honolog 'Rhesus cytomegalovirus!", Database accession No. AAC05259 (Mar. 7, 1998).
Tada, M. et al., Database Genbank 'Online!, "homeobox protein BIX3 *'Xenopus laevis*!", Database accession No. AAC61703 (Sep. 29, 1998).
Tahiliani, P.D. et al., "The role of conserved amino acid motifs within the integrin $\beta_3$ cytoplasmic domain in triggering focal adhesion kinase phosphorylation,"J. Biol. Chem., vol. 272, No. 12, pp. 7892-7898 (Mar. 21, 1997).
Townsend, P.A. et al., "β1 integrin antisense oligodeoxynucleotides: utility in controlling osteoclast function," Eur. J.Cell Biol., vol. 78, pp. 485-496 (Jul. 1999).
Trikha, M. et al., "Role of $\alpha IIb\beta_3$ integrin in prostate cancer metastasis," The Prostate, vol. 35, pp. 185-192 (1998).
Vignoud, L. et al., "NPXY motifs control the recruitment of the α5β1 integrin in focal adhesions independently of the association of talin with the β1 chain," J. Cell Science, vo. 110, pp. 1421-1430 (Jun. 1997).
Weinacker, A. et al., Role of the integrin $\alpha_v\beta_6$ in cell attachment to fibronectin, J. Biol. Chem., vol. 269, No. 9, pp. 6940-6948 (Mar. 4, 1994).
Zage, P.E. et al., "The membrane proximal region of the integrin β cytoplasmic domain can mediate oligomerization," Cell Adhesion and Communication, vol. 5, No. 5, pp. 335-347 (1998).
Zhang, Z. et al., "Retroviral transfer of antisense integrin α6 or α8 sequences results in laminar redistribution or clonal cell death in developing brain," J. Neuroscience, vol. 18 (17), pp. 6928-6938 (Sep. 1, 1998).
Agrez, M.V. et al., "Colorectal cancer and the integrin family of cell adhesion receptors: current status and future directions", European Journal of Cancer 30A, 2166-2170 (1994).
Agrez, M.V. et al., "Multiplicity of fibronectin-binding αv integrin receptors in colorectal cancer", Br. J. Cancer 73, 887-892 (1996).
Agrez, M.V., "Cell adhesion molecules and colon cancer", A.N.Z.J. Surgery 66, 789-796 (1996).
Bookstein, R. et al., "p53 gene therapy in vivo for hepatocellular and liver metastatic colorectal cancer", Seminars Oncol. 23, 66-77 (1996).
Boulton, T.G. et al., "ERKs: a family of protein-serine/threonine kinases that are activated and tyrosine phosphorylated in response to insulin and NGF", Cell 65, 663-675 (1991).
Cone,. R.I. et al., "Effects of beta subunit cytoplasmic domain deletions on the recruitment of the integrin alpha v beta 6 to focal contacts", Cell Adhes. Comm. 2, 101-113 (1994).
Coppolino, M. et al., "Inducible interaction of integrin alpha 2 beta 1 with calreticulin. Dependence of the activation state of the integrin", J. Biol. Chem. 270, 23132-23138 (1995).
Gamble, J.R. et al., "Regulation of in vitro capillary tube formation by anti-integrin antibodies", J. Cell Biol. 121, 931-943 (1993).
Garrington, T.P. et al., "Organization and regulation of mitogen-activated protein kinase signaling pathways", Curr. Opin. Biol. 11, 211-218 (1999).
Giancotti, F.G. et al., "Integrin signalling", Science 285, 1028-1032 (1999).
Gorgziglia and Kapikian, J., Virol. 66, 4407-4412 (1992).
Grammer, T.C. et al., "Evidence for MEK-independent pathways regulating the prolonged activation of the ERK-Map kinases", Oncogene 14, 1635-1642 (1997).
Guan, J.L. et al., "Regulation of focal adhesion-associated protein tyrosine kinase by both cellular adhesion and oncogenic transformation", Nature 358, 690-692 (1992).
Hannigan, G.E. et al., "Regulation of cell adhesion and anchorage-dependent growth by a new beta 1-integrin-linked protein kinase", Nature 379, 91-96 (1996).
Hemler, M.E., "Integrin associated proteins", Curr. Opin. Biol. 10, 578-585 (1998).
Hergott, G.J. et al., "Inhibition of retinal pigment epithelial cell migration and proliferation with monoclonal antibodies against the beta 1 integrin subunit during wound healing in organ culture", Invest. Ophthalmol. Vis. Sci. 34, 2761-2768 (1993).
Horwitz, A. et al., "Interaction of plasma membrane fibronectin receptor with talin-a transmembrane linkage", Nature 320, 531-533 (1986).
Howe, A. et al., "Integrin signaling and cell growth control", Curr. Opin. Biol. 10, 220-231 (1998).
Knezevic, I. et al., "Direct binding of the platelet integrin alpha Iib beta 3 (GpIlla) to talin. Evidence that interaction is mediated through the cytoplasmic domains of both alpha IIb and beta 3", J. Biol. Chem. 271, 16416-16421 (1996).
Kornberg, L. et al., "Cell adhesion or integrin clustering increases phosphorylation of a focal adhesion-associated tyrosine kinase", J. Biol. Chem. 267, 23439-23442 (1992).
Loftus, J.C. et al., "Integrin-mediated cell adhesion: the extracellular face", J. Biol. Chem. 269, 25235-25238 (1994).
Miranti, C.K. et al., "Protein Kinase C regulates integrin-induced activation of the extracellular regulated kinase pathway upstream of Shc", J. Biol. Chem. 274, 10571-10581 (1999).
Otey, C.A. et al., "An interaction between alpha-actinin and the beta 1 integrin subunit in vitro", J. Cell Biol. 111, 721-729 (1990).
Payne, D.M. et al., "Identification of the regulatory phosphorylation sites in pp42/mitogen-activated protein kinase (MAP kinase)", EMBOJ 10, 885-892 (1991).
Pfaff, M. et al., "Integrin beta cytoplasmic domains differentially bind to cytoskeletal proteins", J. Biol. Chem. 273, 6104-6109 (1998).
Reszka, A.A. et al., "Identification of amino acid sequences in the integrin beta 1 cytoplasmic domain implicated in cytoskeletal association", J. Cell Biol. 117, 1321-1330 (1992).
Rojiani, M.V. et al., "In vitro interaction of a polypeptide homologous to human Ro/SS-A antigen (calreticulin) with a highly conserved amino acid sequence in the cytoplasmic domain of integrin alpha subunits", Biochemistry 30, 9859-9866 (1991).
Schaller, M.D. et al., "Focal adhesion kinase and paxillin bind to peptides mimicking beta integrin cytoplasmic domains", J. Cell Biol. 130, 1181-1187 (1995).
Sheppard, D. et al., "Complete amino acid sequence of a novel integrin β subunit (β6) identified in epithelial cells using the polymerase chain reaction", J. Biol. Chem. 265, 11502-11507 (1990).
Varner, J.A. et al., "Integrin alpha 5 beta 3 expression negatively regulates cell growth: reversal by attachment to fibronectin", Mol. Biol. Cell 6, 725-740 (1995).

Wang, A. et al., "Differential regulation of airway epithelial integrins by growth factors", Am. J. Respira. Cell & Mol. Biol. 15, 664-672 (1996).

Wary, K.K. et al., "The adaptor protein Shc couples a class of integrins to the control of cell cycle progression", Cell 87, 733-743 (1996).

Chen et al., "Distinct Structural Requirements for Interaction of the Integrins α5β1, αvβ5, and αvβ6 with the Central Cell Binding Domain in Fibronectin", Cell Adhesion and Communication, vol. 4, Nos. 4-5, pp. 237-250 (1996).

Coppolino et al., "Bi-directional signal transduction by integrin receptors," The International Journal of Biochemistry & Cell Biology, vol. 32, pp. 171-188 (2000).

Dixit et al., "Identification of a Sequence within the Integrin β6 Subunit Cytoplasmic Domain That Is Required to Support the Specific Effect of αvβ6 on Proliferation in Three-Dimensional Culture", J. Biol. Chem., vol. 271, No. 42, pp. 25976-25980 (1996).

Gotoh et al., "Cross-Linking of Integrins Induces Tyrosine Phosphorylation of the Proto-Oncogene Product Vav and the Protein Tyrosine Kinase Syk in Human Factor-dependent Myeloid Cells", Cell Growth and Differentiation, vol. 8, pp. 721-729 (1997).

Lin et al., "Integrin-mediated Activiation of MAP Kinase Is Independent of FAK: Evidence for Dual Integrin Signaling Pathways in Fibroblasts", J. Cell. Biol., vol. 136, No. 6, (1997).

Sheppard et al., "Complete Amino Acid Sequence of a Novel Integrin β Subunit ($\beta_6$) Identified in Epithelial Cells Using the Polymerase Chain Reaction", J. Biol. Chem., vol. 265, No. 20, pp. 11502-11507 (1990).

Yokosaki et al., "Differential Effects of the Integrins α9β, αvβ, and αvβ6 on Cell Proliferative Responses to Tenascin: Roles to the β Subunit Extracellular and Cytoplasmic Domains," J. Biol. Chem., vol. 271, No. 39, pp. 24144-24150, (1996).

Boulton, T.G., et al., "Mitogen-activated protein kinase 1," (EC 2.7.1) (1991) (Swiss Prot Acc No. P27703).

Breuss, J.M., et al., "Restricted distribution of integrin β6 mRNA in primate epithelial tissues," J Histochem Cytochem (1993), 41: 1521-1527.

Carloni, V., et al., "The integrin α 6 β 1, is necessary for the matrix-dependent activation of FAK and MAP Kinase and the migration of human hepatocarcinoma cells," Hepatology 2001, Jul.; 34(1): 42-9.

Eliceiri, B.P., et al., "The role of αv integrins during angiogenesis: insights into potential mechanisms of action and clinical development," J Clin Invest (1999), 103(9): 1227-30.

Eliceiri, B.P., et al., "Integrin αvβ3 requirement for sustained mitogen activated protein kinase activity during angiogenesis," J Cell Biol (1998), 140(5): 1255-63.

Friedlander, M., et al., "Definition of two angiogenic pathways by distinct αv integrins," Science (1995), 270(5241): 1500-2.

Gonzalez, F.A., "*H sapiens* 40kDa protein kinase related to rat ERK2," (1992) (GenPept Acc No. CAA77753).

Gupta, K., et al., "VEGF prevents apoptosis of human microvascular endothelial cells via opposing effects of MAPK/ERK and SAPK/JNK signaling," Exp Cell Res (1999), 247(2): 495-504.

Ishii, T., et al., "Integrin-linked Kinase Controls Neurite Outgrowth in N1E-115 Neuroblastoma Cells," J. Biol. Chem. (2001), 276(46): 42994-43003.

Pagès, G., et al., "Signaling antiogenesis via p42/p44 MAP kinase cascade," Ann NY Acad Sci (2000), 902: 187-200.

Redlitz, A., et al., "Angiostatin diminishes activation of the mitogen-activated protein kinases ERK-1 and ERK-2 in human dermal microvascular endothelial cells." J Vasc Res (1999), 36(1): 28-34.

Sugiura, N., et al., "*Mus muculus* DNA for ERK2," exon 7 (1997) (GenPept Acc No. BAA22620).

Tanaka, K., et al., "Roles of extracellular signal-regulated kinase 1 / 2 and p38 mitogen-activated protein kinase in the signal transduction of basic fibroblast growth factor in endothelial cells during angiogenesis," Jpn J Cancer Res (1999), 90(6): 647-54.

Yu, Y., et al., "MAP kinases, phosphatidylinositol 3-kinase, and p70 S6 kinase mediate the mitogenic response of human endothelial cells to vascular endothelial growth factor," J Cell Physiol (1999), 178(2): 235-46.

Johnson and Tracy, "Peptide and Protein Drug Delivery," in *Encyclopedia of Controlled Drug Delivery*, vol. 2, 1999, pp. 816-833.

Perez et al., Journal of Cell Science, 1992, pp. 717-722.

* cited by examiner

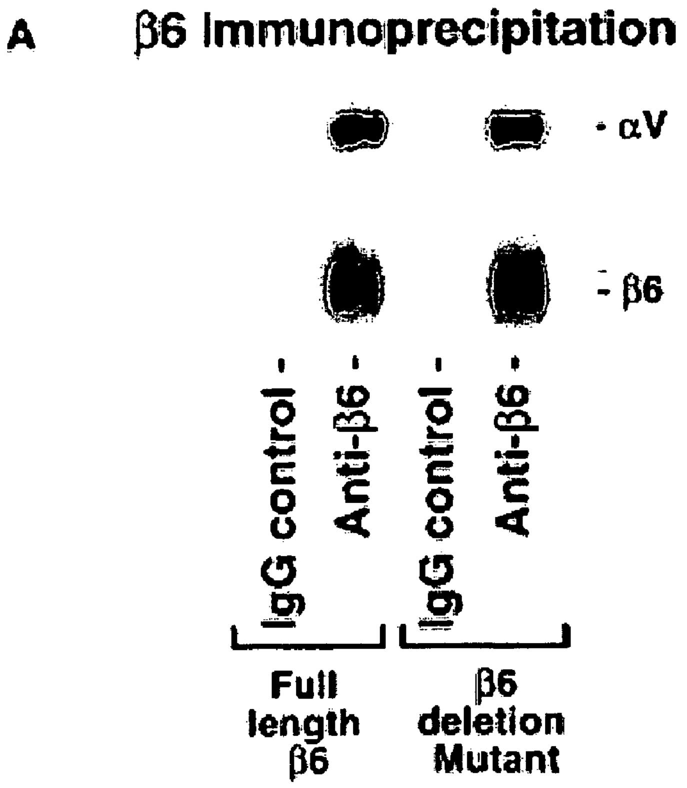
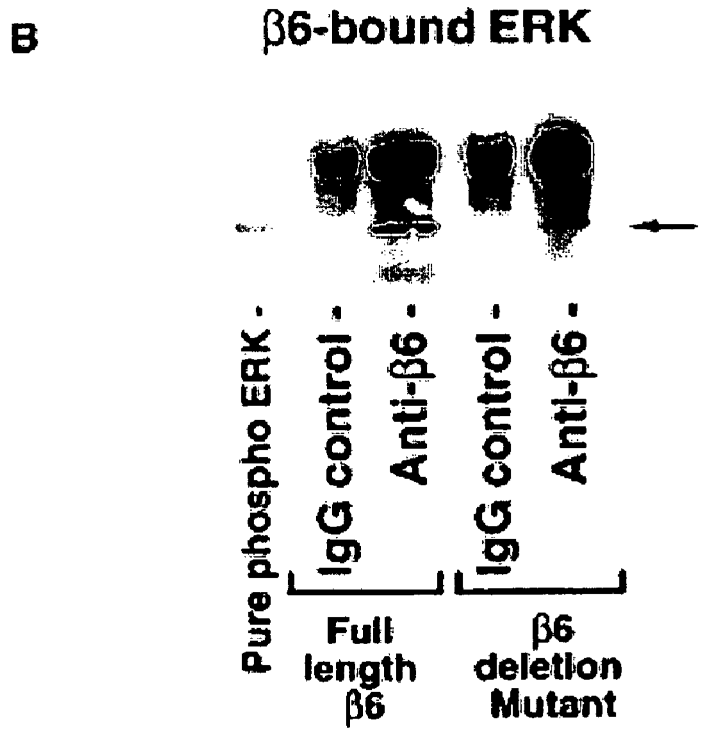
Figure 27

FRK2 (1 uM) binding to B6, B1, B2, B3 & B5 peptides.

Figure 35(A) to (C)

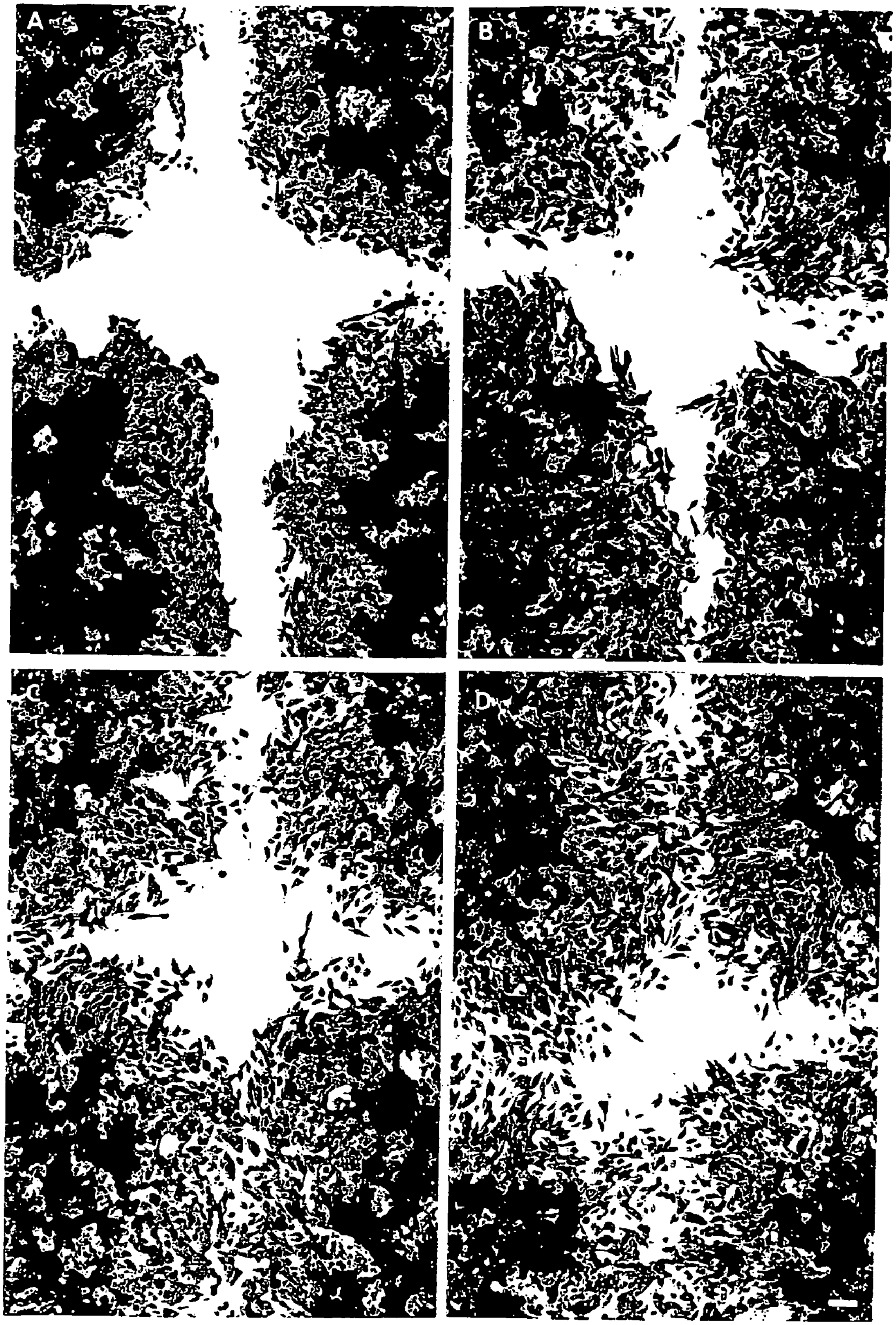
Figure 40(A) to (D)

Figure 41

```
Pro Trp Phe Tyr Arg Arg Leu Val Leu Ser Ser Val Leu Ser Ser Leu Leu Val Pro Asp Arg Arg Gln Pro Ala Thr Arg Ala Ala Ala Arg Phe Leu Trp Glu Ala Gln
CCG TGG TTC TAC CGG CGG TTA GTT CTC TCT TCT GTG TTG TCC TCC CTC CTC GTT CCC GAT CGC CGC CAG CCG GCT ACA CGG GCG GCG GCG CGG TTC CTG TGG GAA GCG CAG  111

His Lys Ser Ser Gly Asn Ala Lys Arg Arg Ala Gln Arg Gly Gly Gly Cys Ala Ala Asn MET Ala Ala Ala Ala Ala Ala Gly Pro Glu MET Val Arg Gly Gln Val Phe
CAC AAG TCG AGC GGT AAC GCG AAG CGT CGA GCC CAA CGC GGC GGA GGC TGT GCA GCC AAC ATG GCG GCG GCG GCG GCG GCG GGC CCG GAG ATG GTC CGC GGC CAG GTG TTC  222
                                                •       • I       •       •                                        • II    •

Asp Val Gly Pro Arg Tyr Thr Asn Leu Ser Tyr Ile Gly Glu Gly Ala Tyr Gly Met Val Cys Ser Ala Tyr Asp Asn Leu Asn Lys Val Arg Val Ala Ile Lys Lys Ile
GAC GTG GGG CCG CGC TAC ACT AAT CTC TCG TAC ATC GGA GAA GGC GCC TAC GGC ATG GTT TGT TCT GCT TAT GAT AAT CTC AAC AAA GTT CGA GTT GCT ATC AAG AAA ATC  333
                                                III •                                          IV

Ser Pro Phe Glu His Gln Thr Tyr Cys Gln Arg Thr Leu Arg Glu Ile Lys Ile Leu Leu Arg Phe Arg His Glu Asn Ile Ile Gly Ile Asn Asp Ile Ile Arg Ala Pro
AGT CCT TTT GAG CAC CAG ACC TAC TGT CAG AGA ACC CTC AGA GAG ATA AAA ATC CTA CTG CGC TTC AGA CAT GAG AAC ATC ATC GGC ATC AAT GAC ATC ATC CGG GCA CCA  444
                                                        V

Thr Ile Glu Gln Met Lys Asp Val Tyr Ile Val Gln Asp Leu Met Glu Thr Asp Leu Tyr Lys Leu Leu Lys Thr Gln His Leu Ser Asn Asp His Ile Cys Tyr Phe Leu
ACC ATT GAG CAG ATG AAA GAT GTA TAT ATA GTA CAG GAC CTC ATG GAG ACA GAT CTT TAC AAG CTC TTG AAG ACA CAG CAC CTC AGC AAT GAT CAT ATC TGC TAT TTT CTT  555
                                        VI                          •                                   VII            •

Tyr Gln Ile Leu Arg Gly Leu Lys Tyr Ile His Ser Ala Asn Val Leu His Arg Asp Leu Lys Pro Ser Asn Leu Leu Leu Asn Thr Thr Cys Asp Leu Lys Ile Cys Asp
TAT CAG ATC CTG AGA GGA TTA AAG TAT ATA CAT TCA GCT AAT GTT CTG CAC CGT GAC CTC AAG CCT TCC AAC CTC CTG CTG AAC ACC ACT TGT GAT CTC AAG ATC TGT GAC  666
 •   •                                                      VIII                                     •   •   •

Phe Gly Leu Ala Arg Val Ala Asp Pro Asp His Asp His Thr Gly Phe Leu Thr Glu Tyr Val Ala Thr Arg Trp Tyr Arg Ala Pro Glu Ile Met Leu Asn Ser Lys Gly
TTT GGC CTT GCC CGT GTT GCA GAT CCA GAC CAT GAT CAT ACA GGG TTC TTG ACA GAG TAT GTA GCC ACG CGT TGG TAC AGA GCT CCA GAA ATT ATG TTG AAT TCC AAG GGT  777
                        •           IX  •

Tyr Thr Lys Ser Ile Asp Ile Trp Ser Val Gly Cys Ile Leu Ala Glu Met Leu Ser Asn Arg Pro Ile Phe Pro Gly Lys His Tyr Leu Asp Gln Leu Asn His Ile Leu
TAT ACC AAG TCC ATT GAT ATT TGG TCT GTG GGC TGC ATC CTG GCA GAG ATG CTA TCC AAC AGG CCT ATC TTC CCA GGA AAG CAT TAC CTT GAC CAG CTG AAT CAC ATC CTG  888
            X

Gly Ile Leu Gly Ser Pro Ser Gln Glu Asp Leu Asn Cys Ile Ile Asn Leu Lys Ala Arg Asn Tyr Leu Leu Ser Leu Pro His Lys Asn Lys Val Pro Trp Asn Arg Leu
GGT ATT CTT GGA TCT CCA TCA CAG GAA GAT CTG AAT TGT ATA ATA AAT TTA AAA GCT AGA AAC TAT TTG CTT TCT CTC CCG CAC AAA AAT AAG GTG CCG TGG AAC AGG TTG  999
                                                                    XI          •

Phe Pro Asn Ala Asp Ser Lys Ala Leu Asp Leu Leu Asp Lys Met Leu Thr Phe Asn Pro His Lys Arg Ile Glu Val Glu Gln Ala Leu Ala His Pro Tyr Leu Glu Gln
TTC CCA AAC GCT GAC TCC AAA GCT CTG GAT TTA CTG GAT AAA ATG TTG ACA TTT AAC CCT CAC AAG AGG ATT GAA GTT GAA CAG GCT CTG GCC CAC CCG TAC CTG GAG CAG  1110

Tyr Tyr Asp Pro Ser Asp Glu Pro Ile Ala Glu Ala Pro Phe Lys Phe Asp Met Glu Leu Asp Asp Leu Pro Lys Glu Lys Leu Lys Glu Leu Ile Phe Glu Glu Thr Ala
TAT TAT GAC CCA AGT GAT GAG CCC ATT GCT GAA GCA CCA TTC AAG TTT GAC ATG GAG CTG GAC GAC TTA CCT AAG GAG AAG CTC AAA GAA CTC ATT TTT GAA GAG ACT GCT  1221

Arg Phe Gln Pro Gly Tyr Arg Ser END
CGA TTC CAG CCA GGA TAC AGA TCT TAA ATTGGTCAGGACAAGGGCTCAGAGGACTGGACGCGTTCAGATGTCGGTGTCCCCCCAGTTCTTGACCCTGGTCCTGTCTCCAGCCCGTCTCAGCTTACCCACTCTTGATTC  1354
     •
CTTTGAGCCCTTCCGACGGGCAGTCTGGTCGTACTGGCTTTTATACTTTCACGGAATTCTTCAGTCCAGAGAGTTCTCCTGCACCAGGCCCTGCACAGTTGCACTCAG  1417
```

MAP KINASE INTEGRIN-BINDING DOMAIN

CROSS REFERENCE TO RELATED APPLICATIONS

This application is a U.S. national stage filing under 35 U.S. 371 from PCT/AU01/01672, entitled MAP KINASE INTEGRIN-BINDING DOMAIN, filed Dec. 21, 2001. Further, this application claims priority to Australian patent application PR 2305, filed Dec. 22, 2000.

FIELD OF THE INVENTION

The present invention relates to a method of modulating cell activity mediated by a mitogen activated protein kinase (MAP) and more particularly, modulation of the growth and/or the proliferation of a cell such as a neoplastic cell. In particular, the invention finds use inter alia in applications requiring modulation of cell activity. The present invention also provides agents for use in the above.

BACKGROUND OF THE INVENTION

Colorectal cancer is the commonest internal malignancy affecting men and women in Australia. About 4% of individuals develop this disease during the course of their lifetime and it was responsible for 14% of cancer deaths in that country in 1990. In 1995 there were 10,615 cases of colorectal cancer and 4508 deaths in Australia.

Worldwide, an estimated 875,000 cases of colorectal cancer occurred in 1996, accounting for 8.5% of all new cases of cancer. Incidence rates vary approximately 20-fold around the world, with the highest rates seen in the developed world and lowest in India. Australian incidence rates are towards the higher end of the scale internationally alongside those for North America and New Zealand. Five-year survival following diagnosis of colon cancer is around 55% in the developed world and has altered little during the past few decades despite advances in chemo-, immuno- and radiotherapy.

Colorectal cancer is a malignant tumour that starts in the bowel wall and is confined locally for a relatively long period before spreading through the bowel wall and metastasising to lymph nodes and other parts of the body. Survival rates are significantly improved where the disease is detected and treated early.

The aetiology of colorectal cancer is complex and appears to involve interactions between inherited susceptibility and environmental factors. Recognition of the genetic component of colorectal cancer is growing. Mutations are present as inherited germline defects or arise in somatic cells secondary to environmental insult. There are two main inherited predisposition syndromes: Familial Adenomatous Polyposis (FAP) and Hereditary Non-Polyposis Colorectal Cancer (HNPCC); the remaining cases are attributed to so-called sporadic colorectal cancer. FAP and HNPCC contribute to approximately 1% and 4%, respectively, of all colorectal cancers and a strong family history of bowel cancer in first-degree relatives is obtained in another 10-15% of patients.

However, in the vast majority of patients the aetiology of large bowel cancer remains unknown. Most colon cancer arises within pre-existing benign precursor lesions or adenomas. Adenomas are classified by histological architecture as tubular, tubulovillous or villous. Villous change is associated with a higher malignant potential, as are large and high-grade epithelial dysplasia. Environmental risk factors for development of colorectal cancer include diets low in fibre and vegetables and high in fat, red meat and alcohol and cigarette smoking which may induce mutations in somatic cells.

Studies have shown that persistent genetic instability and accumulation of mutations in several genes that are mainly concerned with cell growth or DNA repair, may be critical for the development of all colorectal cancers. For example, a normal mucosal cell with inactivation of tumour suppressor genes such as the Adenomatous Polyposis Coli (APC) gene or Mutated in Colon Cancer (MCC) gene can proliferate and become a small adenomatous polyp. Mutations in oncogenes such as k ras and in tumour suppressor genes such as p53 and the Deleted in Colon Cancer gene (DCC) may then occur and lead to the transformation of the polyp into a large adenoma, from which a carcinoma can eventually arise. The uncontrolled cell growth that leads to the development of neoplasia is believed to result, therefore, from a series of inherited and acquired accumulated genetic changes. This multistep process confers on cells the capacity to survive and proliferate in a manner freed from the constraints imposed on normal cell growth.

Spread of cancer cells involves tumour cell migration through the extracellular matrix scaffold, invasion of basement membranes, arrest of circulating tumour cells, and tumour cell extravasation and proliferation at metastatic sites. Detachment of cells from the primary tumour mass and modification of the peri-cellular environment aid penetration of tumour cells into blood and lymphatic vessels. It is the invasive and metastatic potential of tumour cells that ultimately dictates the fate of most patients suffering from malignant diseases. Hence, tumourigenesis can be viewed as a tissue remodelling process that reflects the ability of cancer cells to proliferate and digest surrounding matrix barriers. These events are thought to be regulated, at least in part, by cell adhesion molecules and matrix-degrading enzymes.

Cell adhesion receptors on the surface of colon cancer cells are involved in complex cell signalling which may regulate cell proliferation, migration, invasion and metastasis and several families of adhesion molecules have now been identified including integrins, cadherins, the immunoglobulin superfamily, hyaluronate receptors, and mucins (Agrez, 1996.) In general, these cell surface molecules mediate both cell-cell and cell-matrix binding, the latter involving attachment of tumour cells to extracellular scaffolding molecules such as collagen, fibronectin and laminin. It is now clear that multiple and varied cell adhesion receptors exist on colon cancer cells at any one time and an understanding of the role of individual receptors in promoting growth and spread of colon cancer is only just beginning to be elucidated.

Of all the families of cell adhesion molecules, the best-characterised at the present time is the family known as integrins. Integrins are involved in several fundamental processes including leucocyte recruitment, immune activation, thrombosis, wound healing, embryogenesis, virus internalisation and tumourigenesis. Integrins are transmembrane glycoproteins consisting of an alpha ($\alpha$) and beta ($\beta$) chain in close association that provide a structural and functional bridge between extracellular matrix molecules and cytoskeletal components with the cell. The integrin family comprises 17 different $\alpha$ and 8 $\beta$ subunits and the $\alpha\beta$ combinations are subsumed under 3 subfamilies.

Excluding the leucocyte integrin subfamily that is designated by the $\beta 2$ nomenclature, the remaining integrins are arranged into two major subgroups, designated $\beta 1$ and $\alpha v$ based on sharing common chains.

In the $\beta 1$ subfamily, the $\beta 1$ chain combines with any one of nine $\alpha$ chain members ($\alpha 1$-9), and the a chain which associates with β1 determines the matrix-binding specificity of that receptor. For example, α2β1 binds collagen and laminin, α3β1 binds collagen, laminin and fibronectin, and α5β1 binds fibronectin. In the αv subfamily of receptors, the abundant and promiscuous αv chain combines with any one of five β chains, and a distinguishing feature of αv integrins is that they all recognise and bind with high affinity to arginine-glycine-aspartate (RGD) sequences present in the matrix molecules to which they adhere (Hynes, 1992).

The current picture of integrins is that the N-terminal domains of α and β subunits combine to form a ligand-binding head on each integrin. This head, containing the cation binding domains, is connected by two stalks representing both subunits, to the membrane-spanning segments and thus to the two cytoplasmic domains. The β subunits all show considerable similarity at the amino acid level (Loftus et al, 1994). All have a molecular mass between 90 and 110 kDa, with the exception of β4 which is larger at 210 kDa. Similarly, they all contain 56 conserved cysteine residues, except for β4 which has 48. These cysteines are arranged in four repeating patterns which are thought to be linked internally by disulphide bonds. The α-subunits have a molecular mass ranging from 150-200 kDa. They exhibit a lower degree of similarity than the β chains, although all contain seven repeating amino acid sequences interspaced with non-repeating domains.

The β subunit cytoplasmic domain is required for linking integrins to the cytoskeleton (Hynes, 1992). In many cases, this linkage is reflected in localisation to focal contacts, which is believed to lead to the assembly of signalling complexes that include α-actinin, talin, and focal adhesion kinase (FAK) (Otey et al, 1990; Guan and Shalloway, 1992; Kornberg et al, 1992). At least three different regions that are required for focal contact localisation of β1 integrins have been delineated (Reszka et al, 1992). These regions contain conserved sequences that are also found in the cytoplasmic domains of the β2, β3, β5, β6 and β7 integrin subunits. The functional differences between these cytoplasmic domains with regard to their signalling capacity have not yet been established.

Ligation of integrins by their extracellular matrix protein ligands induces a cascade of intracellular signals that include tyrosine phosphorylation of focal adhesion kinase, increases in intracellular $Ca^{2+}$ levels, inositol lipid synthesis, synthesis of cyclins and expression of immediate early genes. In contrast, prevention of integrin-ligand interactions suppresses cellular growth or induces apoptotic cell death (Meredith et al, 1993; Montgomery et al, 1994; Brooks et al, 1994; Varner et al, 1995; Boudreau et al, 1995). Thus, integrins play roles in a number of cellular processes that impact on the development of tumours, including the regulation of proliferation and apoptosis.

The integrin β6 subunit was first identified in cultured epithelial cells as part of the αvβ6 heterodimer, and the αvβ6 complex was shown to bind fibronectin in an arginine-glycine-aspartate (RGD)-dependent manner in human pancreatic carcinoma cells (Sheppard et al, 1990; Busk et al, 1992). The β6 subunit is composed of 788 amino acids and shares 34-51% sequence homology with other β integrin subunits β1-β5. The β6 subunit also contains 9 potential glycosylation sites on the extracellular domain (Sheppard et al, 1990). The cytoplasmic domain differs from other β subunits in that it is composed of a 41 amino acid region that is highly conserved among integrin β subunits, and a unique 11 amino acid carboxy-terminal extension. The 11 amino acid extension has been shown not to be necessary for localisation of β6 to focal contacts; in fact, its removal appears to increase receptor localisation. However, removal of any of the three conserved regions previously identified as important for the localisation of β1 integrins to focal contacts (Reszka et al, 1992) has been shown to eliminate recruitment of β6 to focal contacts (Cone et al, 1994).

The integrin αvβ6 has previously been shown to enhance growth of colon cancer cells in vitro and in vivo, and this growth-enhancing effect is due, at least in part, to αvβ6-mediated gelatinase B secretion (Agrez et al, 1994; Niu et al, 1998 Agrez et al, 1999). What makes this epithelial-restricted integrin of particular interest in cancer is that it is not expressed on normal epithelial cells but is highly expressed during would healing and tumourigenesis, particularly at the invading edge of tumour cell islands (Breuss et al, 1995; Agrez et al, 1996). Further more, αvβ6 has been found to induce its own expression in an autocrine manner with cell crowding and a self-perpetuating model of colon cancer progression regulated by αvβ6-mediated gelatinase B secretion has been proposed (Niu et al, 2000).

Invasion of the extracellular matrix and metastatic spread of colon cancer is also likely to reflect the ability of tumour cells to digest their surrounding matrix scaffold through secretion of matrix-degrading enzymes such as matrix metalloproteinases (MMPs). The mechanisms whereby human colon cancer cells escape the constraints on growth imposed on normal cells by cell crowding and dense pericellular matrices is unclear. However, even colon cancer cells are subject to relative growth inhibition in vitro in a dense extracellular matrix environment (Agrez, 1989).

Integrins can signal through the cell membrane in either direction. The extracellular binding activity of integrins can be regulated from the cell interior as, for example, by phosphorylation of integrin cytolasmic domains (inside-out signalling), while the binding of the extracellular matrix (ECM) elicits signals that are transmitted into the cell (outside-in signalling) (Giancotti and Ruoslahti, 1999). Outside-in signalling can be roughly divided into two descriptive categories. The first is 'direct signalling' in which ligation and clustering of integrins is the only extracellular stimulus. Thus, adhesion to ECM proteins can activate cytoplasmic tyrosine kinases (e.g. focal adhesion kinase FAK) and serine/threonine kinases (such as those in the mitogen-activated protein kinase (MAPK) cascade) and stimulate lipid metabolism (eg phosphatidylinositol-4,5-biphosphate ($P_1P_2$) synthesis. The second category of integrin signalling is 'collaborative signalling', in which integrin-mediated cell adhesion modulates signalling events initiated through other types of receptors, particularly receptor tyrosine kinases that are activated by polypeptide growth factors (Howe et al, 1998). In all cases, however, integrin-mediated adhesion seems to be required for efficient transduction of signals into the cytosol or nucleus.

MAP kinases behave as a convergence point for diverse receptor-initiated signalling events at the plasma membrane. The core unit of MAP kinase pathways is a three-member protein kinase cascade in which MAP kinases are phosphorylated by MAP kinase kinases (MEKs) which are in turn phosphorylated by MAP kinase kinases (e.g. Raf-1) (Garrington and Johnson, 1999). Amongst the 12 member proteins of the MAP kinase family are the extracellular signal-regulated kinases (ERKs) (Boulton et al, 1991) activated by phosphorylation of tyrosine and threonine residues (Payne et al, 1991) which is the type of activation common to all known MAP kinase isoforms. ERK 1/2 (44 kD and 42 kD MAPks, respectively) share 90% amino acid identity and are ubiquitous components of signal transduction pathways (Boulton et al, 1991). These serine/threonine kinases phosphorylate and modulate the function of many proteins with regulatory functions including other protein kinases (such as $p90^{rsk}$) cytoskeletal proteins (such as microtubule-associated phospholipase $A_2$), upstream regulators (such as the epidermal growth factor receptor and Ras exchange factor) and transcription factors (such as C-Myc and Elk-1). ERKs play a major role in growth-promoting events, especially when the concentration of growth factors available to a cell is limited (Giancotti and Ruoslahti, 1999).

MAP kinases can be activated through non-receptor tyrosine kinases such as focal adhesion kinase (FAK), cytoplasmic tyrosine kinase (pp60 c-srk) (Schlaepher and Hunter, 1998), and growth factors acting through membrane-associated receptor tyrosine kinases. The FAK pathway is activated by most integrins. In addition to activating FAK, some β1 and αv integrins also activate the tyrosine kinase Fynu and through it, the adaptor protein Shc (Wang et al, 1996). It is likely that both FAK and Shc contribute to the activation of Ras and thence to the downstream kinase cascade of Raf-1, MEK, and MAP kinases (Schlaepfer et al, 1994; 1997). It is now generally accepted that the activation of ERK in response to integrin ligation requires Ras signalling (Wary et al, 1996; Schlaepfer and Hunter, 1997). The laminin receptor α6β4, the laminin/collagen receptor α1β1, the fibronectin receptor α5β1 and the RGD binding receptor αvβ3 are linked to the Ras-Raf-MEK-ERK signalling pathway and control of immediate early gene expression (Wary et al, 1996; Maniero et al, 1995; 1997). The ability of integrins to activate ERK may be especially important when the concentration of growth factors available to the cell is limited. In this setting, proliferation is likely to require co-stimulation of ERK through integrins and growth factor receptors (Giancotti and Ruoslahti, 1999). Moreover, activation of ERK in response to integrin ligation may play a role in regulating cell migration (Klemke et al, 1997) possibly by initiating matrix-degrading enzyme secretion.

While there is a good deal of evidence in support of a key role for FAK and the phosphotyrosine-domain-containing adaptor protein Shc (Howe et al, 1998; Giancotti & Ruoslahti, 1999) in the Ras-Raf MEK-MAP kinase activation pathway there are also data implicating alternate pathways independent of MEKs. For example, MEK-independent regulation of MAP kinase activation in NIH3T3 fibroblasts has been shown to be mediated by phosphatidylinositol-3-kinases and the conventional protein kinase C (PKC) isoforms and is thought to be due to inactivation of a MAP kinase inhibitor (Grammer and Blenis, 1997).

Although the mechanism by which PKC regulates integrin function is not known, PKC has been shown to regulate integrin-induced activation of the MAP kinase pathway upstream of Shc. For example, PKC inhibition has been shown to inhibit ERK2 activation by fibronectin receptors without any effect on integrin-induced FAK or paxillin tyrosine phosphorylation (Miranti et al, 1999). Hence, MAP kinase activation is more complicated than a simple linear pathway, and the mechanistic basis for the commonly observed integrin-mediated activation of MAP kinases remains controversial.

The importance of the MAP kinase pathway in promoting colon cancer growth in vivo is now no longer in question. Although relatively little is known about the role of MAP kinase activation in for instance, colon tumour progression, MAP kinase pathways have been shown to be highly activated during the late progression of colorectal cancer (Licato et al, 1997). In a recent breakthrough in this field, a highly potent inhibitor of MAP kinase activation has been identified which is capable of inhibiting human colon cancer growth in immune-deficient mice raising hops for the clinical application of MAP kinase inhibitors in the treatment of colon cancer (Sebolt-Leopold et at, 1999).

Various intracellular proteins may be linked directly or spatially to integrin cytoplasmic domains. Direct interactions have been identified between cytoskeletal proteins such as α-actinin and talin and β1 and β3 integrin tails (Horwitz et al, 1986; Otey et al, 1990; Knezevic et al, 1996; Pfaff et al, 1998). A direct association between FAK and the β1 integrin tail has been suggested based on in vitro β1 peptide studies, but this remains to be confirmed (Schaller et al, 1995). More recently, the cytoplasmic domain of the α4 subunit has been found to be physically associated with the signalling adaptor protein paxillin in Jurkat T cells, and this binding event regulates the kinetics of FAK tyrosine phosphorylation (Liu et al, 1999).

Direct integrin links with the intracellular calcium-binding protein, calreticulin, and integrin-linked kinase (ILK) (Hannigan et al, 1996) have been shown to regulate “inside-out” integrin signalling. For example, calreticulin has been shown to bind to a chain cytoplasmic domains (Rojiani et al, 1991) and modify α2β1 integrin activation by phorbol esters and anti-integrin antibodies (Coppolino et al, 1995). Newly identified integrin-binding molecules include the serine/threonine integrin-linked kinase, ILK, which can associate with the β1, β2 and β3 subunits. When over-expressed, ILK has been shown to reduce anchorage-independent growth and tumourigenicity in nude mice (Hannigan et al, 1996). Co-immunoprecipitation strategies have also demonstrated interactions between integrins and the integral plasma membrane protein IAP, and members of the four transmembrane domain protein family (tetraspans). The extracellular Ig region of the IAP molecule mediates association with αvβ3 and is required for cell binding to vitronectin-coated particles (Lindberg et al, 1996). An emerging model for tetraspans is that they recruit signalling enzymes such as phosphatidylinositol-4-kinase and PKC into complexes with integrins (Hemler, 1998).

Integrins have also been shown to be physically linked with matrix-degrading enzymes and growth factors. For example, the integrin αvβ6 has been shown to bind and activate latent TGFβ1 in keratinocytes (Munger et al, 1999) which is thought to be important in modulating the inflammatory process following epithelial injury. In melanoma cells, αvβ3 binds activated gelatinase A (Brooks et al, 1996), and both insulin and platelet-derived growth factor (PDGF) co-immunoprecipitate with this integrin in NIH3T3 mouse fibroblasts (Schneller et al, 1997). Synergism between integrin-mediated signalling processes and growth factor responses is now well-recognised and Schneller et al (1997) showed that a small subset of each of the insulin receptor and PDGF β-receptor is tyrosine phosphorylated upon growth factor stimulation. Interestingly, this subset can associate with the αvβ3 integrin, and PDGF activity is enhanced in association with increased MAP kinase activity in cells plated on the αvβ3 ligand, vitronectin.

SUMMARY OF THE INVENTION

Broadly stated, the present invention relates to the surprising finding that members of the mitogen activated protein (MAP) kinase family can associate with the cytoplasmic domain of an integrin molecule. It is believed that no member of the MAP kinase family has previously been found to directly associate with any integrin. The identification of this functional relationship permits the rational design of agents for therapeutically or prophylactically modulating cellular activity mediated by the MAP kinase and integrin interaction.

In an aspect of the present invention there is provided an agent capable of binding to a binding domain of an integrin for a MAP kinase.

In another aspect of the present invention there is provided an isolated or purified polypeptide capable of binding to a binding domain of an integrin for a MAP kinase or a homolog, analog, variant or derivative of the polypeptide.

The polypeptide may consist of or comprise the binding domain of the MAP kinase to which the integrin binds or sufficient core amino acid sequence of the binding domain of the MAP kinase to enable binding of the polypeptide to the integrin.

Preferably, the polypeptide will be a fragment of a MAP kinase. Most preferably, the polypeptide will comprise the amino acid sequence HRDLKPSNLLLNTTCDLKICDF-GLAR (SEQ ID NO: 1) or PSNLLLNTTCDLKIC (SEQ ID NO: 2) or a region or regions of such sequences.

Accordingly, in a further aspect of the present invention there is provided a fragment of a MAP kinase wherein the fragment is capable of binding with an integrin, or a homolog, analog, variant or derivative of the fragment.

In another aspect of the present invention there is provided a fragment of a MAP kinase wherein the fragment consists of a binding domain of the MAP kinase for an integrin, or an analog or derivative thereof capable of binding to the integrin.

In another aspect of the present invention there is provided an isolated or purified polypeptide capable of binding to a binding domain of an integrin for a MAP kinase and thereby inhibiting binding of the MAP kinase to the integrin, or an analog or derivative of the polypeptide that is capable of binding to the binding domain of the integrin, wherein the polypeptide is other than a MAP kinase or a fragment of a MAP kinase.

Preferably, a polypeptide or fragment of the invention will have a length of about 150 amino acids or less, more preferably about 100 or 50 amino acids or less and more usually about 40 amino acids or less. Typically, the length will be between about 5 to about 30 amino acids.

In yet another aspect of the present invention there is provided a fusion protein a fusion protein incorporating a binding moiety capable of binding to a binding domain of an integrin for a MAP kinase and thereby inhibiting binding of the MAP kinase to the integrin.

Preferably, the binding moiety will comprise a fragment or polypeptide of the invention. Most preferably, the fusion protein will incorporate a carrier moiety for facilitating passage across the cell membrane. The carrier moiety may be penetratin.

In still another aspect of the present invention there is provided an agent for inhibiting binding of a MAP kinase to an integrin, comprising:

a targeting moiety for targeting a cell expressing the integrin;

a binding moiety for binding to a binding domain of the integrin for the MAP kinase to thereby inhibit the binding of the MAP kinase to the integrin; and a carrier moiety for facilitating passage of the binding moiety across the cell membrane of the cell;

wherein the binding moiety is other than an antibody or an binding fragment thereof.

In another aspect of the present invention there is provided a MAP kinase or a fragment thereof with a mutagenised binding domain for an integrin or in which the binding domain is deleted, or a homolog, analog or variant of the MAP kinase or fragment, wherein capability to bind with the integrin is thereby reduced.

In another aspect of the present invention there is provided an isolated nucleic acid sequence encoding a fragment or polypeptide of the invention or a homolog, analog, variant or derivative of the fragment or polypeptide.

In another aspect of the invention there is provided a nucleic acid sequence coding for a MAP kinase or fragment thereof having a mutagenised binding domain for an integrin or in which the binding domain is deleted or a homolog, analog or variant of the MAP kinase or fragment, wherein capability to bind with the integrin is thereby reduced.

In a still further aspect there is provided an isolated nucleic acid sequence encoding a fusion protein or agent of the invention.

There are also provided antisense nucleic acid sequences complimentary to the sense nucleic sequences of the invention. Such antisense sequences find application in antisense therapy of cells in which down regulation of cellular activity is desired, and include oligonucleotides. Sense oligonucleotides coding for all or part of the binding domain of a MAP kinase for an integrin, or that of a homolog, analog or variant thereof, and complimentary antisense oligonucleotides find particular application as primers or probes. A nucleic acid primer or probe of the invention may be labelled with a suitable reporter molecule for enabling detection of hybridisation of the primer or probe to a target nucleic acid sequence.

In yet another aspect of the present invention there is provided a vector incorporating a nucleic acid sequence of the invention. Typically, the vector will be an expression vector and the nucleic acid sequence will be capable of being transcribed.

In a further aspect of the present invention there is provided a host cell transformed with a vector of the invention.

Preferably, the host cell will be selected from the group consisting of a mammalian cell, an epithelial cell, a neoplastic cell, and a cancer cell. Preferably, the host cell will be a mammalian cell and most preferably, a colon cancer cell.

In yet another aspect of the present invention there is provided an antibody generated with the use of a polypeptide, fragment, agent or fusion protein of the invention.

In a still further aspect of the invention there is provided an antibody and binding fragment thereof capable of binding to a binding domain of a MAP kinase for an integrin.

The antibody may be a polyclonal or monoclonal antibody. Preferably, the antibody is a monoclonal antibody.

In still another aspect of the present invention there is provided a method of screening for an agent capable of binding to a binding domain of a MAP kinase for an integrin, comprising:

(a) testing a number of agents for ability to bind to the binding domain of the MAP kinase for the integrin; and (b) determining if any said agent is capable of binding to the binding domain of the MAP kinase on the basis of the testing.

In yet another aspect of the invention there is provided a method of screening for an agent capable of binding to a binding domain of a MAP kinase for an integrin, comprising:

(a) testing a number of agents for ability to bind to the MAP kinase;

(b) selecting an agent or agents identified as being able to bind to the MAP kinase on the basis of the testing; and (c) utilising the selected said agent or agents in an assay for indicating whether the or any of the selected said agents is capable of binding to the binding domain of the MAP kinase for the integrin.

In another aspect of the present invention there is provided a method of evaluating whether an agent is capable of binding to a binding domain of a MAP kinase for an integrin, comprising:

(a) testing the agent for ability to bind to the binding domain of the MAP kinase for the integrin; and (b) determining if the agent is capable of binding to the binding domain on the basis of the testing.

Preferably, a polypeptide or fragment of the invention comprising or consisting of the binding domain of the MAP kinase or core amino acid sequence of the binding domain or a homolog, analog, variant or derivative of the polypeptide or fragment or core amino acid sequence is used in the testing or assaying for whether an agent is capable of binding to the binding domain of the MAP kinase. Most preferably, the polypeptide or fragment will comprise or consist of the amino acid sequence HRDLKPSNLLLNTTCDLKICDFGLAR (SEQ ID NO: 1) or PSNLLLNTTCDLKIC (SEQ ID NO: 2), core amino acid sequence of such sequences capable of binding to an integrin, or a homolog variant, analog or derivative of such sequences.

Testing or assaying of an agent for ability to bind to the binding domain of the MAP kinase for the integrin and thereby inhibit binding of the MAP kinase to the integrin, may comprise exposing the MAP kinase to the agent(s) to enable binding of the agent(s) to the MAP kinase to occur either in the presence of the integrin or prior to the addition of the integrin. Rather than using the MAP kinase, a polypeptide, fragment of a MAP kinase or other molecule capable of binding to the binding site on the integrin for the MAP kinase may be used in such testing or assaying. Similarly, rather than utilising an intact integrin, a polypeptide or integrin fragment comprising or incorporating the binding domain of the integrin for the MAP kinase, or other molecule capable of binding with the binding domain on the MAP kinase for the integrin, may be utilised.

In still another aspect of the present invention there is provided a method of isolating an agent from a sample utilising a molecule immobilised on a solid support and which is capable of binding to a binding domain of an integrin for a MAP kinase, comprising:

(a) contacting the molecule immobilised on the solid support with the sample under conditions suitable for binding of the agent to the molecule;

(b) eluting the agent from the solid support; and (c) collecting the eluted agent;

wherein the molecule is other than an antibody or binding fragment of an antibody.

The molecule may be the MAP kinase, or a fusion protein, a polypeptide, or a fragment of the invention to which the integrin is capable of binding, or for instance a homolog, analog, variant or derivative of such a polypeptide or fragment.

In yet another aspect of the present invention there is provided the agent so isolated.

An agent of the invention will usually be provided in the form of a pharmaceutical composition. Accordingly, in another aspect of the present invention there is provided a pharmaceutical composition comprising an agent of the invention capable of binding to a binding domain of an integrin for a MAP kinase, and a pharmaceutically acceptable carrier or diluent.

The agent may or not be proteinaceous in nature. Preferably, the agent will comprise a fusion protein, or polypeptide. Most preferably, the agent will be coupled to a carrier molecule for facilitating entry of the agent into a cell.

In a further aspect of the invention there is provided a pharmaceutical composition comprising a nucleic acid sequence of the invention and a pharmaceutically acceptable carrier or diluent. Preferably, the nucleic acid sequence is incorporated into a vector as described herein. Alternatively, the nucleic acid sequence may be joined to a carrier molecule such as penetratin for facilitating entry of the nucleic acid sequence into a target cell.

In another aspect of the present invention there is provided a method of modulating activity of a cell expressing a MAP kinase with a binding domain for an integrin, comprising:

transfecting the cell with an expression vector incorporating a nucleic acid sequence encoding a MAP kinase of a fragment thereof, or a homolog, analog or variant of the MAP kinase or fragment, for being expressed by the cell and having a mutagenised binding domain for the integrin or in which the binding domain has been deleted whereby binding to the integrin is inhibited or prevented.

In still another aspect of the present invention there is provided a method of modulating activity of a cell expressing a MAP kinase with a binding domain for an integrin, comprising:

transfecting the cell with a nucleic acid sequence encoding a fragment of a MAP kinase, or a homolog, analog or variant of the fragment, for being expressed by the cell and capable of binding to the binding domain of an integrin for the MAP kinase.

In yet another aspect of the present invention there is provided a method of modulating activity of a cell, comprising:

transfecting the cell with a nucleic acid encoding a polypeptide for being expressed by the cell wherein the polypeptide is capable of binding to a binding domain of an integrin for a MAP kinase.

In still another aspect of the invention there is provided a method of modulating activity of a cell, comprising causing the expression of a MAP kinase to which an integrin is able to bind to be down-regulated.

Preferably, down-regulation of the expression of the MAP kinase is achieved using an antisense nucleic acid sequence that inhibits expression of gene coding for the MAP kinase. The antisense nucleic acid sequence may be administered to the cell or generated within the cell. Preferably, the cell will be transformed with a vector of the invention for generation of the antisense nucleic acid sequence.

Preferably, the antisense nucleic acid sequence will specifically hybridise with sense nucleic acid sequence coding for at least part of the binding domain of the MAP kinase for the integrin and/or intron sequence between such coding sequence.

Accordingly, in another aspect of the present invention there is provided a method of modulating activity of a cell expressing a MAP kinase with a binding domain for an integrin, comprising:

treating the cell with an antisense oligonucleotide for hybridising with at least part of a nucleic acid sequence coding for the binding domain of a MAP kinase for an integrin to thereby cause expression of the MAP kinase to be down-regulated.

In another aspect of the present invention there is provided a method of modulating activity of a cell expressing a MAP kinase with a binding domain for an integrin, comprising:

treating the cell with an effective amount of an agent capable of binding to the binding domain of the integrin for the MAP kinase, wherein the agent is other than an antibody or a binding fragment thereof.

In a further aspect of the present invention there is provided a method of modulating activity of a cell expressing a MAP kinase with a binding domain for an integrin, comprising:

treating the cell with an effective amount of an agent capable of binding to the binding domain of the MAP kinase, wherein the agent is other than an agent comprising a binding domain of the integrin for the MAP kinase or an analog or derivative thereof.

In yet another aspect of the invention there is provided a method of modulating the activity of a cell, comprising:

contacting the cell with an effective amount of a fusion protein, antibody or other molecule of the invention capable of binding to the binding domain of an integrin for a MAP kinase.

Preferably, modulation of the activity of a cell by a method as described herein will comprise treating a mammal in need of such treatment.

Accordingly, in a further aspect of the present invention there is provided a method of prophylaxis or treatment of a disease or condition in a mammal wherein modulation of cellular activity is desirable, comprising:

administering to the mammal an effective amount of a nucleic acid sequence encoding a MAP kinase or a fragment thereof or a homolog, analog or variant of the MAP kinase or fragment, with a mutagenised binding domain for an integrin or in which the binding domain has been deleted and wherein the nucleic acid sequence is capable of being expressed.

In another aspect of the invention there is provided a method of prophylaxis or treatment of a disease or condition in a mammal wherein modulation of cellular activity is desirable, comprising:

administering to the mammal an effective amount of a nucleic acid capable of causing the expression of a MAP kinase to which an integrin is able to bind to be down regulated.

In a further aspect of the present invention there is provided a method of prophylaxis or treatment of a disease or condition in a mammal wherein modulation of cellular activity is desirable, comprising:

administering to the mammal a nucleic acid sequence encoding a fragment of a MAP kinase, or a homolog, analog or variant of the fragment, for being expressed by the cell and capable of binding to the binding domain of an integrin for the MAP kinase.

In still another aspect of the present invention there is provided a method of prophylaxis or treatment of a disease or condition in a mammal wherein modulation of cellular activity is desirable, comprising:

administering to the mammal an effective amount of a nucleic acid sequence for expression of a polypeptide or a fragment of a MAP kinase within the cell, wherein the polypeptide or fragment is capable of binding to a binding domain of an integrin for the MAP kinase to thereby modulate the cellular activity.

In another aspect of the present invention there is provided a method of prophylaxis or treatment of a disease or condition in a mammal wherein modulation of cellular activity is desirable, comprising:

administering to the mammal an effective amount of an agent capable of binding to the binding domain of an integrin for a MAP kinase, wherein the agent is other than an antibody or a binding fragment thereof.

In another aspect of the present invention there is provided a method of prophylaxis or treatment of a disease or condition in a mammal wherein modulation of cellular activity is desirable, comprising:

administering to the mammal an effective amount of an agent capable of binding to the binding domain of a MAP kinase for an integrin wherein the agent is other than an agent comprising the binding domain of the integrin for the MAP kinase or an analog or derivative thereof.

In another aspect of there is provided a method of treatment or prophylaxis of a disease or condition in a mammal, wherein the disease or condition is responsive to an agent capable of binding to a binding domain of an integrin for a MAP kinase and wherein the agent comprises a polypeptide or fragment of the invention or a homolog, variant, analog or derivative of such a polypeptide or fragment, and the method comprises administering an effective amount of the agent to the mammal.

In yet another aspect of the present invention there is provided a method of treatment or prophylaxis of a disease or condition in a mammal, wherein said condition is responsive to an agent capable of binding to a binding domain of an integrin for a MAP kinase wherein the agent is a fusion protein of the invention.

In another aspect there is provided use of a nucleic acid of the invention in the manufacture of a medicament for administration to a mammal in the prophylaxis or treatment of a disease or condition in which modulation of cellular activity is desirable.

In a still further aspect of the invention there is provided the use of an agent capable of binding to a binding domain of an integrin for a MAP kinase in the manufacture of a medicament for administration to a mammal for the prophylaxis or treatment of a disease or condition in which modulation of cellular activity is desirable, wherein the agent is other than an antibody or binding fragment thereof. The agent may for instance be a polypeptide, fragment or the like as described herein.

In another aspect of the present invention there is provided the use of an agent capable of binding to the binding domain of a MAP kinase for an integrin wherein the agent is other than an agent comprising the binding domain of the integrin for the MAP kinase or an analog or derivative thereof.

In another aspect there is provided the use of fusion protein of the invention in the manufacture of a medicament for administration to a mammal for the prophylaxis or treatment of a disease or condition in which modulation of cellular activity is desirable.

Methods as described above will typically comprise treatment or prophylaxis of cancer or a condition associated with a predisposition to cancer. The cancer may for instance be selected from the group consisting of cancer of the lip, tongue, salivary glands, gums, floor and other areas of the mouth, oropharynx, nasopharynx, hypopharynx and other oral cavities, oesophagus, stomach, small intestine, duodenum, colon, rectum, gallbladder, pancreas, larynx, trachea, bronchus, lung, breast, uterus, cervix, ovary, vagina, vulva, prostate, testes, penis, bladder, kidney, thyroid and skin.

In still another aspect of the present invention there is provided a method of causing an activity of a cell to be upregulated, comprising:

contacting the cell with an effective amount of a nucleic acid capable of being expressed within the cell and coding for an agent capable of binding to a binding domain of a MAP kinase for an integrin or a binding domain of the integrin for the MAP kinase.

In a still further aspect of the invention there is provided a method of causing an activity of a cell to be upregulated, comprising contacting the cell with an effective amount of an agent capable of binding to a binding domain of a MAP kinase for an integrin or a binding domain of the integrin for the MAP kinase.

Typically, the agent will be a polypeptide or fragment of an integrin comprising or consisting of the binding domain of an integrin for a MAP kinase or comprising or consisting of the core amino acid sequence of the binding domain directly involved in the binding to the MAP kinase, or a homolog, variant, analog or derivative of such polypeptide or fragment.

Preferably, the polypeptide or fragment will have a length of about 150 amino acids or less, more preferably about 100 or 50 amino acids or less and more usually about 40 amino acids or less. Typically, the length will be between about 5 to about 30 amino acids.

Most preferably, the polypeptide will comprise or consist of the amino acid sequence RSKAKWQTGTNPLYR (SEQ ID NO: 7) or RSKAKNPLYR (SEQ ID NO: 8).

Up regulation of cellular activity is particularly desirable for instance in wound healing, re-endothelialisation within natural or artificial blood vessels, nerve growth and for instance induction of labour.

The cellular activity desired to be modulated will typically but not exclusively, be cell growth or proliferation. Indeed, any activity mediated by MAP kinase signalling is expressly included within the scope of the invention.

The cell may be any cell type in which functional activity arising from signalling mediated by a MAP kinase may occur. Preferably, the cell will be an epithelial cell and usually, a neoplastic cell.

Usually, the MAP kinase will be selected from the group consisting of an extracellular signal-regulated kinase (ERK) and a JNK MAP kinase. Preferably, the MAP kinase is ERK2 or JNK-1. Most preferably, the MAP kinase is ERK2.

The mammal may be any mammal treatable with a method of the invention. For instance, the mammal may be a member of the bovine, porcine, ovine or equine families, a laboratory test animal such as a mouse, rabbit, guinea pig, a cat or dog, a primate or a human being. Preferably, the mammal will be a human being.

As will be understood, modulation of cellular activity within the context of the invention may be up regulation or down regulation of cellular activity. Reference to "down modulation" or "down-regulating" or the like should be understood to include preventing, reducing or otherwise inhibiting one or more aspects of the activity of the cell. Conversely, reference to "up regulation" or like terms should be understood to include enhancing or increasing one or more aspects of the activity of the cell.

In the broadest sense, the term "integrin" unless otherwise specified, is to be taken to encompass an integrin family member or a homolog, derivative, variant or analog of an integrin subunit, or an integrin family member incorporating at least one such homolog, derivative, variant or analog of an integrin subunit. Usually, the integrin will be a member of the αv subfamily. Preferably, the integrin is or incorporates an integrin subunit selected from the group consisting of β3, β5 and β6. Most preferably, the integrin comprises β6.

By "binding domain" is meant the minimum length of contiguous amino acid sequence required for binding. By "core amino acid sequence" is meant regions or amino acids of the binding domain that directly participate in the binding as distinct from any amino acids that do not directly participate in the binding interaction. Typically, the core amino acid sequence of the binding domain will comprise regions of the binding domain linked together by a number of intervening amino acids which do not directly participate in the binding.

The term "homolog" is to be taken to mean a molecule that has amino acid sequence similarity. The homology between amino acid sequences can be determined by comparing amino acids at each position in the sequences when optimally aligned for the purpose of comparison. The sequences are considered homologous at a position if the amino acids at that position are the same. Typically, a homolog will have an overall amino acid sequence homology of at least about 30% more preferably at least about 50% or 70% and most preferably, greater than about 80%, 90% or 98% sequence homology. Homology with a binding domain may be greater than the overall amino acid sequence homology of the homolog, and will usually be greater than about 60% or 80%, and more usually greater than about 90%, 95% or 98%.

The term "analog" is to be taken to mean a molecule that has one or more aspects of biological function characteristic of the molecule on which at least part of the analog is based or which was otherwise utilised in the design or preparation of the analog. An analog may have substantial overall structural similarity with the molecule or only structural similarity with one or more regions or domains thereof responsible for the desired characteristic biological function. By "structural" similarity is meant similarity in shape, conformation and/or other structural features responsible for the provision of the biological function or which otherwise have involvement in the provision of the biological function. Alternatively, it will be understood that with knowledge of the region(s) or domain(s) of a molecule that provide(s) the characteristic biological function, analogs may be designed that while differing in structure nevertheless possess such biological function. Indeed, it is not necessary that an analog have amino acid sequence homology, and an analog may not be proteinaceous at all. An analog may for instance be a mimetic of a molecule.

By the term "variant" is meant an isoform, an allelic variant of a gene or region thereof, a naturally occurring mutant form of a gene or region thereof, or a polypeptide or fragment having an amino acid sequence that differs in one or more amino acids but which retains one or more aspects of desired characteristic biological function. This may be achieved by the addition of one or more amino acids to an amino acid sequence, deletion of one or more amino acids from an amino acid sequence and/or the substitution of one or more amino acids with another amino acid or amino acids. Inversion of amino acids and any other mutational change that results in alteration of an amino acid sequence are also encompassed. A variant may be prepared by introducing nucleotide changes in a nucleic acid sequence such that the desired amino acid changes are achieved upon expression of the mutagenised nucleic acid sequence, or for instance by synthesising an amino acid sequence incorporating the desired amino acid changes which possibility is well within the capability of the skilled addressee.

Substitution of an amino acid may involve a conservative or non-conservative amino acid substitution. By conservative amino acid substitution is meant replacing an amino acid residue with another amino acid having similar stereochemical properties (eg. structure, charge, acidity or basicity characteristics) and which does not substantially effect conformation or the desired aspect or aspects of characteristic biological function. Preferred variants include ones having amino acid sequences in which one or more amino acids have been substituted with alanine or other neutrally charged amino acid residue(s), or to which one or more such residues have been added. A variant may also incorporate an amino acid or amino acids that are not encoded by the genetic code.

By the term "derivative" is meant a molecule that is derived or obtained from another molecule and which retains one or more aspects of characteristic biological function of that molecule. A derivative may for instance arise as a result of the cleavage of the parent molecule, cyclisation and/or coupling with one or more additional moieties that improve solubility, lipophilic characteristics to enhance uptake by cells, stability or biological half-life, decreased cellular toxicity, or for instance to act as a label for subsequent detection or the like. A derivative may also result from post-translational or postsynthesis modification such as the attachment of carbohydrate moieties or chemical reaction(s) resulting in structural modification(s) such as the alkylation or acetylation of amino acid residues or other changes involving the formation of chemical bonds.

The term "polypeptide" is used interchangeably herein with "peptide" and encompasses amino acid sequences incorporating only a few amino acid residues or many amino acid residues coupled by peptide bonds.

The term "neoplastic cell" is to be taken to mean a cell exhibiting abnormal growth and may or may not be a malignant cell. "Growth" is to be taken in its broadest sense and includes proliferation of the cell. In this regard, an example of abnormal cell growth is the uncontrolled proliferation of a cell.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

The features and advantages of the present invention will become further apparent from the following detailed description of preferred embodiments and the accompanying drawings.

BRIEF DESCRIPTION OF THE ACCOMPANYING DRAWINGS

Figure 2:
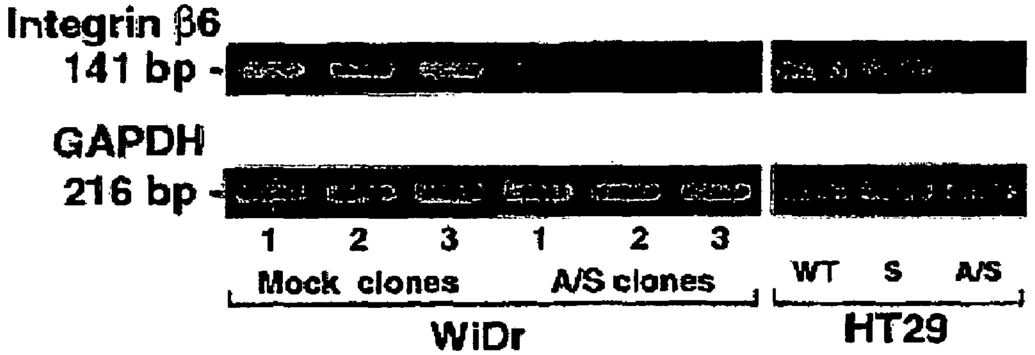
Figure 3:
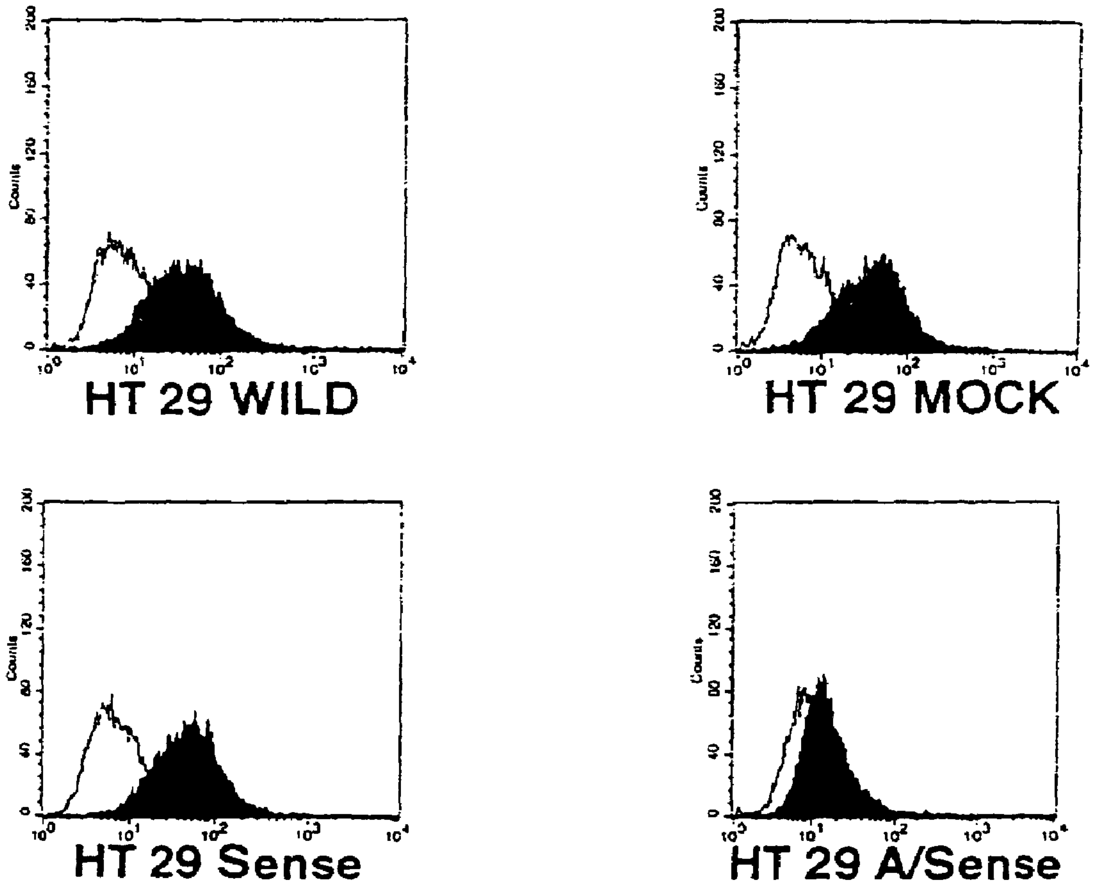
Figure 4:
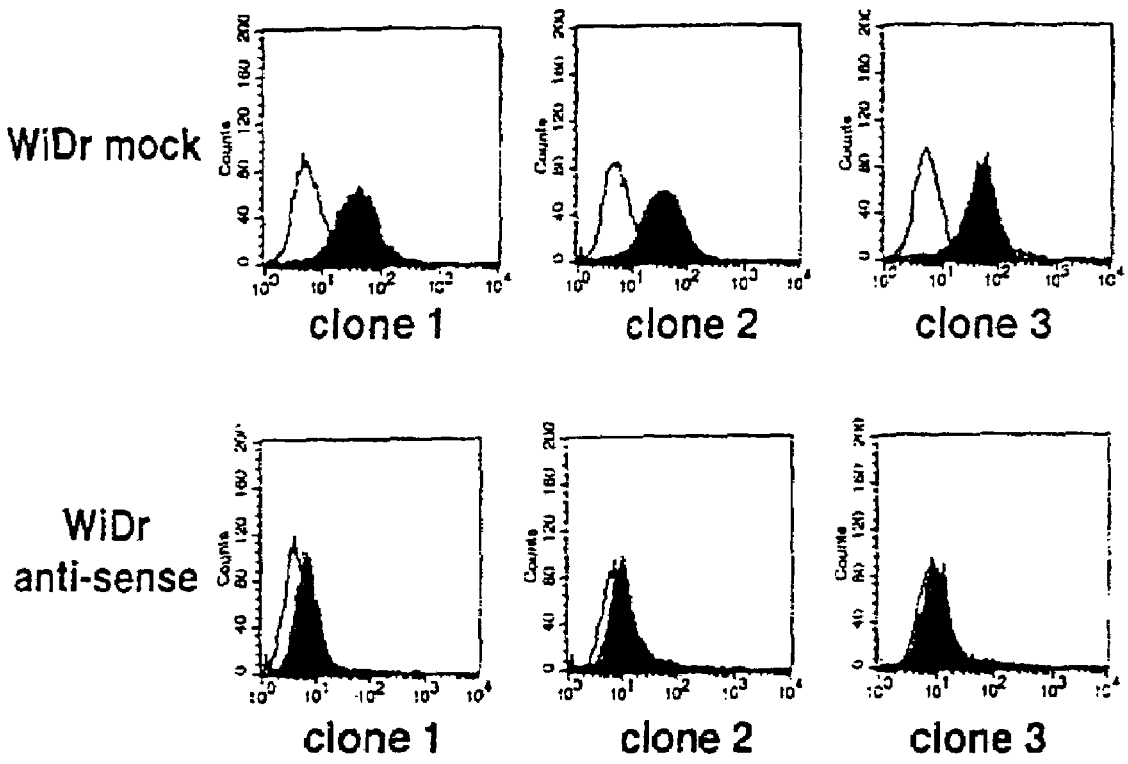
Figure 5:
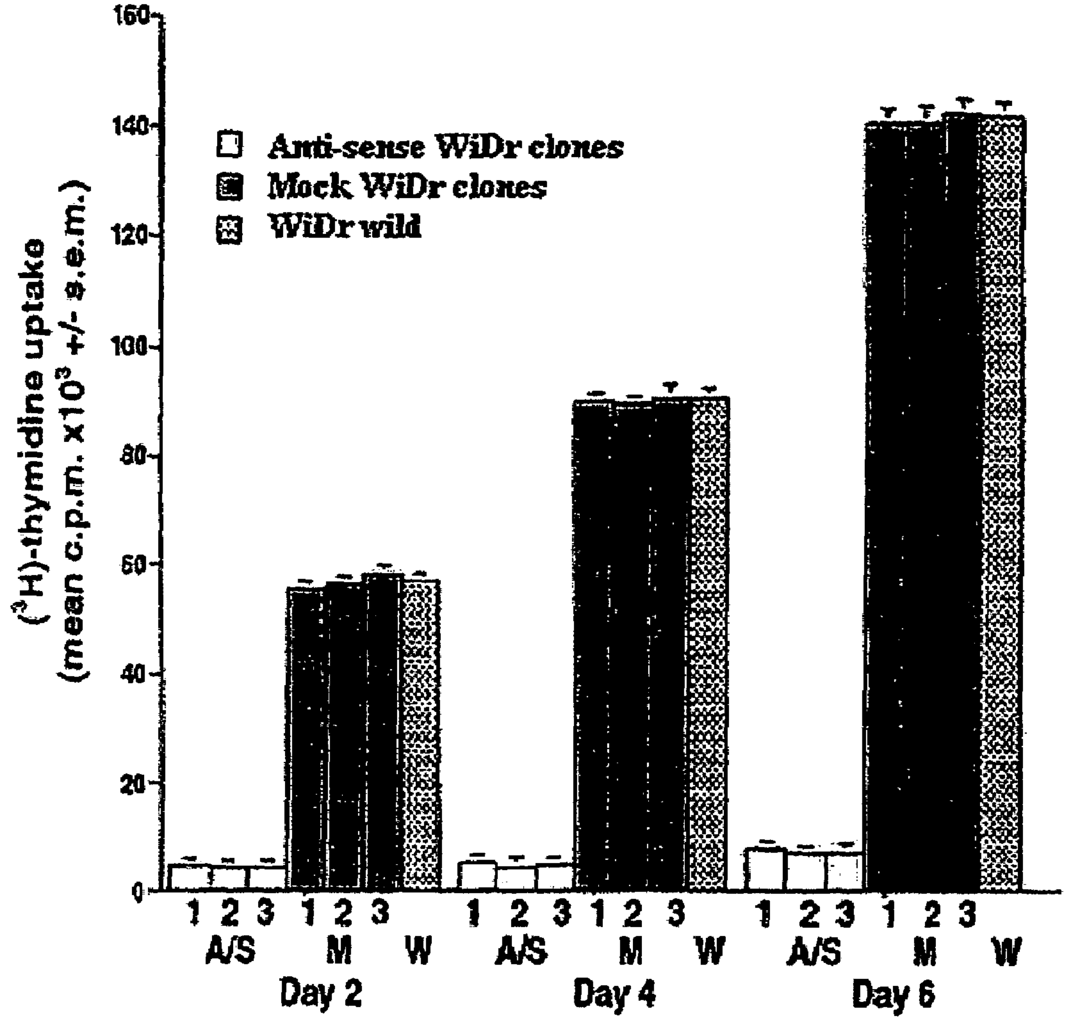

FIG. 1: Surface biotinylation and immunoprecipitation of integrin subunits β5 and β6 in HT29 colon cancer cells stably transfected with either vector alone (mock transfectants) or antisense β6 construct;

FIG. 2: Amplification of β6 and glyceraldehyde dehydrogenase (GAPDHu) mRNA: Ethidium-stained agarose gels with amplification products following RT-PCR from total RNA extracted from transfected HT29 and WiDr cell lines. Equal amounts of PCR product obtained from RT-PCR reactions were loaded on each lane and the β6 (141 basepairs) and GAPDH (216 basepairs) bands are indicated (WT, wild-type; S, sense β6; A/S, antisense β6; mock, vector alone);

FIG. 3: Non-transfected HT29 cells (wild) and cells transfected with vector alone (mock), sense β6 and antisense β6 analysed by FACScan for expression of the β6 subunit. White and black histograms represent cells stained in the absence and presence, respectively, of mAb E7P6 (anti-β6);

FIG. 4: WiDr cells transfected with vector alone (mock) or antisense β6 and analysed by FACScan for expression of the β6 subunit. White and black histograms represent cells stained in the absence and presence, respectively, of mAb E7P6 (anti-β6);

FIG. 5: Tumor cell proliferation in vitro assessed by ($^3$H)-thymidine uptake for WiDr wild-type cells and transfectants (mock and antisense β6) cultured on plastic for the times indicated.

Figure 6:
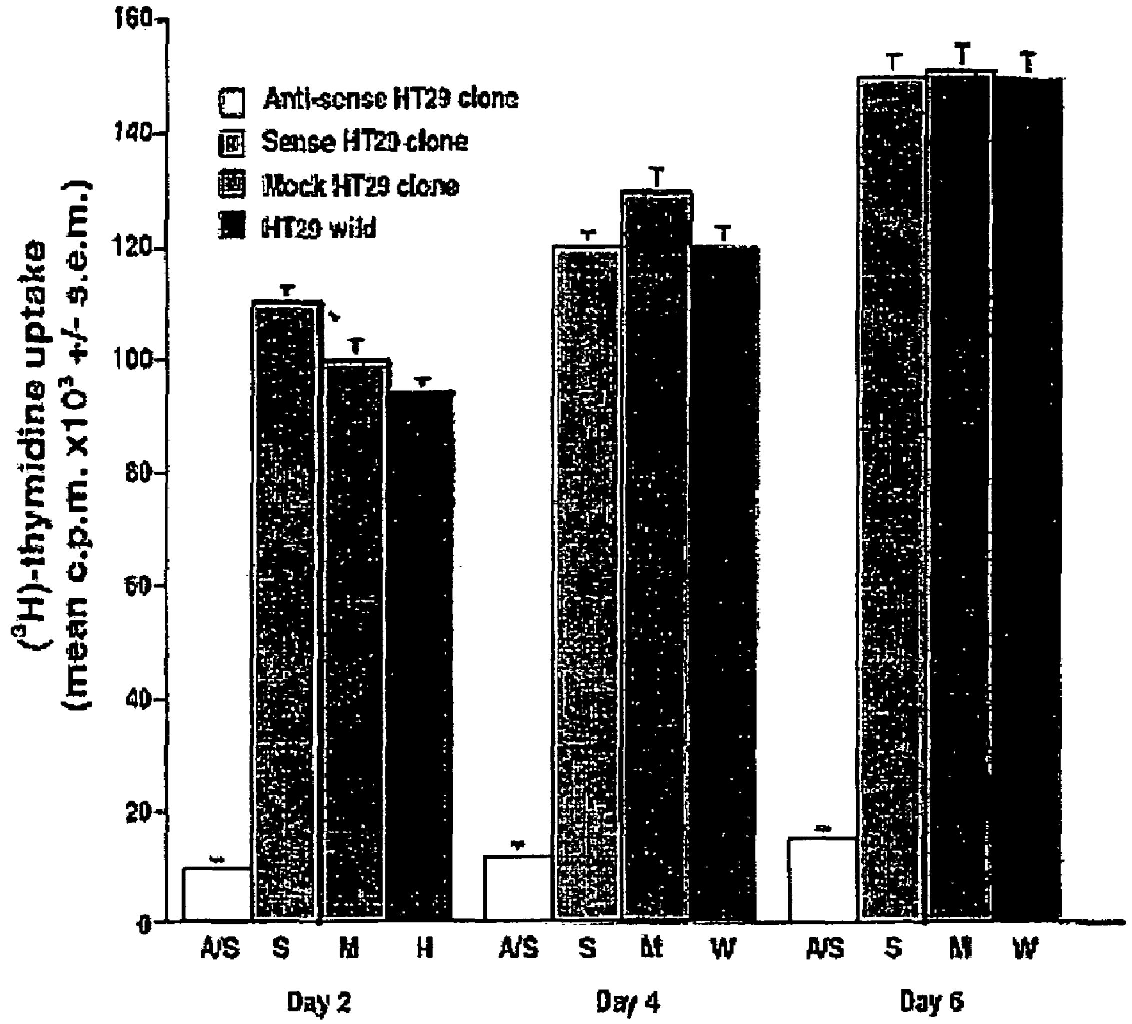

FIG. 6: Tumor cell proliferation in vitro assessed by ($^3$H)-thymidine uptake for HT29 wild-type cells and transfectants (mock, sense β6 and antisense β6) cultured on plastic for the times indicated.

Figure 7:
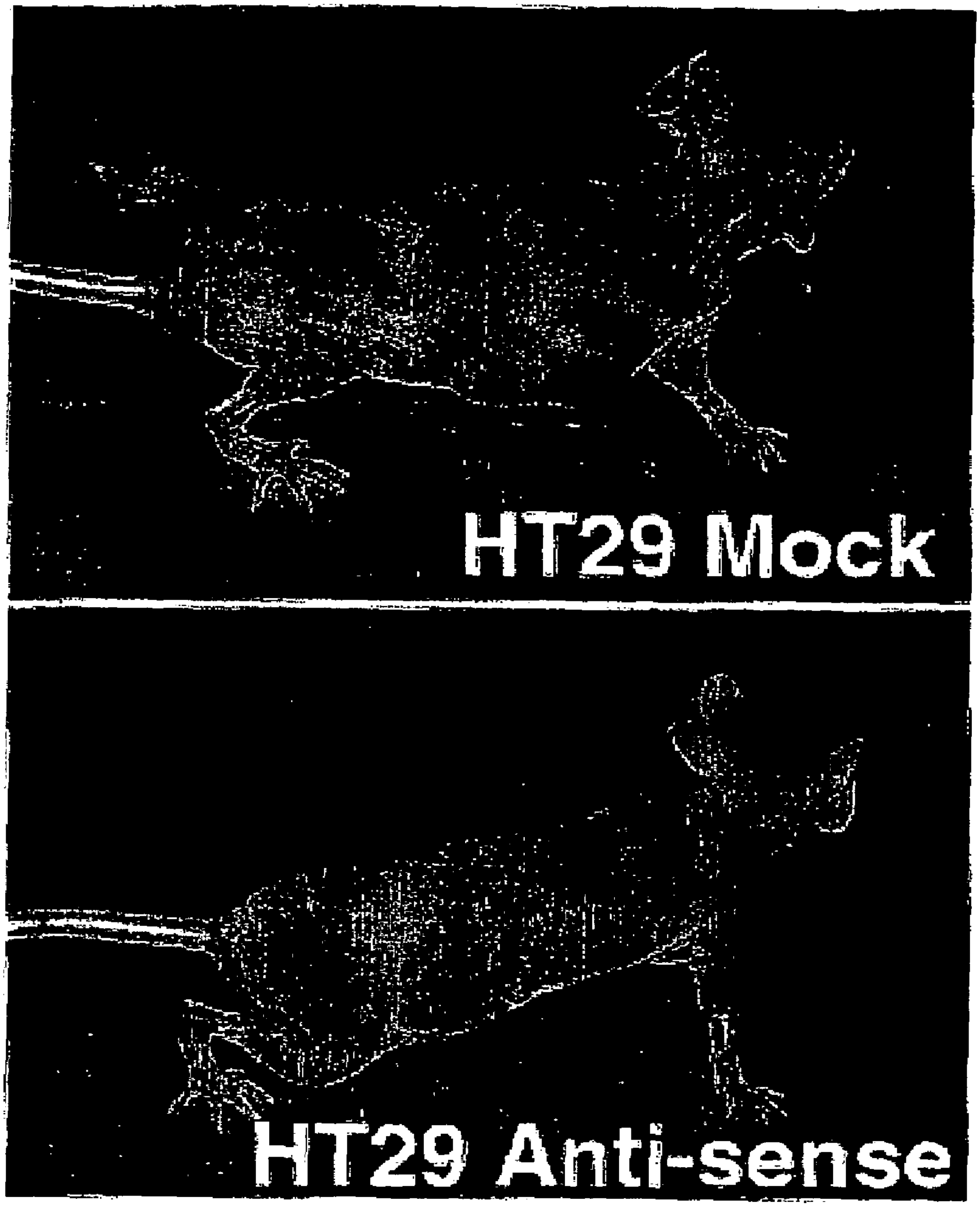
Figure 8:
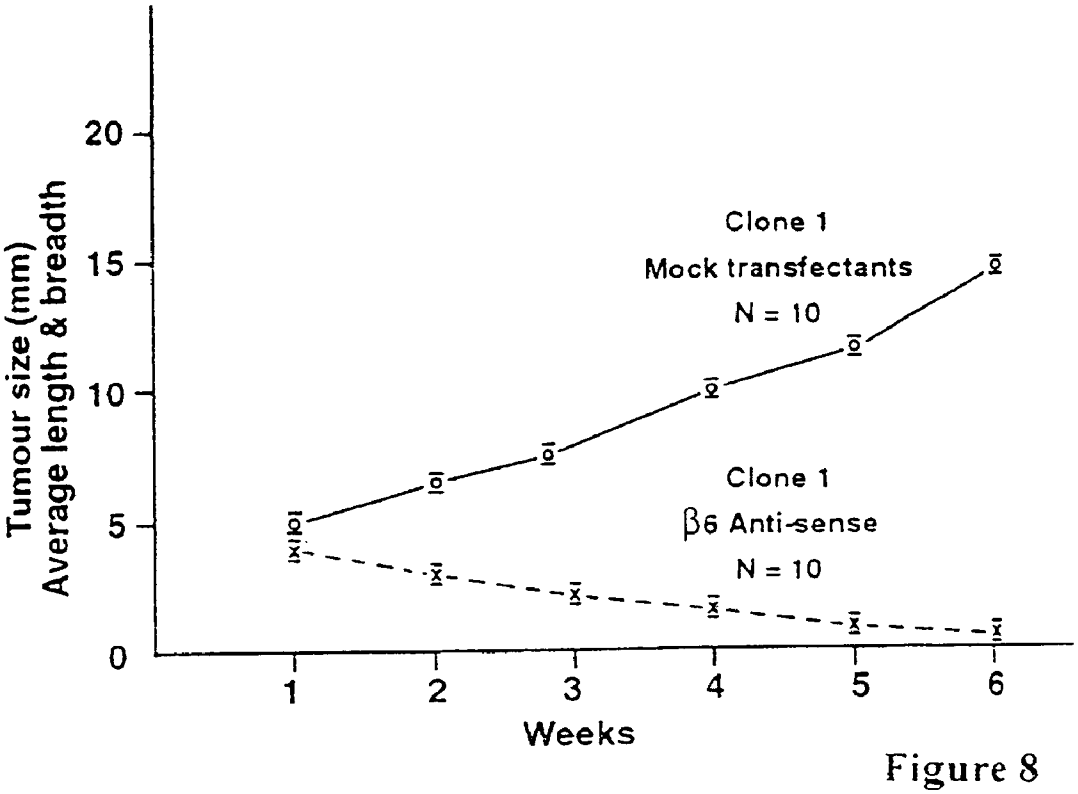
Figure 9:
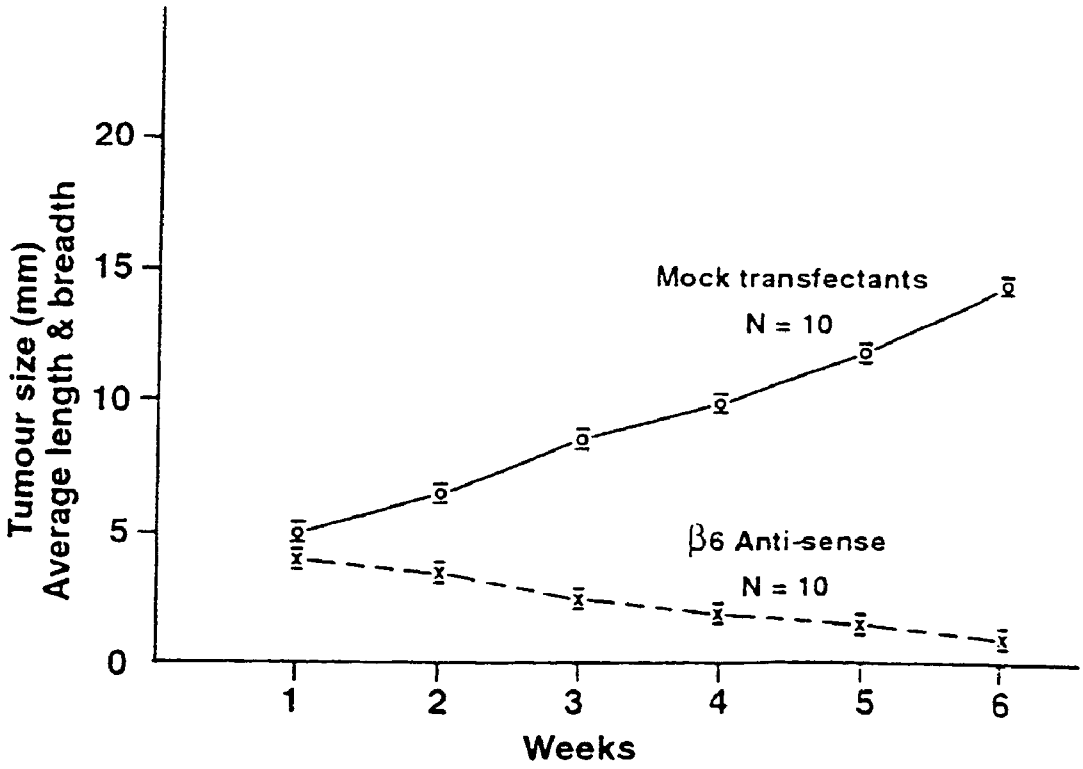
Figure 10:
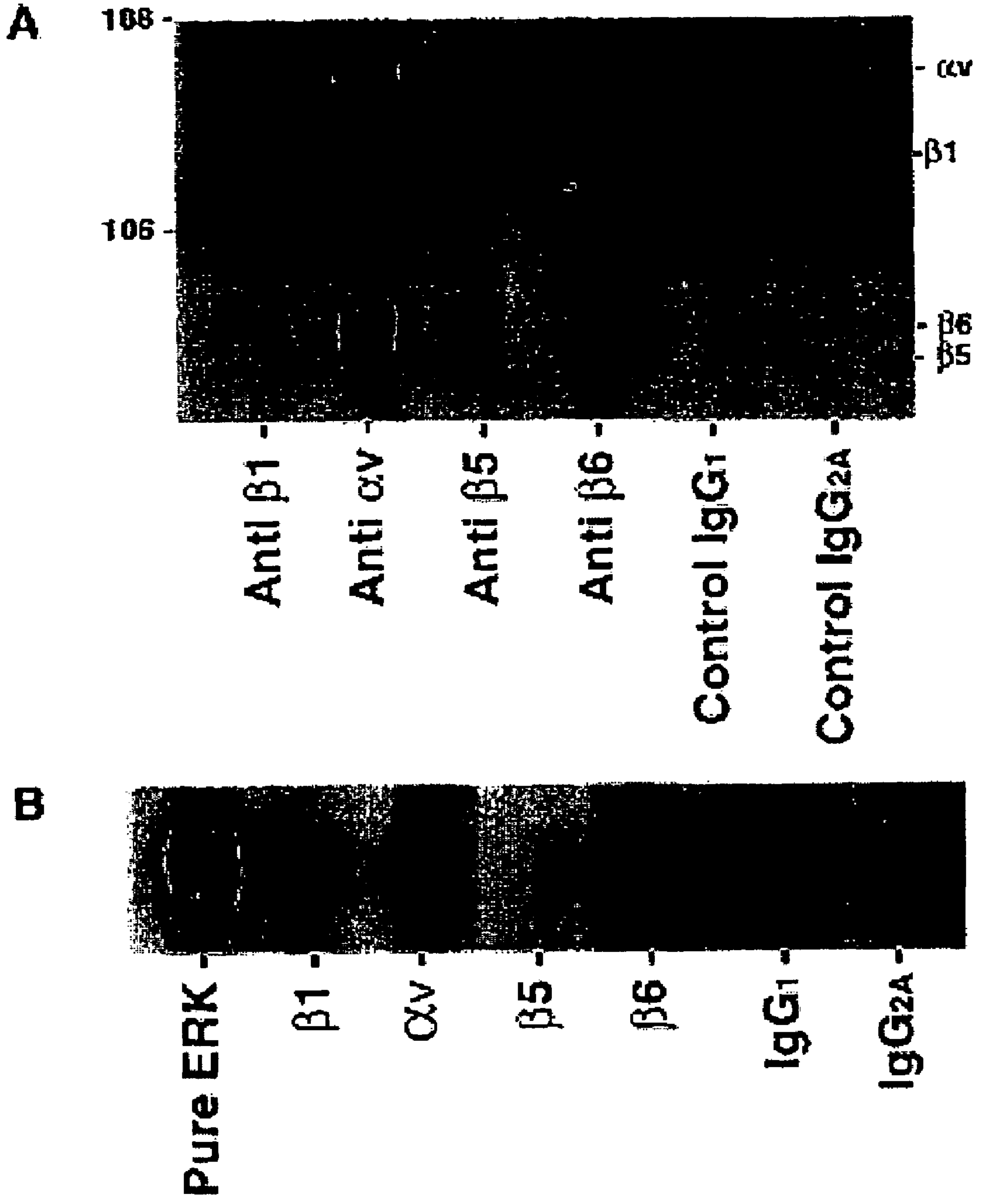
Figure 11:
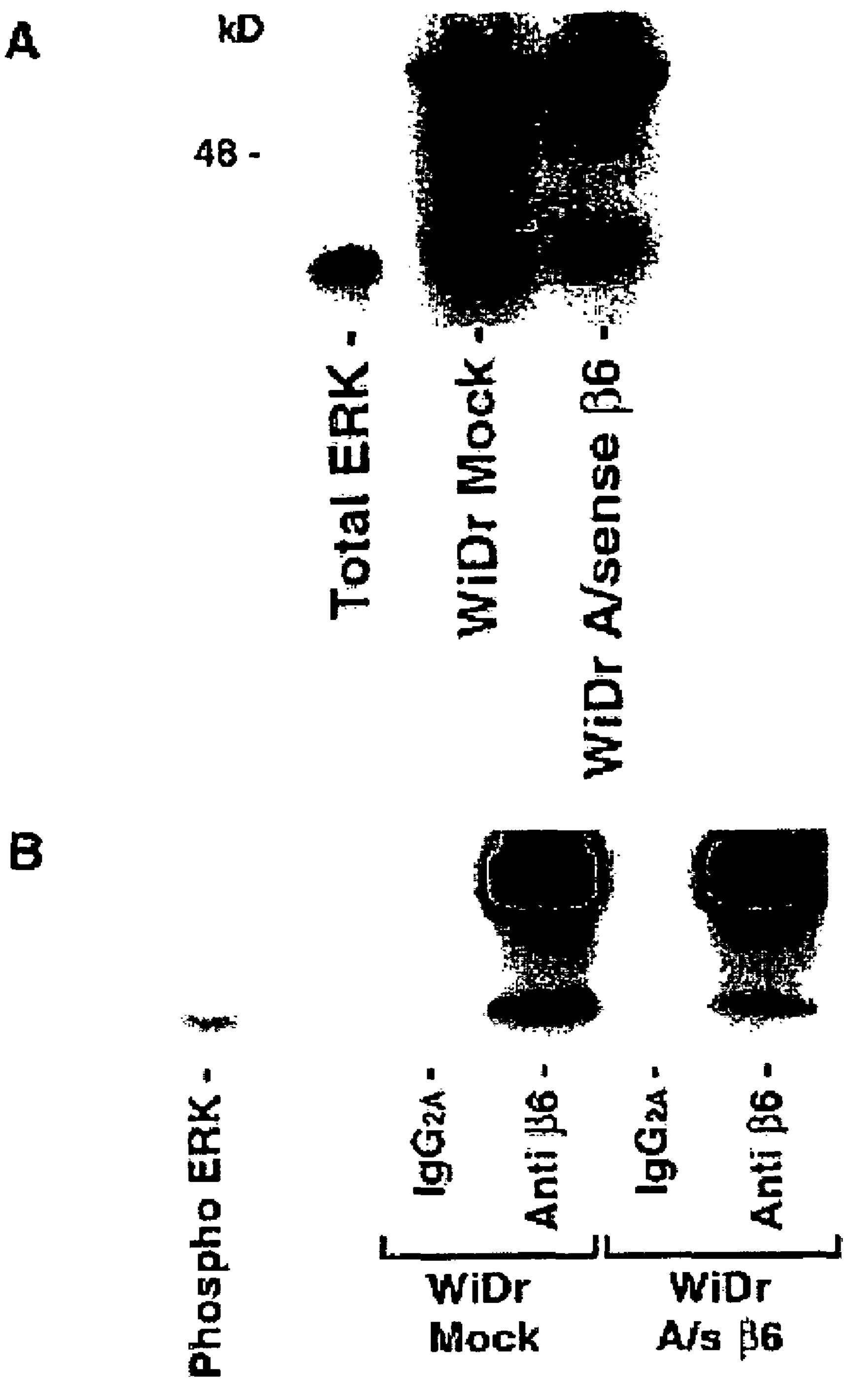
Figure 12:
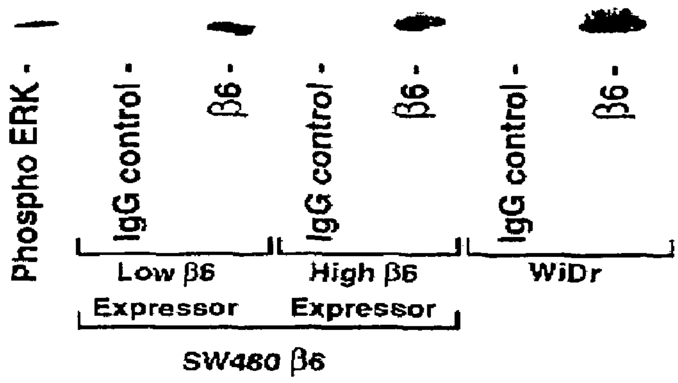
Figure 13:
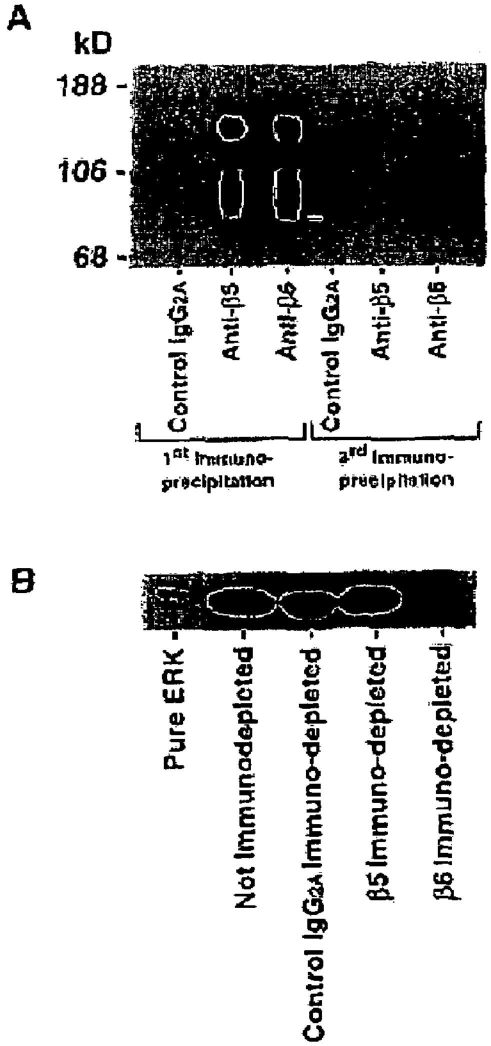
Figure 14:
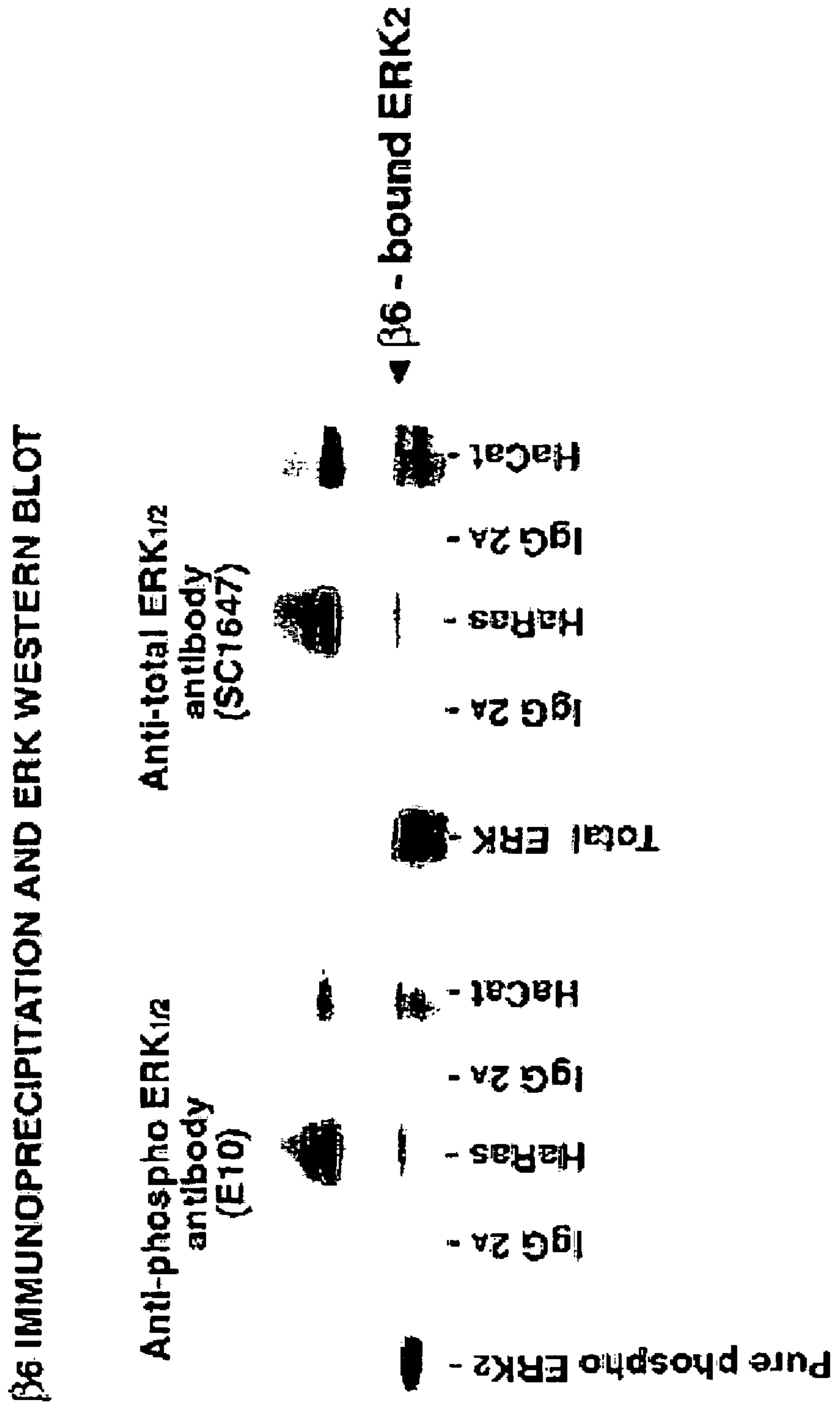

FIG. 7: Tumour growth after 6 weeks following subcutaneous inoculation of $10^6$ viable cells of HT29 mock (vector alone) and antisense β6 transfectants;

FIG. 8: Graph showing average tumour size at weekly intervals for each subgroup of 10 animals following subcutaneous inoculation of clone 1 from WiDr mock (vector alone) and antisense β6 transfectants;

FIG. 9: Graph showing average tumour size at weekly intervals for each subgroup of 10 animals following subcutaneous inoculation of HT29 mock (vector alone) and antisense β6 transfectants;

FIG. 10: β6-associated ERK identified by immunoprecipitations of integrin subunits from SW480 β6 transfectants. (Top) Cell lysates were immunoprecipitated with mAbs QE2E5 (anti-β1), L230 (anti-αv), P1F6 (anti-β5), R6G9 (anti-β6), or matched isotype control Abs (IgG1 and IgG2A), and (bottom) blotted with anti-ERK1/2 mAb, SC-1647, which recognises total ERK (phosphorylated and non-phosphorylated). Purified, non-phosphorylated ERK2 is shown in the left hand lane;

FIGS. 11(A) and 11(B): (A) Western blotting: equal protein loads of cell lysates from one representative clone each from WiDr mock and antisense β6 blotted with anti-ERK mAb (SC-1647) against total ERK. Purified non-phosphorylated ERK2 is shown in the left hand lane. (B) β6 immunoprecipitates (mAb R6G9) from equal protein loads of the cell lysates in (A) probed with anti-ERK mAb (E10). Purified phosphorylated ERK2 is shown in the left hand lane;

FIG. 12: β6-bound ERK shown for the high and low SW480 β6-expressing clones by probing β6 immunoprecipitates with anti-ERK mAb (E10) against phosphorylated forms of ERK1/2. Purified, phosphorylated ERK2 is shown in the left hand lane;

FIGS. 13(A) and 13(B): (A) Surface biotinylation of WiDr wild-type cells and β6 immunodepletion of the cell lysates by three successive rounds of β6 and β5 immunoprecipitations using mAb R6G9 and P1F6, respectively or control mAb (IgG2A). The β6 and partner αv bands are arrowed. (B) β6-immunodepleted WiDr cell lysates after 3 successive rounds of β6-immunoprecipitations probed with anti-ERK mAb SC-1647 recognising both phosphorylated and non-phosphorylated forms of ERK1/2 and compared with non-β6 immunodepleted lysates and control lysates sequentially immunoprecipitated 3 times with either isotype matched control mAb (IgG2A) or mAb P1F6 (anti-β5);

FIG. 14: Non-transformed (HaCaT) and Ras-transformed (HaRas) human keratinocytes: β6 immunoprecipitation and ERK western blots probed with monoclonal antibody E10 (against Phosphorylated ERK 1/2) and monoclonal antibody SC1647 (against total ERK 1/2), respectively.

Figure 15:
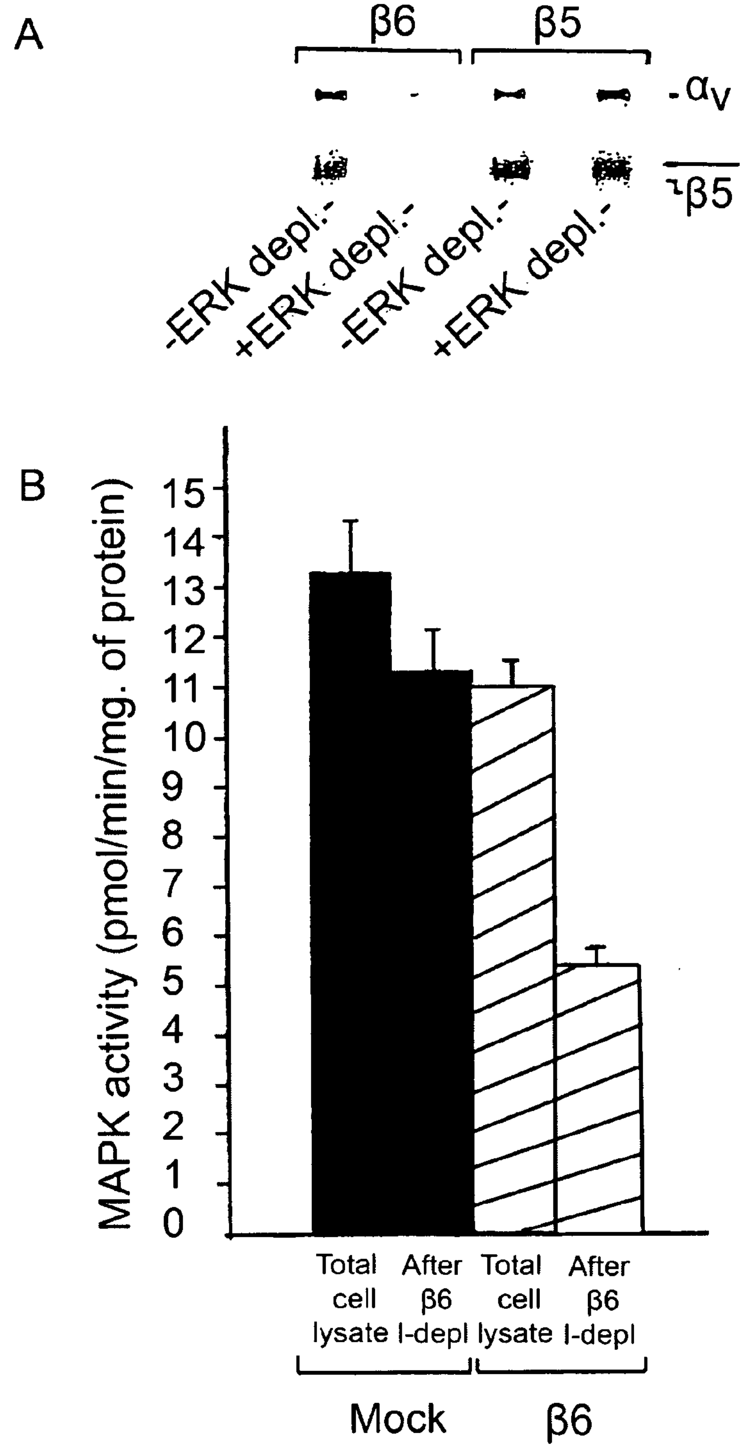

FIGS. 15(A) and 15(B): (A) Depletion of β6 with sequential rounds of ERK immunodepletion of cell lysates using anti-ERK mAb (SC-1647). (B) MAP kinase activity in cell lysates before and after 5 rounds of sequential β6 immunodepletion from SW480 β6 and SW480 mock transfectants (full grey and hatched bars, respectively). MAP kinase activity is shown as the mean of three independent experiments. The reduction in MAP kinase activity following β6 immunodepletion was highly significant ($P \leqq 0.005$, students T test).

Figure 16:
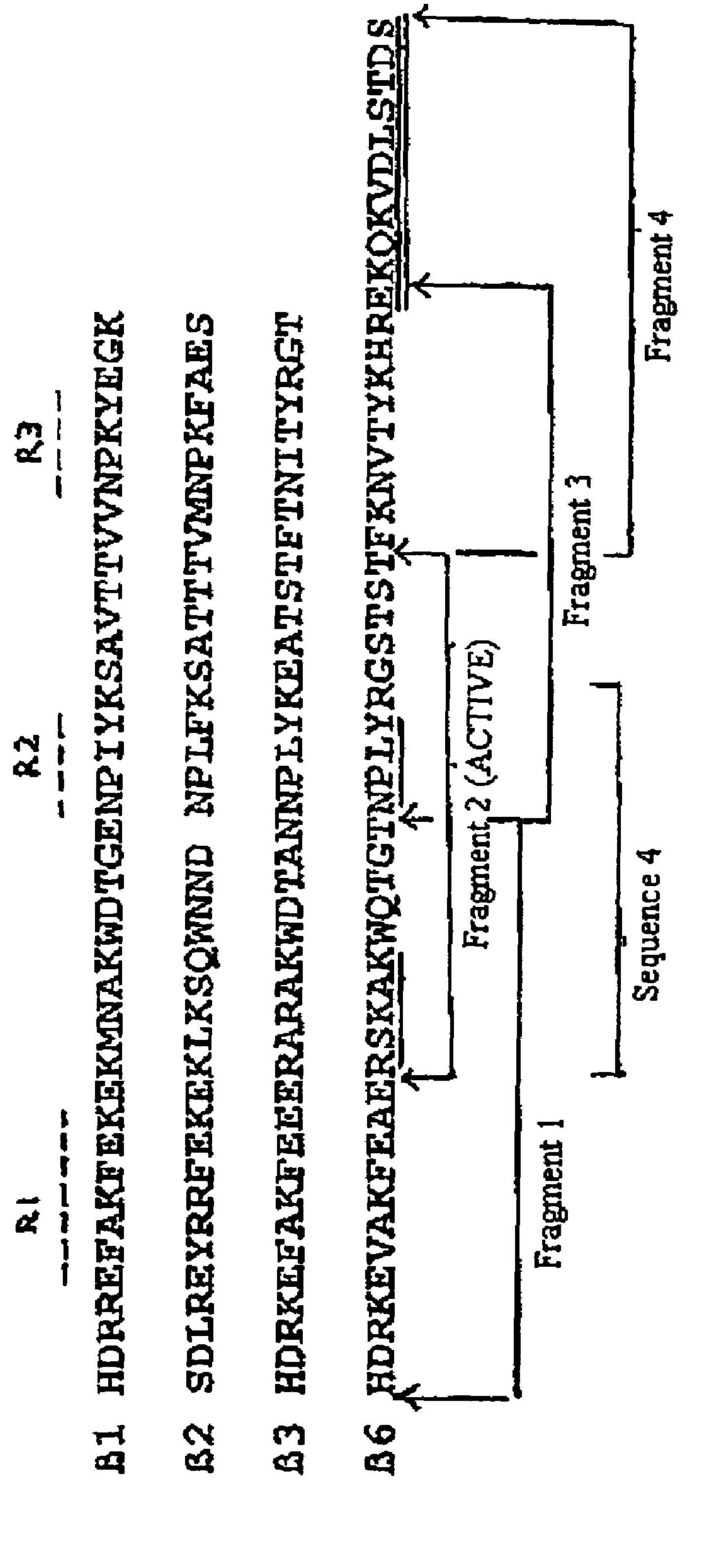
Figure 17:
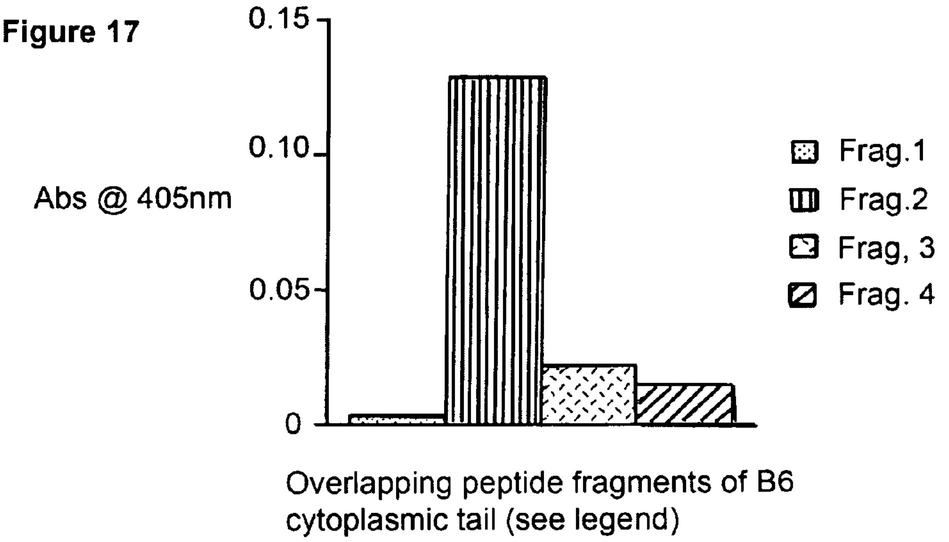
Figure 18:
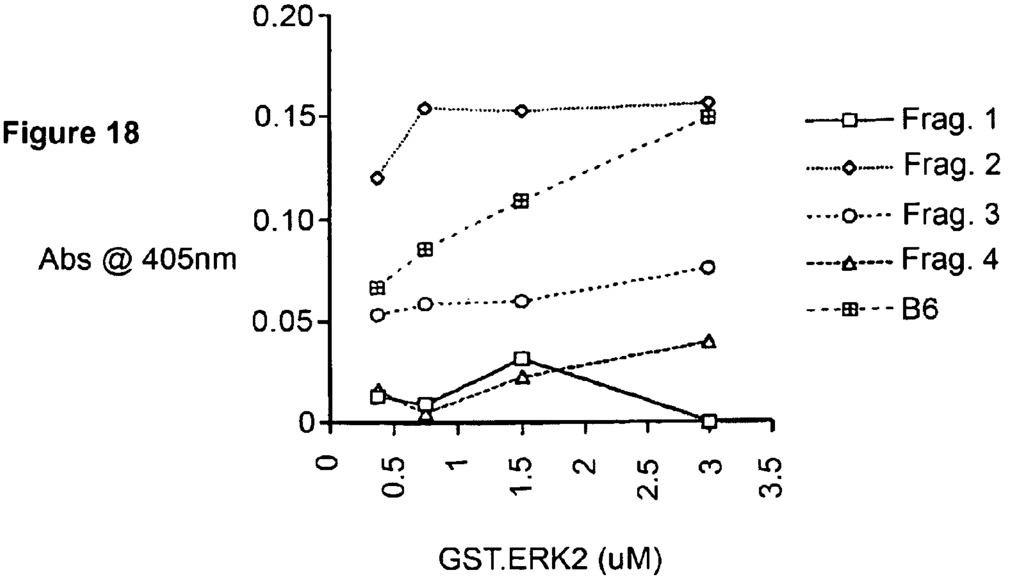
Figure 19:
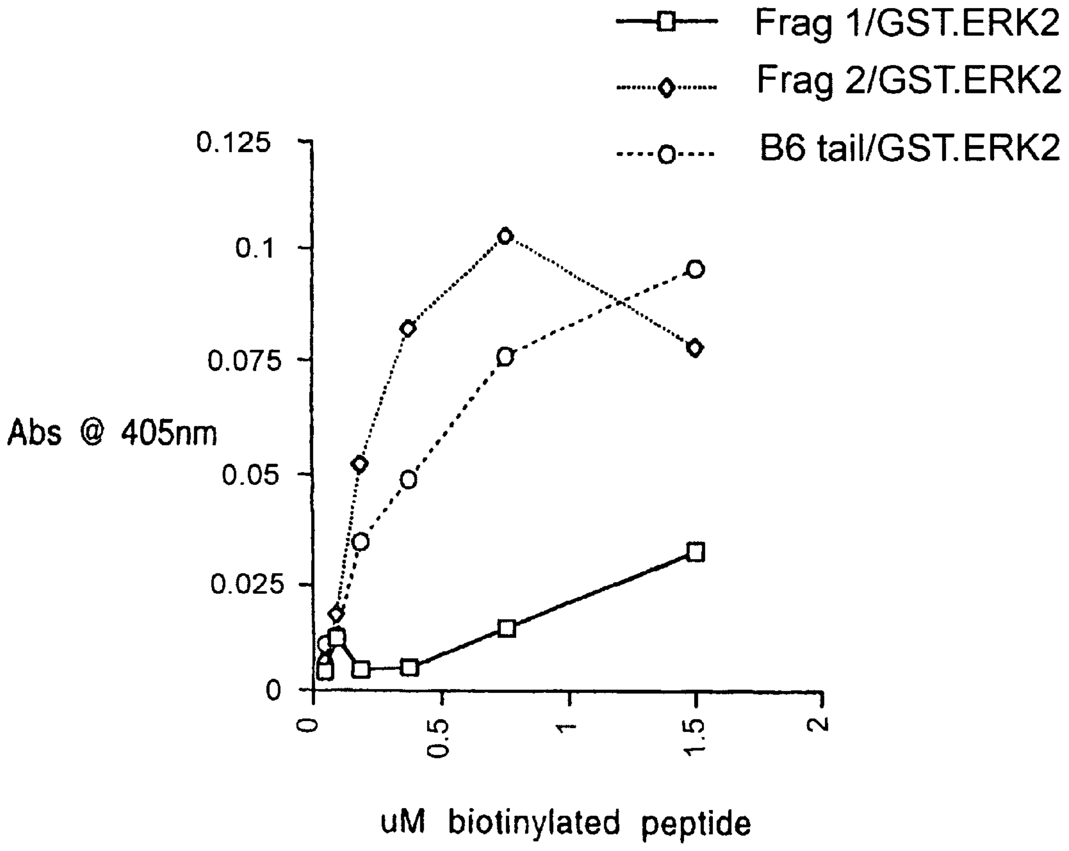
Figure 20:
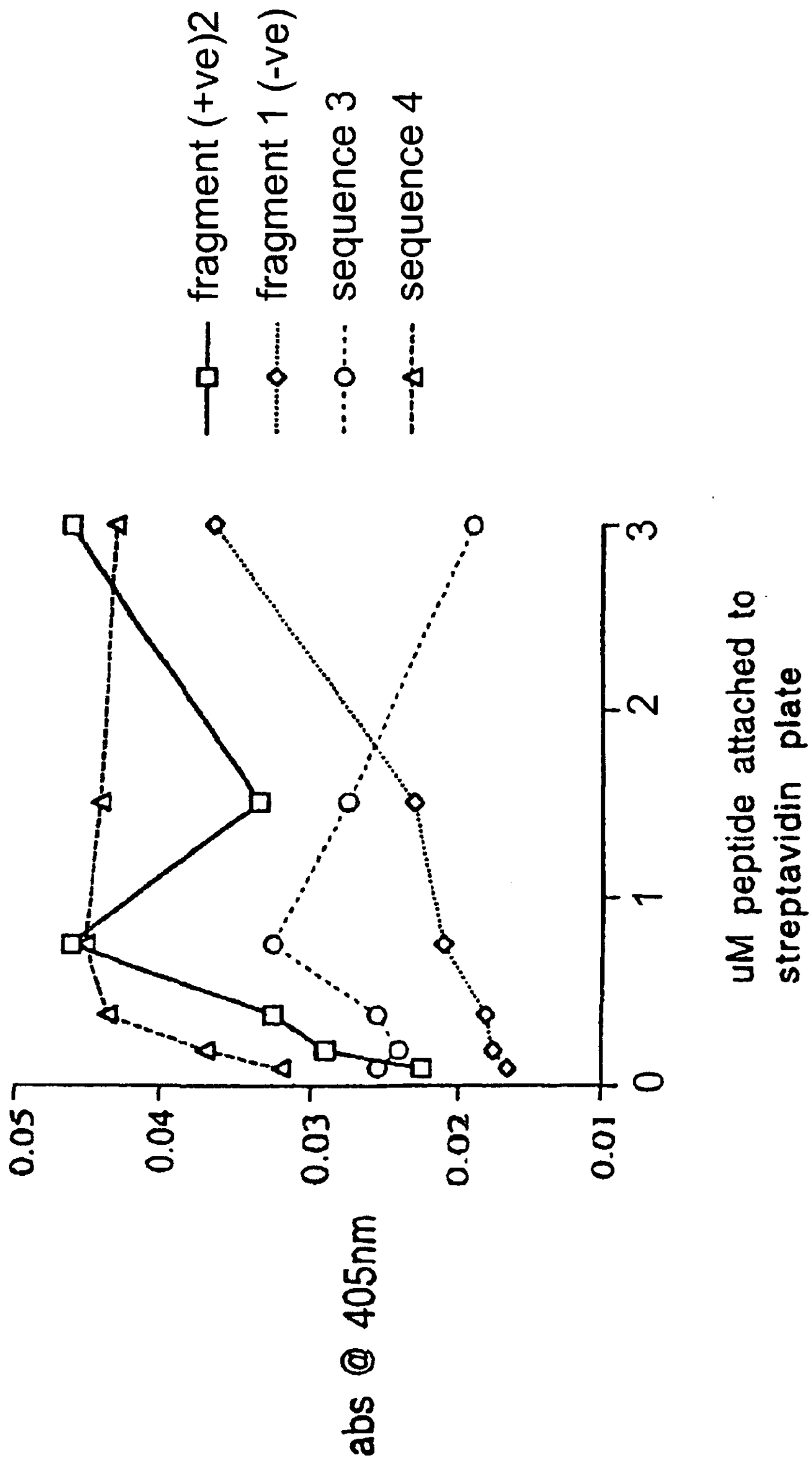

FIG. 16: Shows the amino acid sequence of the cytoplasmic domain of the β6 subunit (SEQ ID NO: 6) as well as the amino acid sequences for the β1 to β3 subunits (SEQ ID NOS: 3-5), respectively;

FIG. 17: Graph showing binding of non-phosphorylated ERK2 (GST.ERK2) to overlapping fragments corresponding to different regions of the cytoplasmic domain of the β6 subunit;

FIG. 18: Graph showing binding of ERK2 (GST.ERK2) to the β6 cytoplasmic domain and the peptide fragments indicated in FIG. 16 over a range of concentrations of ERK2;

FIG. 19: Graph showing binding of ERK2 (GST.ERK2) to the β6 cytoplasmic domain and fragments thereof;

FIG. 20: Graph showing binding of ERK2 (GST.ERK2) to a 15 mer fragment of the β6 cytoplasmic domain and which has the amino acid sequence RSKAKWQTGTNPLYR (SEQ ID NO: 7); and FIG. 21: Shows regions of the cytoplasmic domain of the β6 subunit corresponding to synthesised fragments thereof evaluated for capacity to be bound by ERK2.

Figure 21:
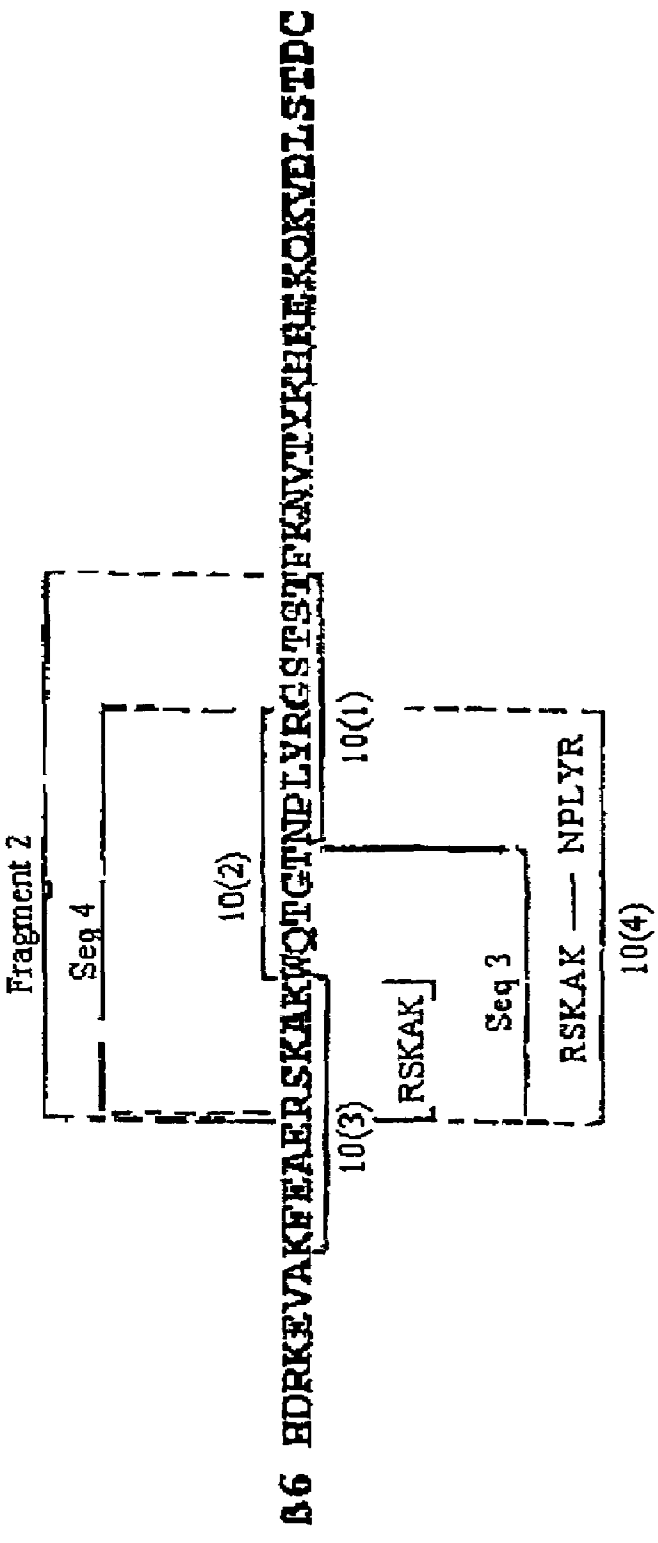
Figure 22:
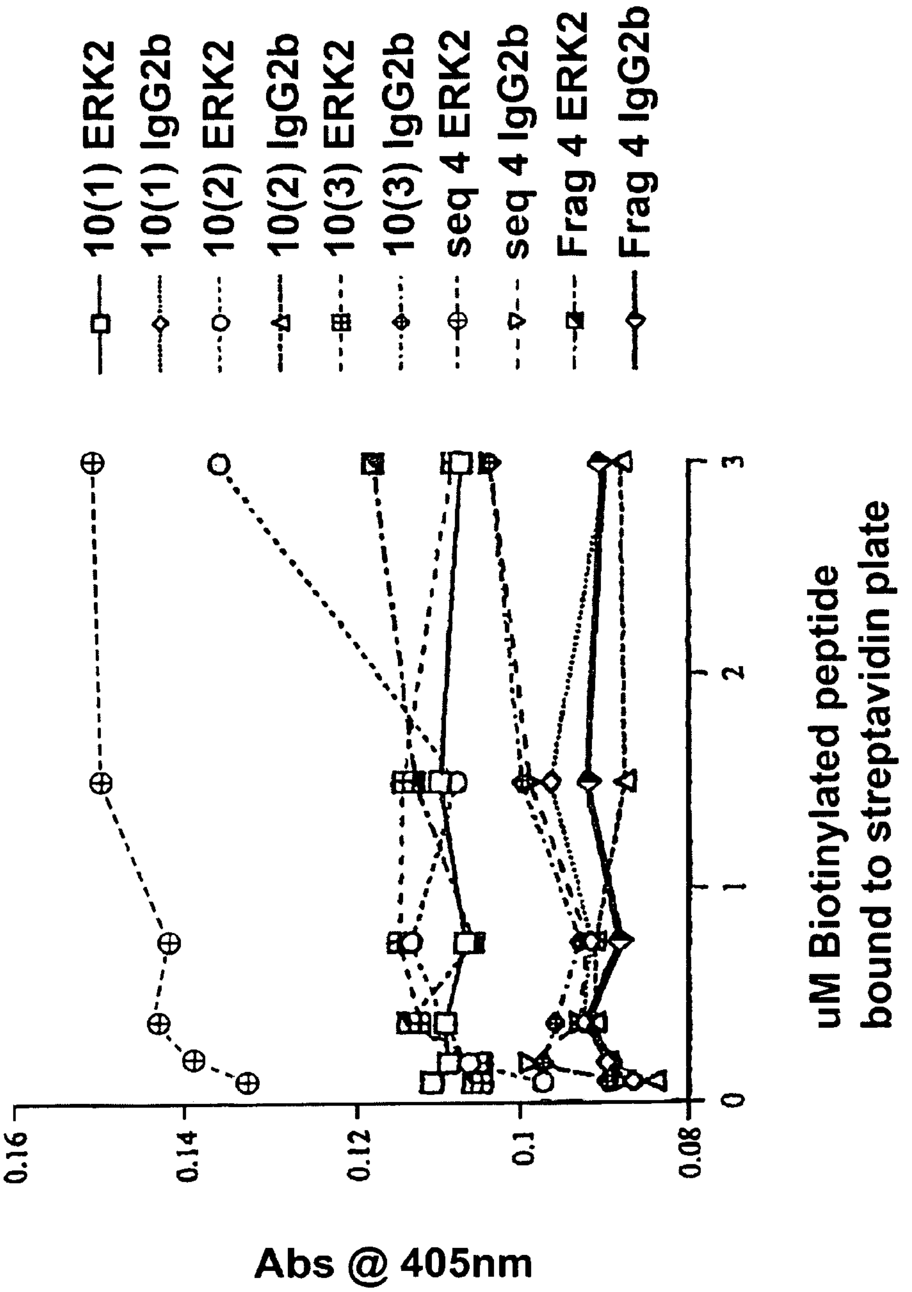

FIG. 22: Graph showing assay results for ERK2 (GST.ERK) binding to synthesised 10 mer fragments identified in FIG. 21.

Figure 23:
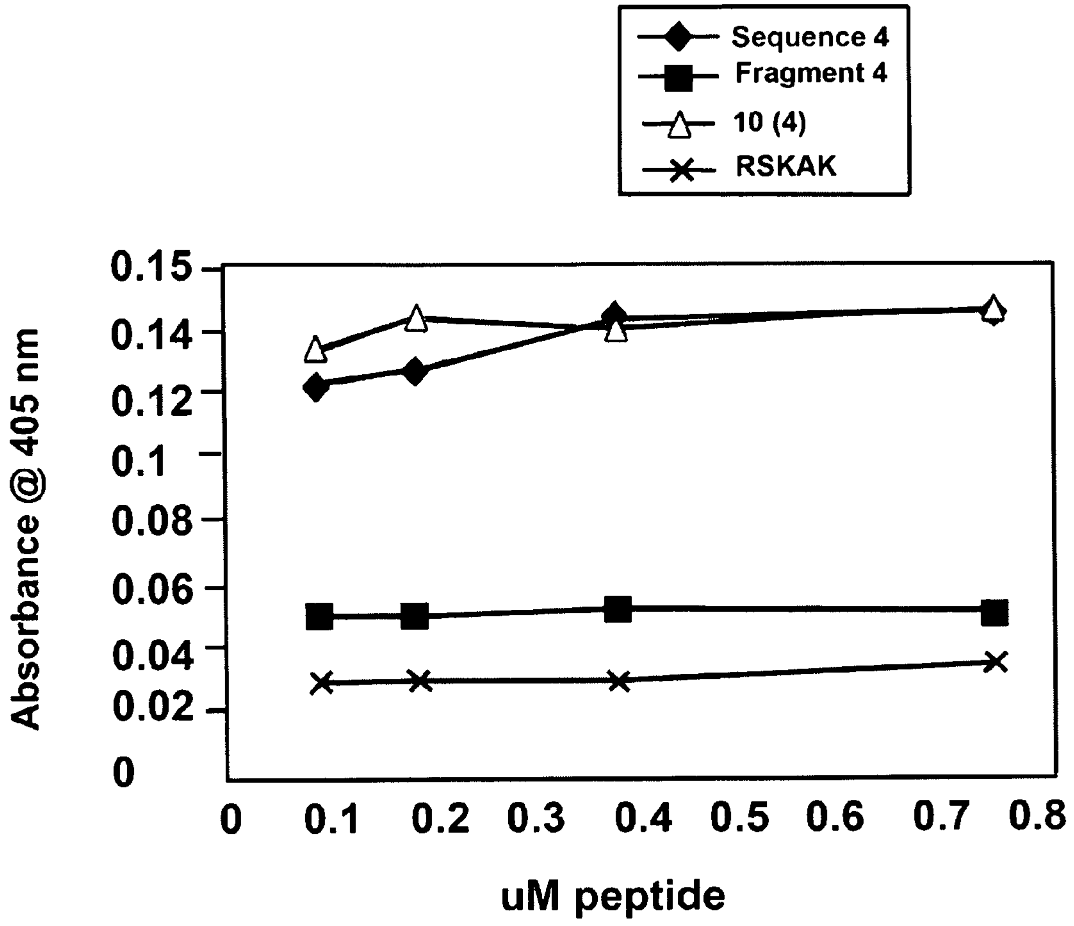

FIG. 23: Graph showing binding of ERK2 (thrombin cleaved) to synthesised peptide having the amino acid sequence RSKAKNPLYR (SEQ ID NO: 8) compared to the 15 mer RSKAKWQTGTNPLYR (SEQ ID NO: 7) fragment of the cytoplasmic domain of the β6 subunit.

Figure 24:
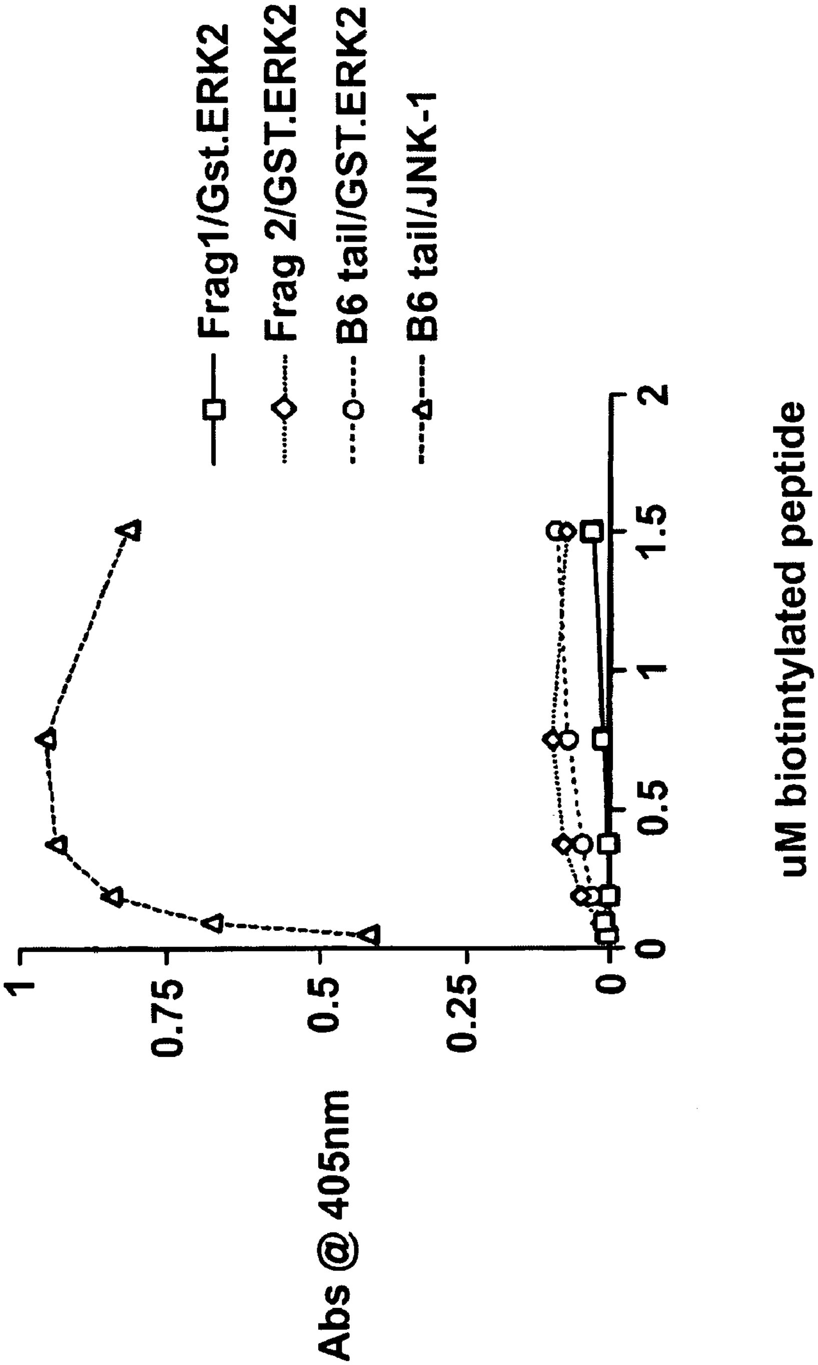

FIG. 24: Graph showing binding of JNK-1 to the β6 cytoplasmic domain.

Figure 25:
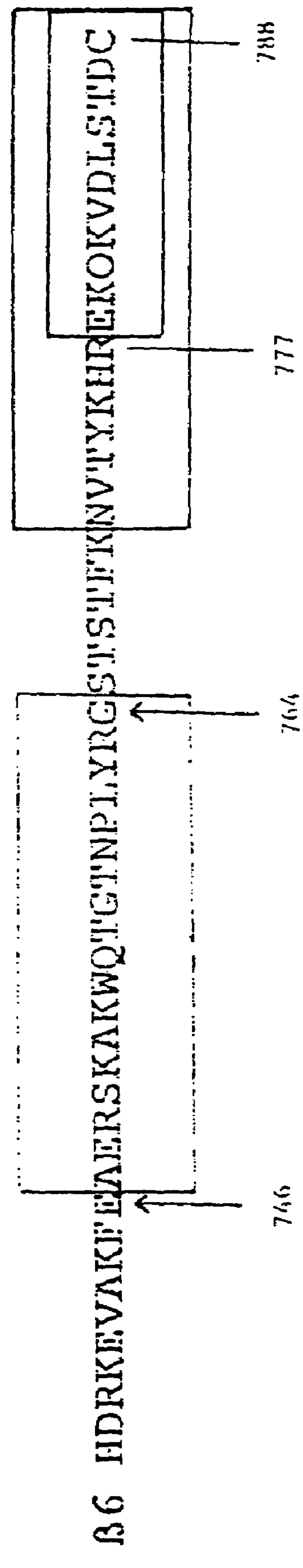

FIG. 25: Location of β6 Δ746-764, β6(770t) and β6(777t) deletions in the cytoplasmic domain of the β6 subunit.

Figure 26:
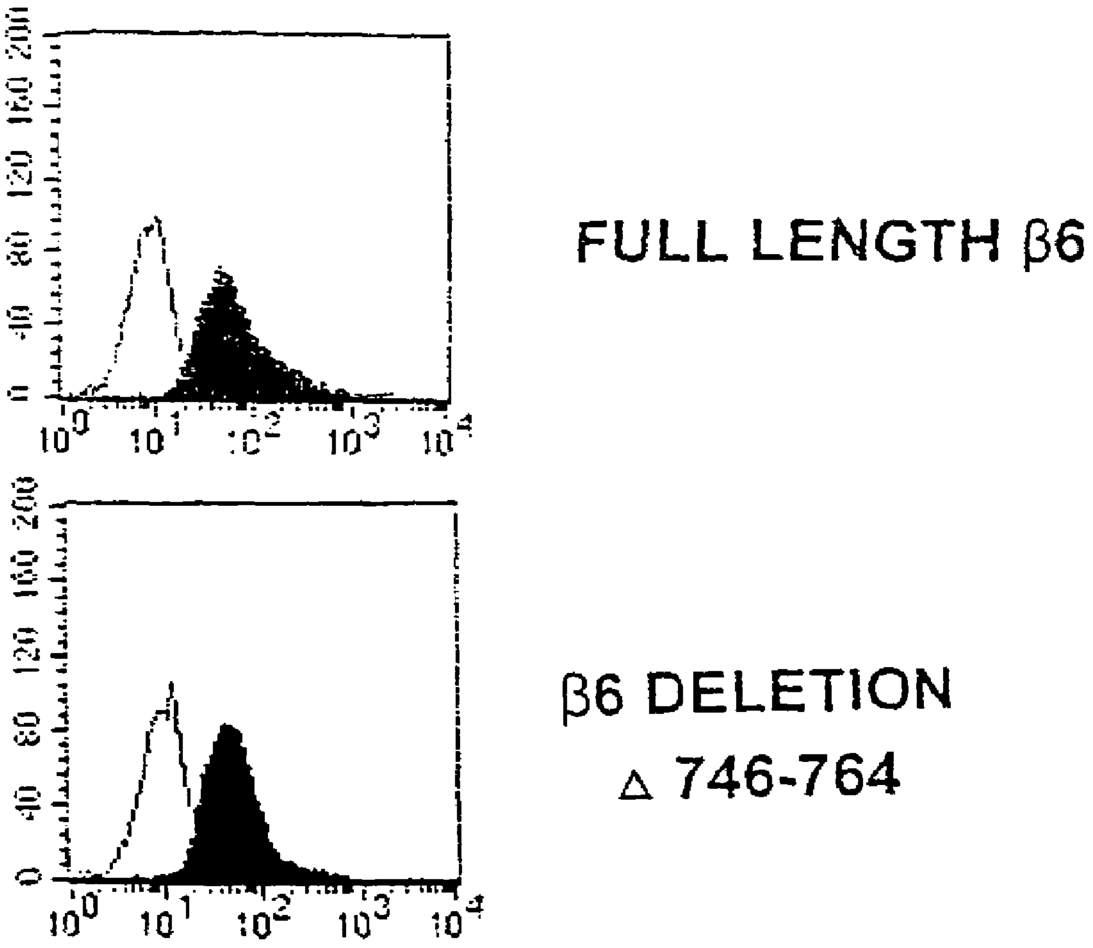

FIG. 26: SW480 cells transfected with wild-type full length coding sequence for β6 or β6 Δ746-764 deletion mutant analysed by FACScan for expression of wild-type or mutant β6. White and black histograms represent cells stained in the absence and presence of the integrin subunit, respectively.

FIGS. 27(A) and 27(B): (A) Western blotting: equal protein loads of cell lyates from SW480 cells expressing wild-type β6 or β6 Δ746-764 deletion mutant. (B) β6 immunoprecipitates (mAb R6G9) from equal protein loads of cell lysates (A) probed with anti-ERK mAb (E10).

Figure 28:
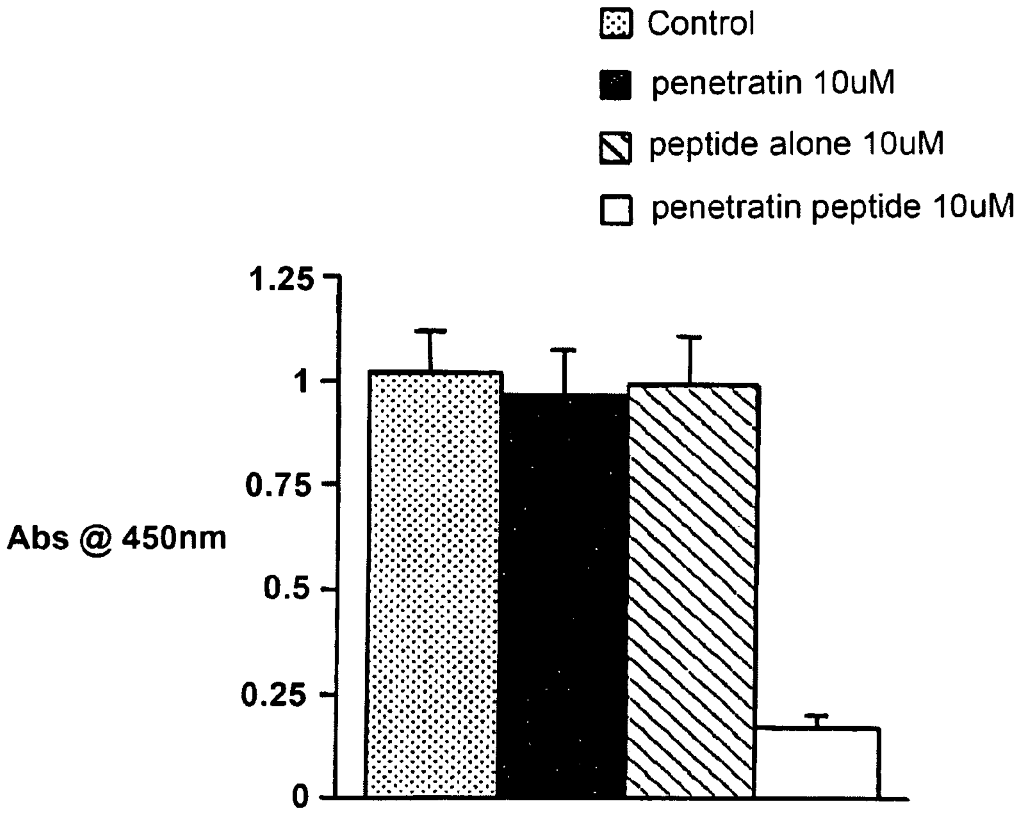

FIG. 28: Proliferation of HT29 colon cancer cells cultured for 48 hours and treated with penetratin, the fragment of β6 cytoplasmic domain having amino acid sequence RSKAKWQTGTNPLYR (SEQ ID NO: 7) alone or the fragment coupled to penetratin for the final 24 hours of the incubation period.

Figure 29:
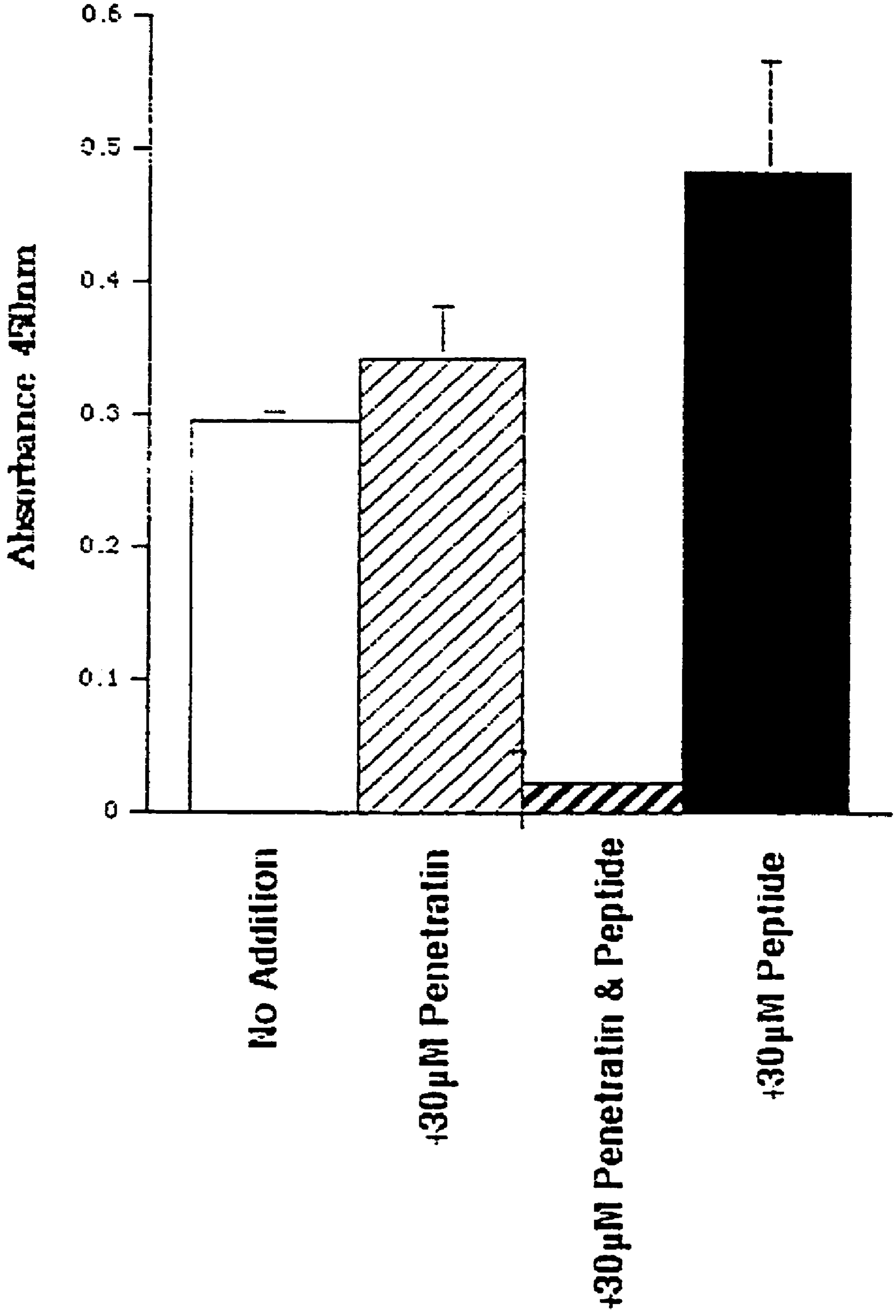

FIG. 29: Proliferation of SW480 cells expressing wild-type β6 cultured on plastic for 48 hours and treated with penetratin, the RSKAKWQTGTNPLYR (SEQ ID NO: 7) peptide alone or the peptide coupled to penetratin for the final 24 hours of the incubation period.

Figure 30:
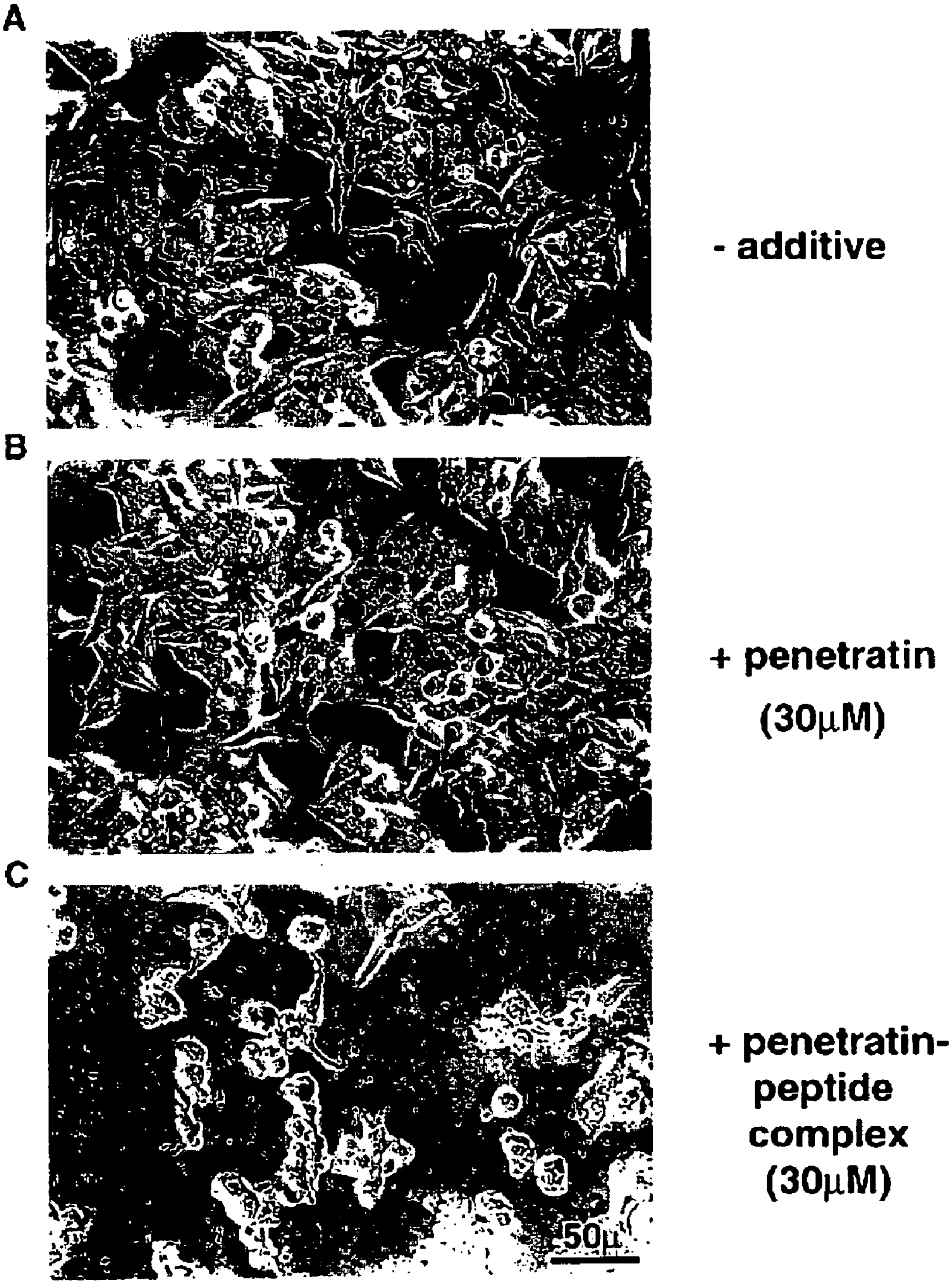

FIGS. 30(A) to 29(C): (A) SW480 cells cultured with control additive for 24 hours; (B) SW480 cells cultured with penetratin for 24 hours; (C) SW480 cells cultured with RSKAKWQTGTNPLYR (SEQ ID NO: 7) bound to penetratin for 24 hours.

Figure 31A:
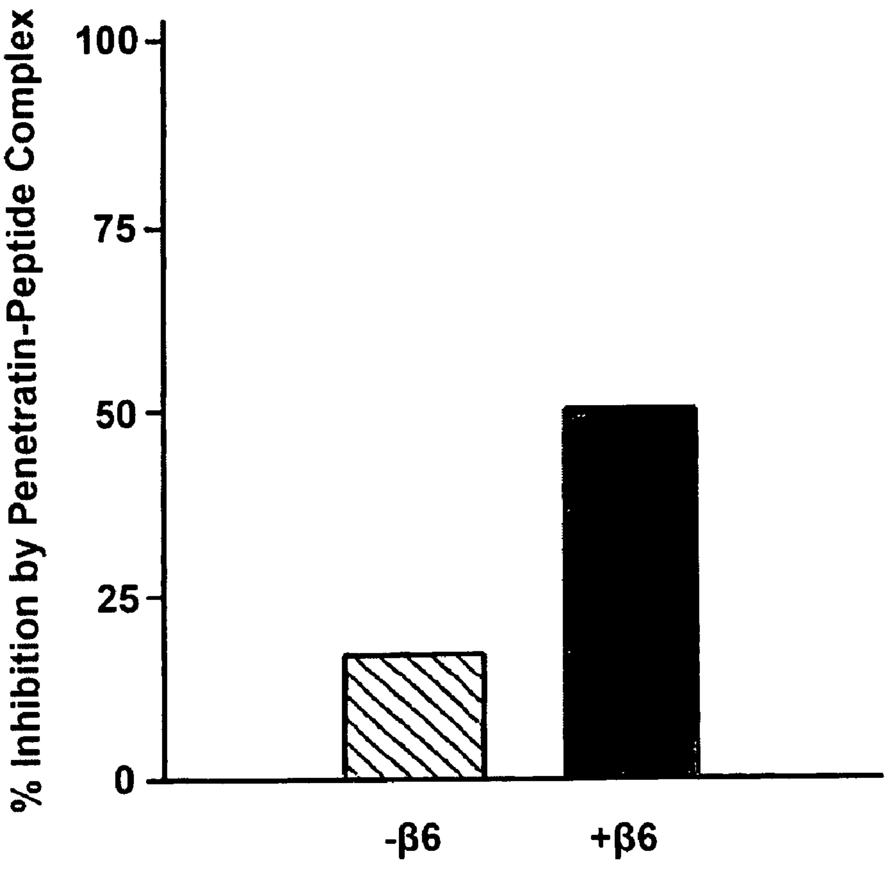
Figure 31B:
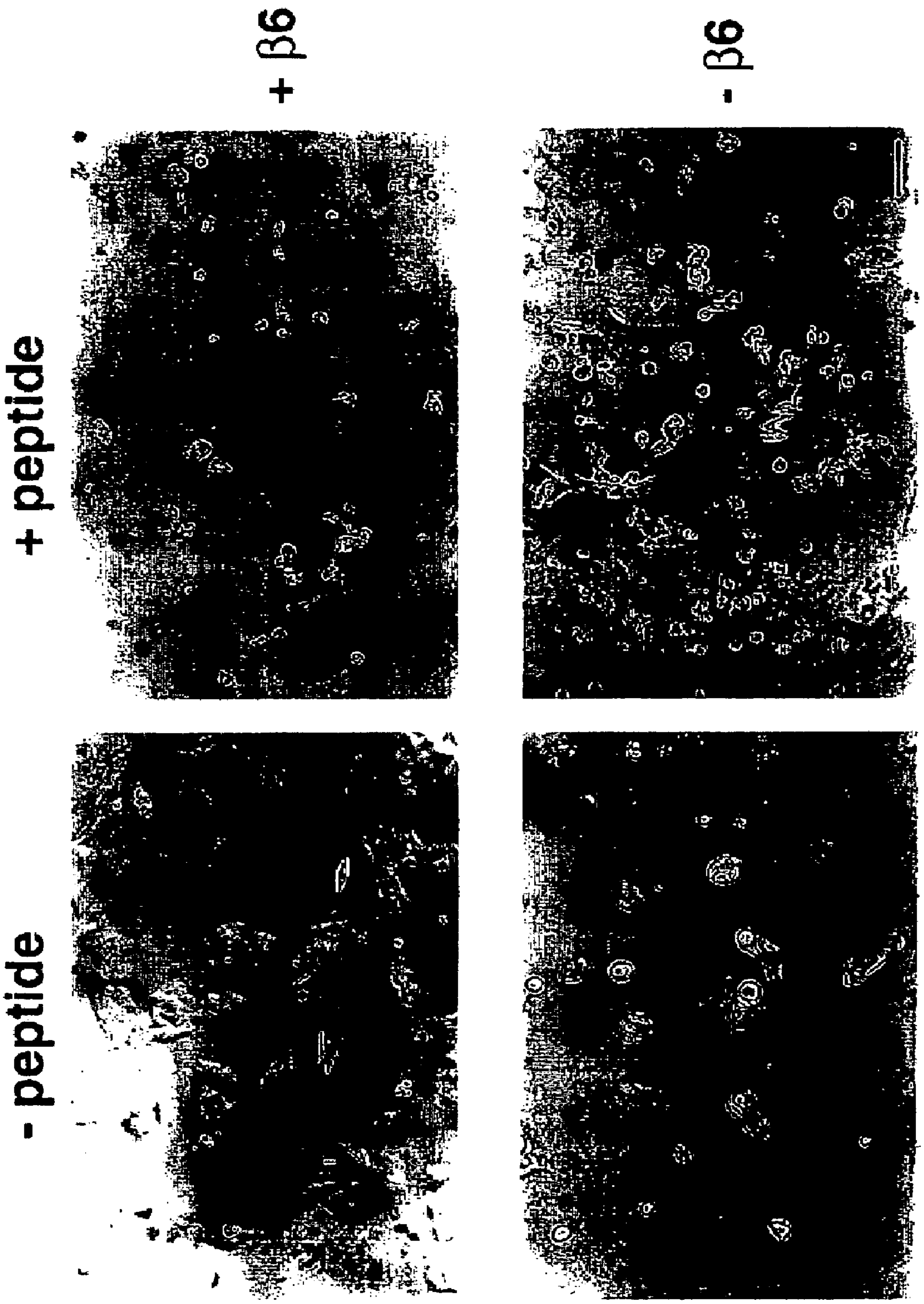

FIGS. 31(A) and 31(B): (A) SW480 mock (−β6) and SW480 β6 transfectants (+β6) cultured in presence of the RSKAKWQTGTNPLYR (SEQ ID NO: 7) peptide coupled to penetratin. (B) Photomicrographs of cells shown in (A) cultured in the presence/absence of the peptide penetratin complex.

Figure 32A:
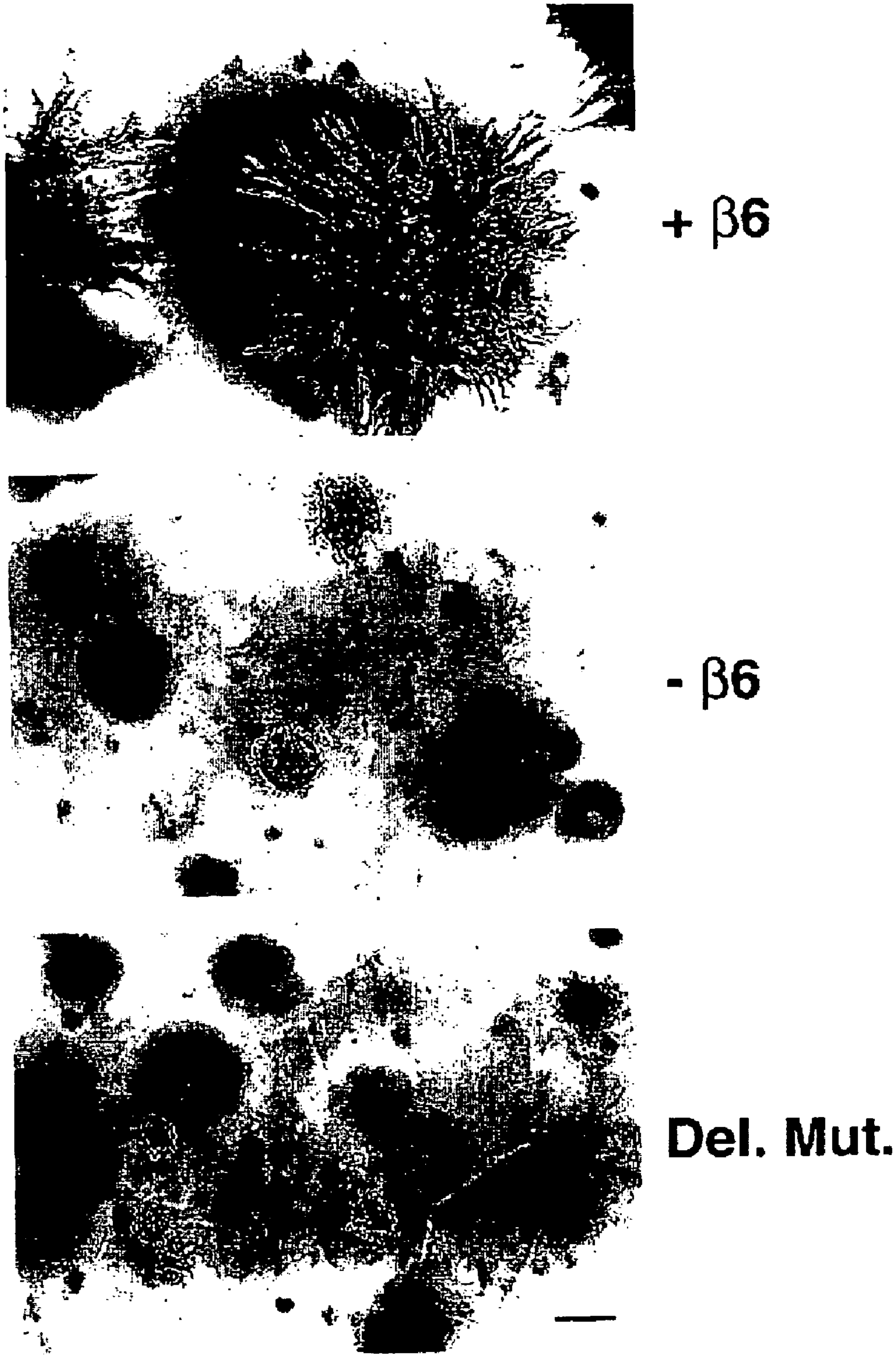
Figure 32B:
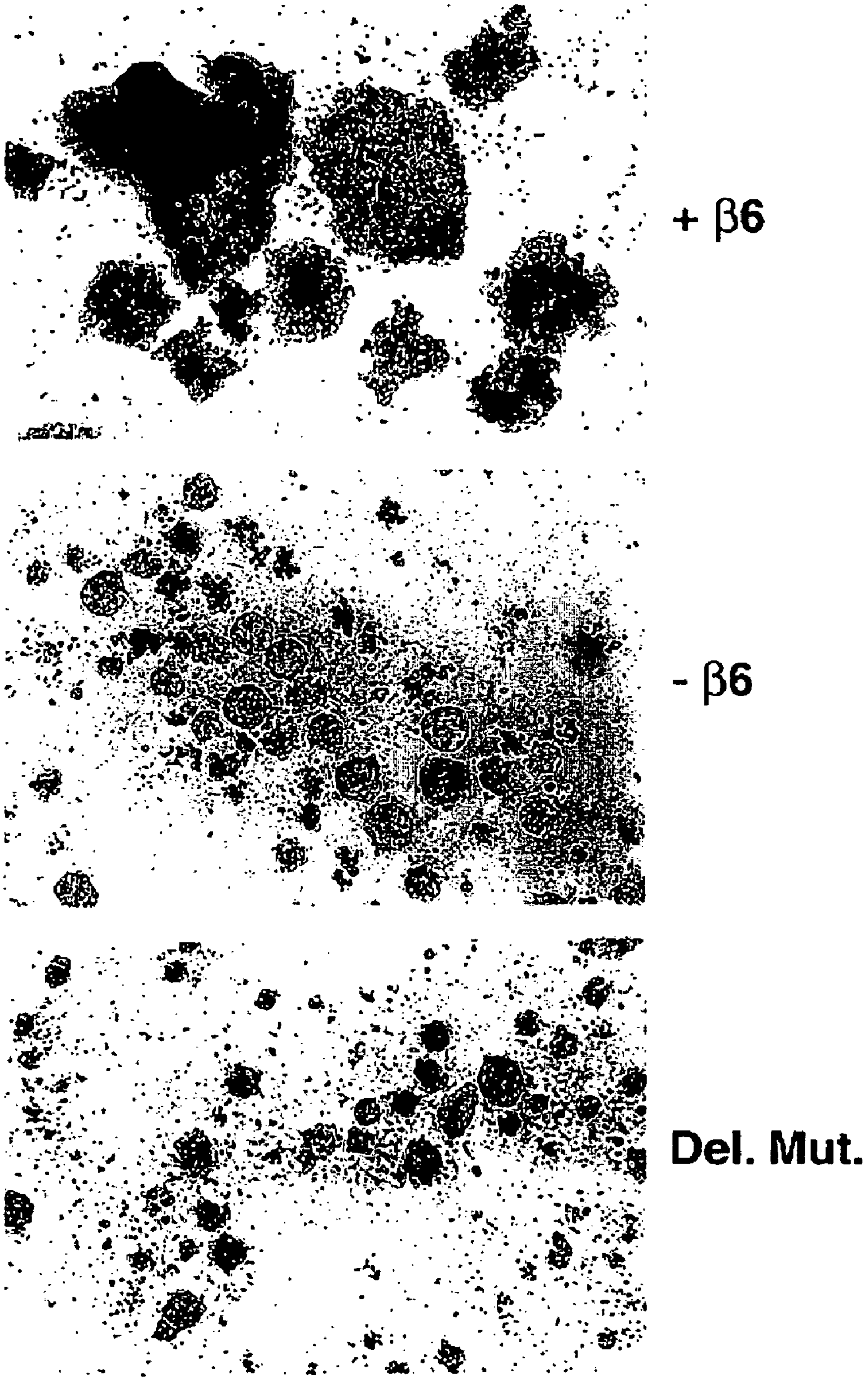
Figure 32C:
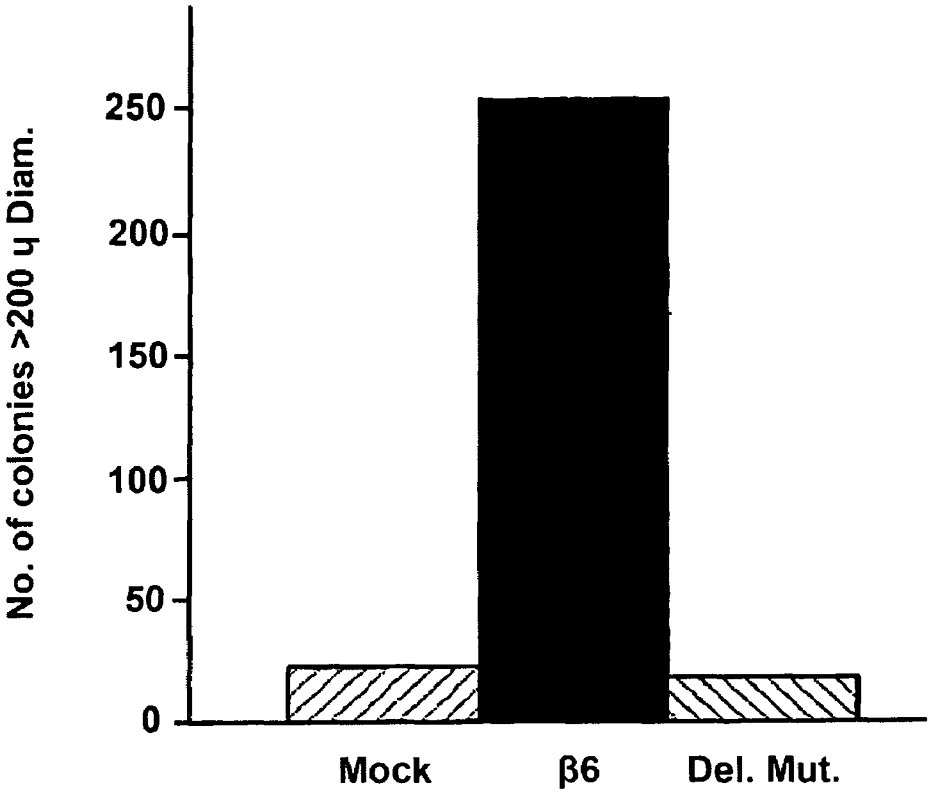

FIGS. 32(A) to 32(C): (A) SW480 cells cultured in a 3-dimensional collagen type I matrix photographed in the gel at the end of 10 days. (B) The SW480 cells following dissolution of the collagen with collagenase. (C) Graph showing numbers of colonies of the SW480 cells having a diameter exceeding 200μ.

Figure 33A:
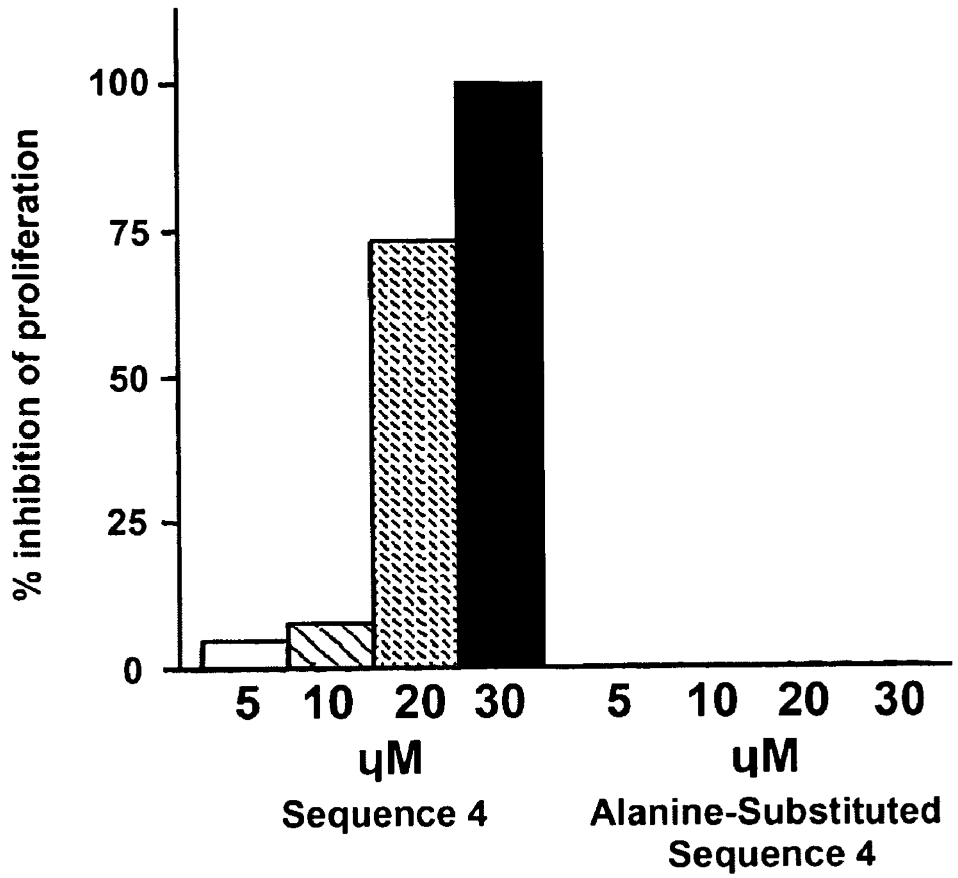
Figure 33B:
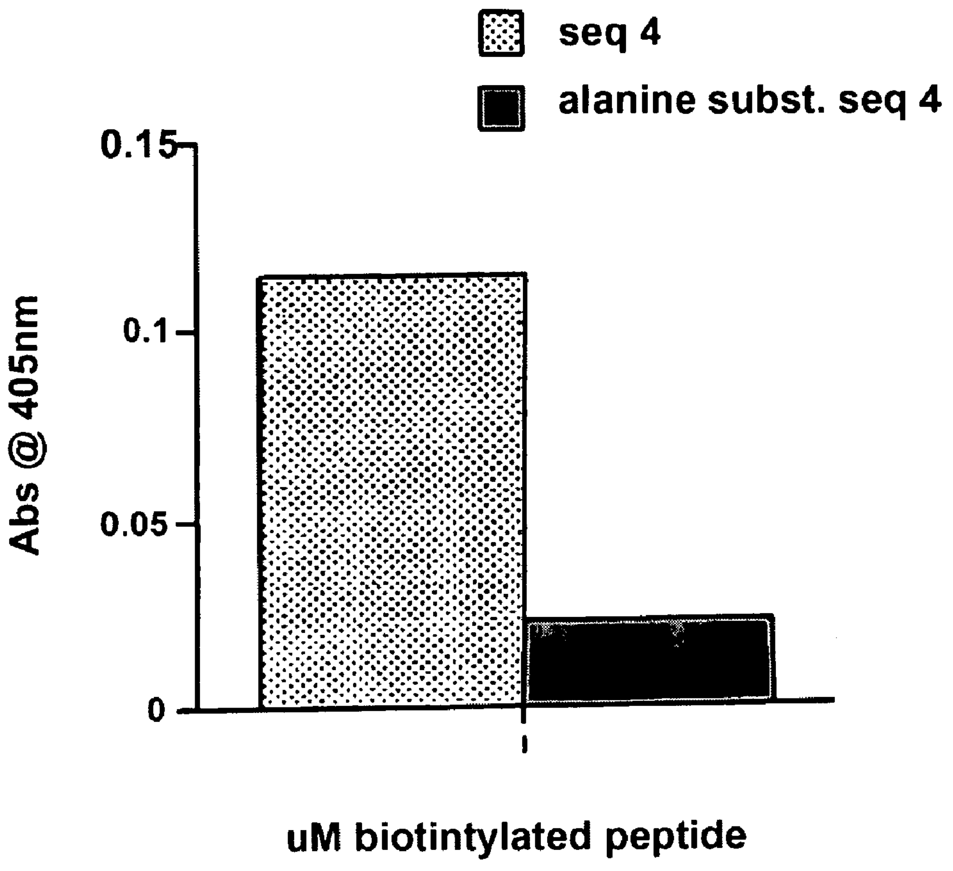

FIGS. 33(A) and 33(B): Graphs showing inhibition of proliferation of SW480 cells expressing full length wild-type β6 in the presence of RSKAKWQTGTNPLYR (SEQ ID NO: 7) peptide bound to penetratin.

Figure 34:
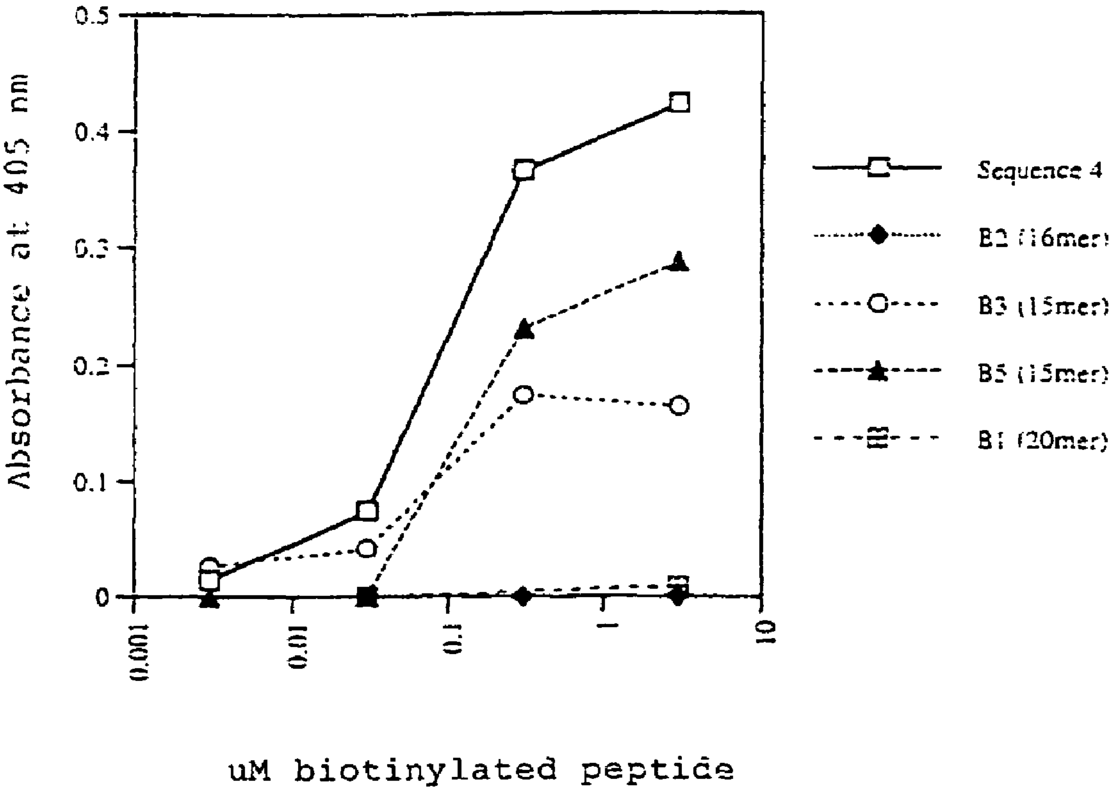

FIG. 34: Graph showing binding of ERK2 to RSKAKWQTGTNPLYR (SEQ ID NO: 7) peptide and peptides corresponding to regions of the cytoplasmic domain of β3 and β5.

Figure 35:
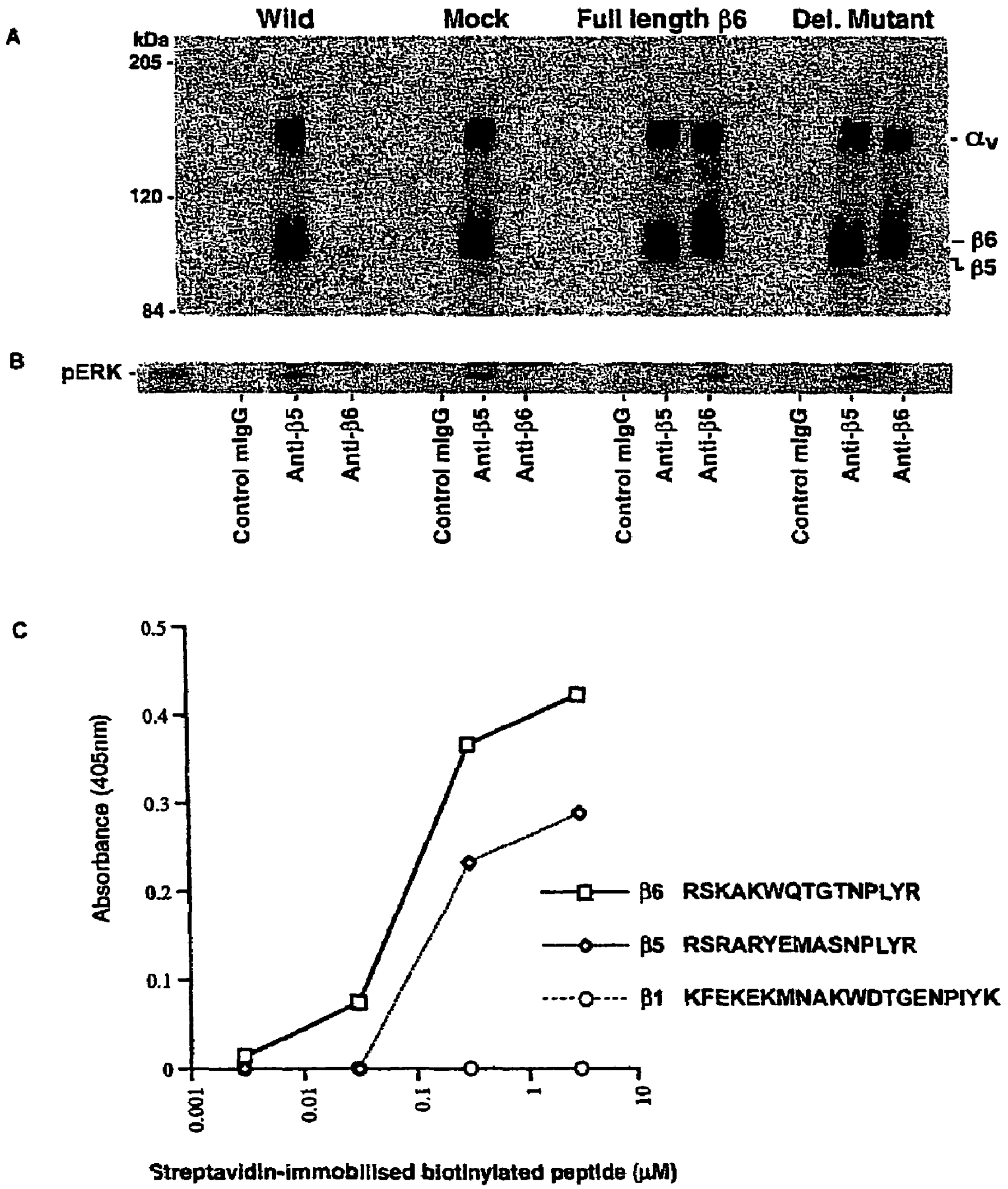

FIGS. 35(A) to 35(C): (A) Immunoprecipitations of β5 and β6 subunits followed by immunoblotting with anti-biotin antibody. αv/β5/β6 bands are shown for the SW480 cell line: wild-type cells, mock transfectants (vector alone) or cells expressing either full length β6 or a Δ746-764 deletion mutant. (B) Indentical amounts of precipitated proteins shown in (A) were immunoblotted with anti-ERK mAb (E10) against phosphorylated ERK1/2. Purified phosphorylated ERK2 is shown in the left hand lane. (C) Comparative binding of ERK2 (1 μm) to synthetic peptides comprising either RSKAKWQTGTNPLYR (SEQ ID NO: 7) or peptide sequences derived from β5 and β1 cytoplasmic domains that correspond to the binding domain on β6 for ERK.

Figure 36:
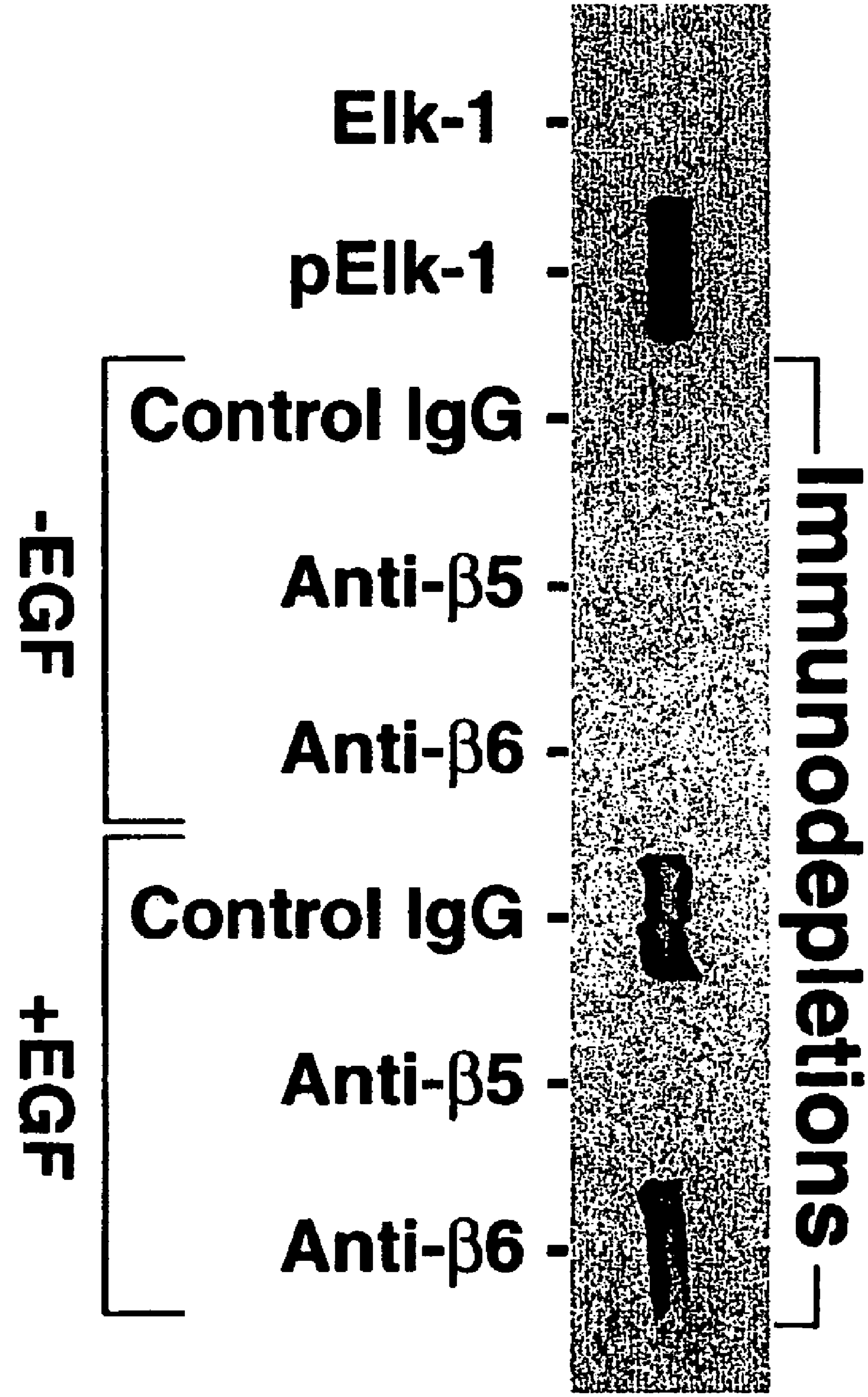

FIG. 36: In vitro phosphorylation of GST-Elk-1 by immunoprecipitated ERK from cell lysates prepared from human umbilical vein endothelial cells (HUVECs) cultured in the absence/presence of epidermal growth factor (EGF) after a 24 hour culture period in serum-free and growth factor free medium.

Figure 37:
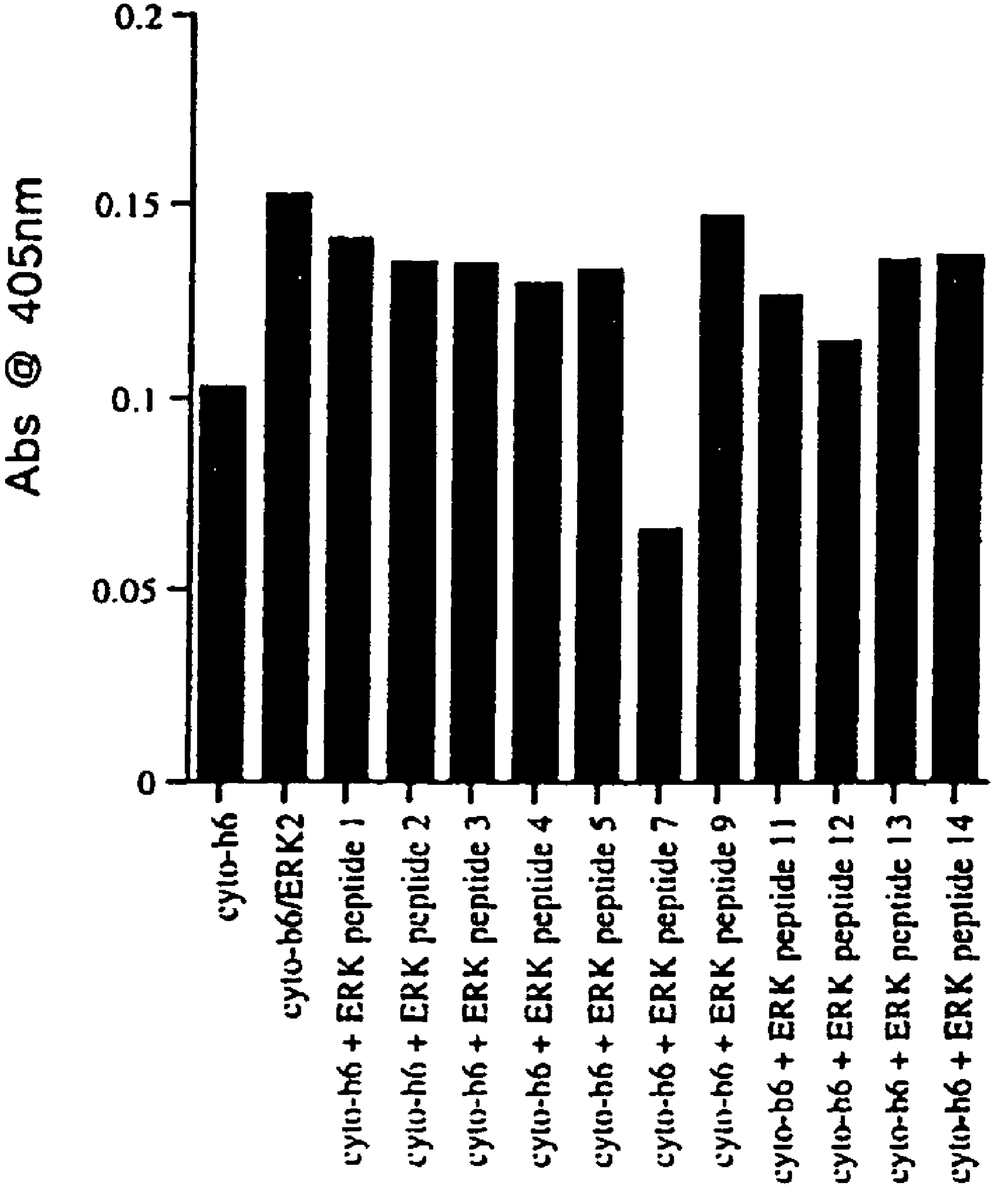
Figure 38:
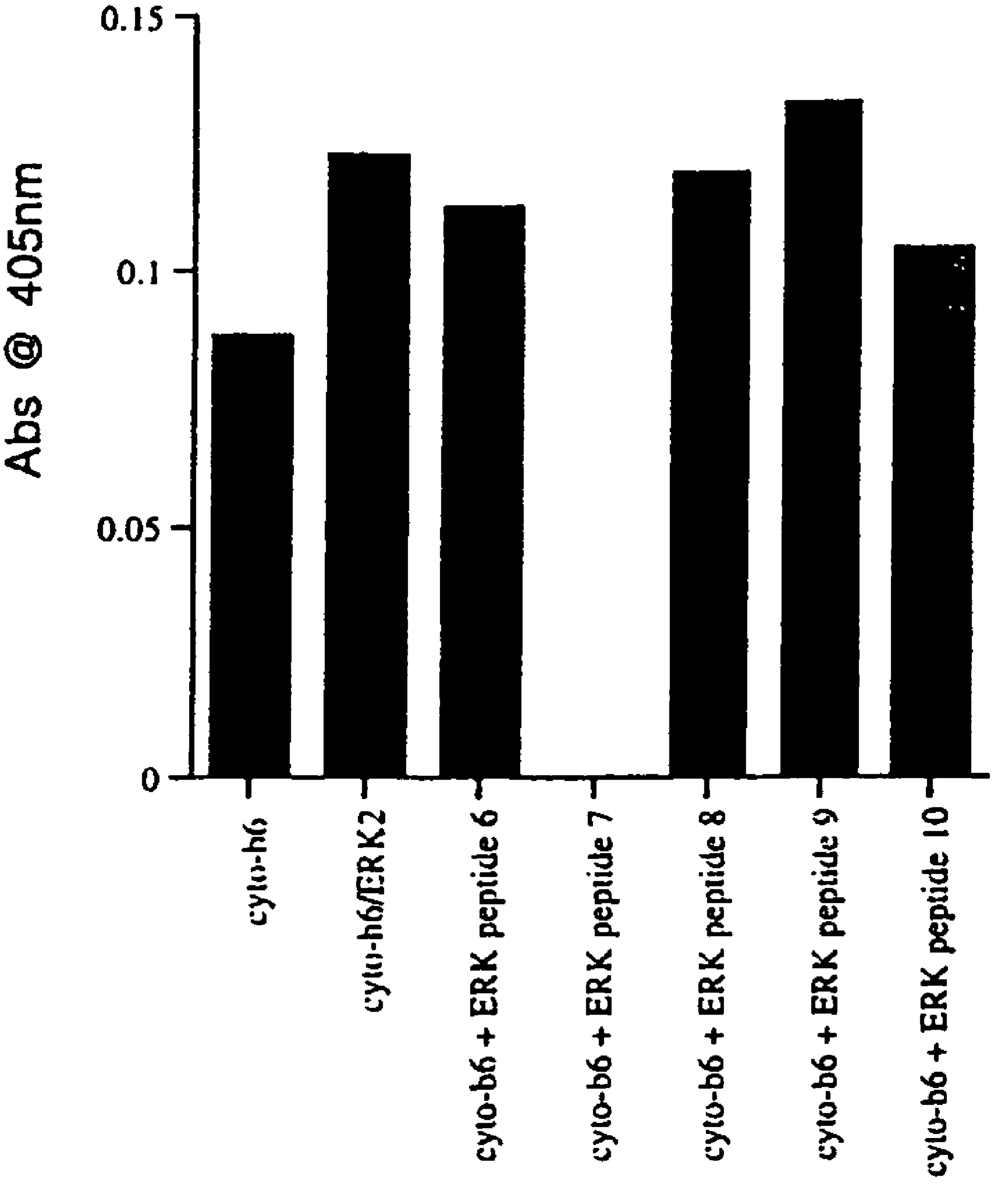

FIGS. 37 and 38: Overlapping peptides derived from ERK2 sequence tested for ability to inhibit the β6-ERK2 interaction.

Figure 39:
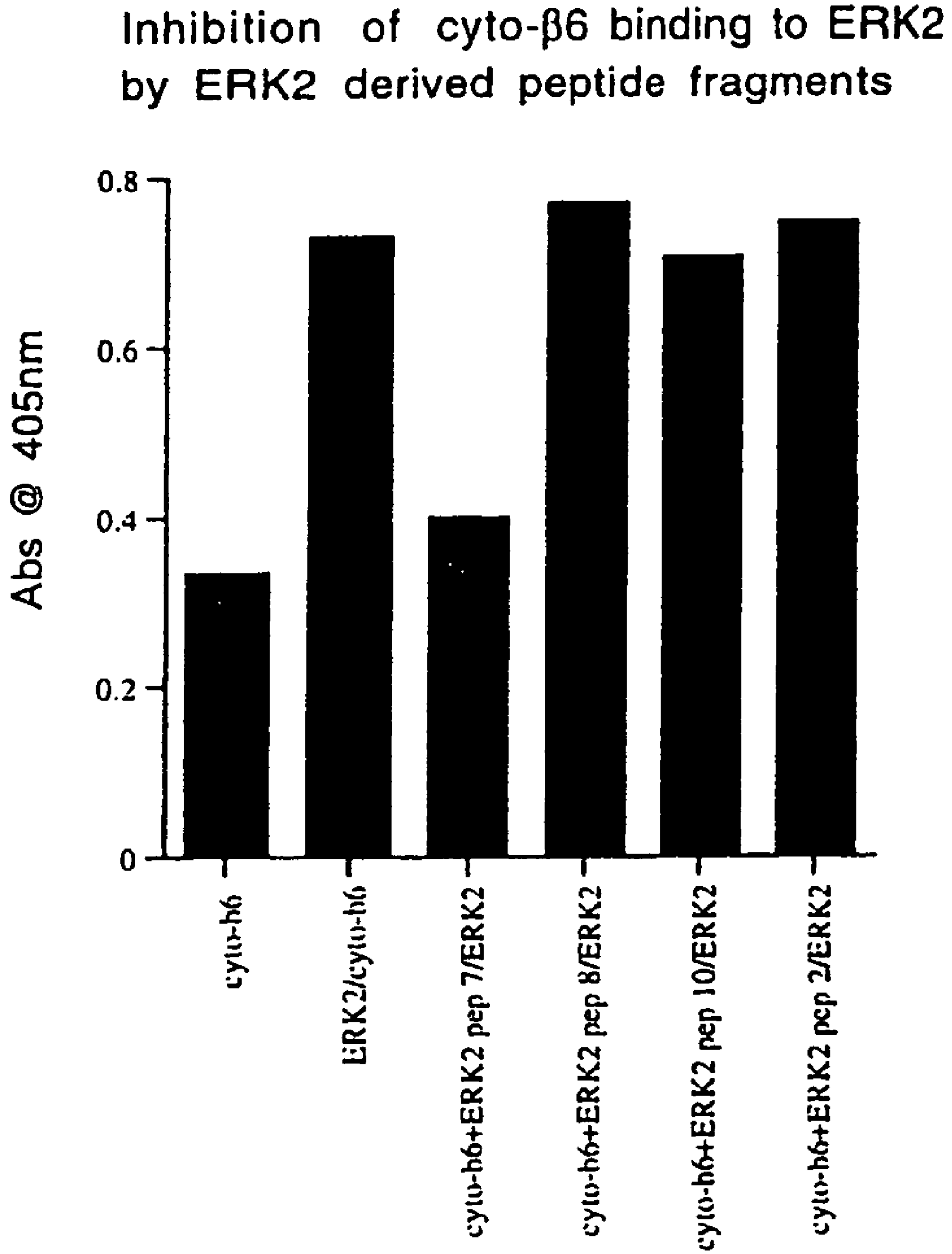

FIG. 39: Inhibition of β6-ERK2 interaction using ERK2 peptide HRDLKPSNLLLNTTCDLK (SEQ ID NO: 9) (0.25 μm) and β6 cytoplasmic tail peptide.

FIGS. 40(A) to 40(D): Illustrate a dose-dependent wound repair process for peptide-agonist complexed with penetratin as a delivery vehicle.

FIG. 41: Nucleotide and amino acid sequence for ERK2 (SEQ ID NOS: 11 and 10 respectively).

DETAILED DESCRIPTION OF PREFERRED EMBODIMENTS OF THE PRESENT INVENTION

The distribution of β6 integrin subunit within various tissues has been assessed by both in situ hybridisation and immunostaining and reported in the art. For instance, β6 mRNA in adult primate tissues was detected only in epithelial cells and at very low or undetectable levels in most normal tissues (Breuss et al, 1993). High-level expression of β6 has been observed in secretory endometrial glands while low-level expression was detected in the ductal epithelia of salivary gland, mammary gland and epididymis, in gall and urinary bladder, and in the digestive tract. Immunostaining data has also shown that β6 expression is restricted to epithelia and is up-regulated in parallel with morphogenetic events, tumourigenesis and epithelial repair (Breuss et al, 1993; 1995). During development of the kidney, lung and skin, β6 is expressed by specific types of epithelial cells, whereas it is mostly undetectable in normal adult kidney, lung and skin. In contrast, high level expression of β6 has been observed in several types of carcinoma. For example, β6 is almost invariably neo-expressed in squamous cell carcinomas derived from the oral mucosa, and often focally localised at the infiltrating edges of tumour cell islands (Breuss et al, 1995; Thomas et al, 1997). Moreover, expression of the β6 subunit has been observed in renal cell carcinoma and testicular tumour cell lines (Takiuchi et al, 1994) and 50% of lung cancers have been shown to express this subunit (Smythe et al, 1995).

Recent studies have shown that αvβ6 is a major fibronectin-binding receptor in colorectal cancer (Agrez et al, 1996). Moreover, normal colonic epithelium from cancer patients does not express αvβ6 in immunostaining studies, and as with squamous cell carcinomas from the oral mucosa (Thomas et al, 1997) maximal β6 expression in colon cancer has been observed at the invading edges of tumour cell islands (Agrez et al, 1996). Importantly, heterologous expression of the β6 subunit in colon cancer cells lacking constitutive expression of this receptor has been shown to stimulate tumour cell proliferation in vitro and tumour growth in athymic immune-deficient mice, and this growth-promoting effect is mediated through the 11 amino acid C-terminal cytoplasmic extension unique to the β6 subunit (Agrez et al, 1994). These findings suggest that one mechanism of the enhanced growth effect involves induced secretion of matrix-degrading enzymes as has been previously suggested for invasive melanoma cells. Support for this arises from findings that the proliferative capacity of colon cancer cells within 3-dimensional collagen matrices is inversely related to the density of the extracellular matrix (Agrez, 1989), and the observation that induced expression of αVβ6 in colon cancer cells markedly enhances gelatinase B secretion (Agrez et al, 1999).

Indeed, the β6 subunit is widely observed in cancers of various origins (Breuss et al, 1995). As described above, β6 is detected in at least 50% of bowel cancer tumours. Others have reported its presence in oropharyngeal cancers where it is also present and strongly expressed in the invading margins of the cancer cell islands as is commonly found in bowel cancer. In the oropharyngeal mucosa, no β6 is observed in the normal lining cells of the mouth but in both primary and metastatic tumours from the oropharyngeal mucosa, strong β6 expression is seen which does not correlate with degree of differentiation and in particular, is restricted to the basal layer of epithelial cells. In colon cancer, β6 expression is similarly maximal at the advancing edges of tumour cell islands (Agrez et al, 1996).

Hence, modulation of MAP kinase interaction with the β6 subunit in epithelial cells is of interest in the prophylaxis or treatment of cancer of the lip, tongue, salivary glands, gums, floor and other areas of the mouth, oropharynx, nasopharynx, hypopharynx and other oral cavities, oesophagus, stomach, small intestine, duodenum, colon, rectum, gallbladder, pancreas, larynx, trachea, bronchus, lung, female and male breast, uterus, cervix, ovary, vagina, vulva, prostate, testes, penis, bladder, kidney, thyroid and skin.

In terms of prophylactic use in relation to cancer, modulation of the MAP kinase β6 interaction and specifically down regulation of the interaction may find application in protecting against ultraviolet-induced skin cancer, lung cancer in smokers, cancer of the gut where polyps are present as in polyposis coli or other inheritable disease where a pre-disposition to the development of polyps exists, breast cancer in high risk patients with a familial history of breast cancer or otherwise identified as carrying known mutations of the breast cancer susceptibility gene BRCA1 or BRCA2 associated with breast cancer, transitional cell cancers arising from bladder papillomas, and cancer of the cervix in individuals deemed to be at high risk.

Expression of β6 is also up-regulated in migrating keratinocytes at the wound edge during experimental epidermal wound healing. αvβ6 is not expressed in normal epithelium (Jones et al, 1997). However, following experimental wounding, αv appears to switch its heterodimeric association from β5 to β6 subunit during re-epithelialisation. At day 3 after wounding, β6 is absent but then appears around the perimeter of the basal cells of the migrating epidermis (Clark et al, 1996). By day 14 after wounding, when re-epithelialisation is complete, all suprabasalar cells overlying the wound express β6 but not β5.

In human mucosal wounds, maximal expression of β6 has been observed relatively late when epithelial sheets are fused and granulation tissue is present (Haapasalmi et al, 1996). Furthermore, those investigators observed maximal expression of tenascin with αvβ6 expression. Interestingly, freshly isolated keratinocytes have not been found to express β6 but begin to express this after subculturing (Haapasalmi et al, 1996). Moreover, TGF-β1 has been shown to induce the de novo expression of αvβ6 at the cell surface on keratinocytes (Zambruno et al, 1995). This is particularly relevant in view of the recent observation that αvβ6 binds and activates latent TGF-β1 which may be a means of locally regulating TGF-β1 function in vivo during tissue response to injury (Munger et al, 1999).

In contrast to persistent αvβ6 expression observed in colon cancer cells, new expression of αvβ6 in migrating keratinocytes is down-regulated to undetectable levels once re-epithelialisation is complete (Happasalami et al, 1996; Cass et al, 1998).

While in the normal unwounded skin, just as in other normal epithelia, αvβ6 expression is absent indicating that this MAP kinase activation pathway is normally suppressed. However, alterations in cell shape trigger biochemical signalling by MAP kinases in human keratinocytes and it is likely that alterations of skin mechanics in vivo during wound formation and healing trigger physiological responses via the MAP kinase pathway (Krippenberg et al, 2000). In addition, gelatinase B secretion by keratinocytes which facilitates the process of cell migration during normal re-epithelialisation is MAP kinase-dependent (McCawley et al, 1999).

As outlined above, MAP kinases behave as a convergence point for diverse receptor-initiated signalling events at the plasma membrane which regulate cell proliferation, differentiation, migration and invasion. In particular, extracellular signal-regulated kinases (ERKs) become activated upon integrin ligation and, thereby, regulate cell migration possibly by initiating matrix degrading enzyme secretion (Klemke et al, 1997) such as gelatinase B.

Gelatinase B production has been shown to be dependent on endogenous ERK signalling in growth factor-stimulated human kertinocytes (McCawley et al, 1999; Zeigler et all, 1999). Aside from integrins, growth factors such as foetal calf serum or epidermal growth factor (EGF) have been shown to stimulate ERK activity via the Ras-Raf-Mek-MAPk cascade resulting in directed cell migration through a porous membrane (Giehl et al, 2000).

There is also abundant data indicating that the MAP kinase cascade plays a major role in alterations of cell shape and migration for a range of normal cell types. For example, the MAP kinase signalling pathway has been shown to mediate neurite outgrowth by cerebellar neurons (Schmid et al, 2000) implying a role for MAP kinase in nerve repair, while growth factor-induced migration of endothelial cells has been shown to be dependant on MAP kinase signalling and this dependency for new blood vessel formation (angiogenesis) on sustained ERK activity is regulated by the ligation state of both growth factor receptors and integrins (Eliceiri et al, 1998). In addition, ERK activation has been demonstrated to be essential for up-regulation of vascular endothelial growth factor (VEGF) in other cell types (Jung et al, 1999), and induction of endothelial tube formation by human umbilical vein endothelial cells (HUVECs) dispersed within a 3-dimensional collagen gel has been shown to be dependent on MAP kinase activation (Ilan et al, 1998).

Growth factors and their receptors are also known to play important roles in tissue repair and ulcer healing. For example, EGF accelerates gastroduodenal ulcer healing by stimulating cell proliferation, and this event is regulated through the Ras/Raf/MAP kinase pathway (Tarnawski and Jones, 1998). Moreover, in the healing process of gastric ulcers, ERKs have been shown to translocate to cell nuclei with activation of the c-fos gene which triggers cell proliferation (Tarnawski et al, 1998). Cutaneous wound re-epithelialisation and keratinocyte migration requires ordered gene expression and the fibroblast growth factor (FGF)-inducible response element (FiRE) required for migrating (but no proliferating) keratinocytes has been shown to be induced by treatment of cells with okadaic acid, the inhibitor of protein phosphatases which inactivate ERKs (Jaakkola et al, 1998).

The MAP kinase cascade is also be implicated in events relating to parturition. For example, induction of labour is commonly achieved with oxytocin and oxytocin induction of prostaglandin synthesis has been shown to be MAP kinase-dependent (Strakova et al, 1998). In fact, oxytocin causes rapid activation of MAP kinases in both human and rat puerperal uterine myometrial cultured cells (Nohara et al, 1996). Moreover, MAP kinase inhibition has been shown to inhibit prostaglandin-induced uterine contraction in animal models (Ohmichi et al, 1997). In addition, gelatinase B has been identified in amniotic fluid association with normal labour (Vadillo-Ortega et al, 1996) and gelatinase B production has been shown to be dependent on endogenous ERK signalling in other cell types such as keratinocytes (Zeigler et al, 1999; McCawley et al, 1999). Taken together, these date suggest that MAP kinase signalling may be an important regulator of parturition.

αvβ6 expression is also upregulated in type II alveolar epithelial cells during lung injury caused by injection of live bacteria and αvβ6 mRNA is induced within 5 hours of acute injury (Breuss et al, 1995). Interestingly, αvβ6 has been shown to be expressed on proximal airway epithelial cells in 50% of smokers undergoing lung resection (Weinacker et al, 1995). Just as in human keratinocytes, in primary cultures of human airway epithelial cells, TGF-β1 has been shown to dramatically increase expression of αvβ6 without affecting surface expression of any other integrin. Moreover, epidermal growth factor (EGF) also induces αvβ6 in these cells, and the effect of both growth factors on β6 expression has been shown to be additive (Wang et al, 1996). αvβ6 expression has also been observed in adult lungs and kidneys at focal sites of sub-clinical inflammation as well as in a variety of clinical specimens from patients with chronic or acute inflammation of the lungs or kidneys (Breuss et al, 1995). Taken together, this data and studies outlined above indicate that αvβ6 has a role in inflammation and affects for instance cell spreading, migration and growth during re-organisation of epithelial in development, tissue repair and neoplasia.

Hence, the application of agents, on either unwounded epithelial tissues (such as before surgery) or upon wounded epithelium, which up-relate MAP kinase activity may enhance cell migration and wound re-epithelialisation and thereby, hasten the healing process. Such agents may be based upon the binding domain on β6 for ERK2 and act therefore as β6 agonists (in the absence of this integrin) leading to MAP kinase activation. Examples of the application of such agents may include cell migration in wound healing, re-endothelialisation within natural or artificial blood vessels, or renewed nerve outgrowth following injury or disease. In addition, use of such agonists may for instance be useful in promoting induction of labour.

The epithelial restricted integrin subunit β6 is shown herein to interact with at least MAP kinases ERK2 and JNK-1, and its down-regulation dramatically suppresses growth of colon cancer. Hence, therapeutic strategies to inhibit growth and proliferation of colon cancer and growth of other malignant cancer cells by switching off either the permissive β6 integrin and/or inhibiting the β6 MAP kinase interaction are of particular interest. In particular, the fact that β6 expression may be significantly upregulated on tumour cells compared to normal cells offers the potential for tumour cell specificity substantially without impairment of normal cellular function.

Down-regulation of the functional activity of an integrin or MAP kinase may be achieved by preventing or down-regulating the expression of the integrin molecule or MAP kinase or by inhibiting the signalling function of the integrin or MAP kinase.

Gene therapy is one strategy for treating cancers of different types. The use of recombinant adenoviruses has for instance been utilised for restoring expression of polypeptide encoded by a wild-type p53 tumour suppressor gene (Bookstein et al, 1996), and adenoviral vectors for expression of wild-type p53 have been shown to suppress growth of human colon cancers by as much as 60% in animal models following intra-tumoural injection of recombinant virus (Spitz et al, 1996).

Rather than replacing a defective gene with one encoding a polypeptide the expression of which restores normal function of the cell as in the above examples, the possibility exists to achieve down regulation of cancer cells such as colon cells by introducing a gene that codes for an integrin subunit in which the binding domain for a MAP kinase has been rendered defective by mutagenesis, or in which the binding domain has been wholly or partially deleted, to thereby achieve down regulation through the inhibition of the MAP kinase integrin interaction. The defective integrin subunit will nevertheless usually be able to associate with its normal partner integrin subunit and be expressed on the cell membrane. Preferably, the defective integrin subunit will be expressed at a higher level than the corresponding wild-type integrin subunit such that down regulation is achieved by a dominant negative effect. Alternatively, such therapy may involve the introduction and expression of a nucleic acid sequence that encodes a fragment or truncated form of an integrin subunit that excludes the binding domain for the MAP kinase or in which the binding domain has been partially or wholly deleted or otherwise mutagenised so as to be defective. Similarly, a gene coding for a MAP kinase or a nucleic acid sequence coding for a fragment of a MAP kinase comprising the binding domain for an integrin may also be modified such that the binding domain of the MAP kinase is mutagenised or deleted.

Another option is to introduce a nucleic acid sequence encoding a polypeptide capable of binding to the binding domain on the integrin for the MAP kinase or to the binding site on the MAP kinase for the integrin upon being expressed within the cell to thereby inhibit intracellular binding of the MAP kinase to the integrin and thereby achieve down regulation of cellular activity.

A gene or nucleic acid sequence encoding an integrin subunit or MAP kinase may also be modified such that although the encoded binding domain for integrin or the MAP kinase as the case may be remains unaltered, the amino acid sequence of a region distant from the binding domain, or the amino acid sequence of either one or both regions immediately flanking the binding domain, is altered to achieve a change in the three dimensional conformation of the integrin subunit or MAP kinase such that the MAP kinase integrin binding interaction is inhibited.

The gene or nucleic acid sequence may be altered to achieve the desired outcome by the deletion, insertion or substitution of one or more nucleotides such that the corresponding amino acid sequence is modified to the extent that binding of the MAP kinase to the integrin is inhibited. Inhibition in this context may be partial or total inhibition.

The gene or nucleic acid sequence can be introduced into a cell in an appropriate expression vector for expression of the gene or nucleic acid sequence extrachromosomally or more preferably, for facilitating integration of the gene or nucleic acid sequence into genomic DNA by heterologous or homologous recombination events.

In another strategy, down-regulation of the expression of an integrin subunit such as β6 and hence an integrin heterodimer such as αvβ6 or the down regulation of expression of a MAP kinase such as ERK2, is achieved using antisense nucleic acid sequences (e.g. oligonucleotides) for inhibiting expression of the subunit or MAP kinase. Typically, this will involve expression of a nucleic acid construct incorporating all or part of a coding region of the gene for the integrin subunit or MAP kinase inserted in the reverse orientation resulting in the synthesis of antisense RNA which inhibits translation of mRNA encoding the integrin subunit or MAP kinase by hybridisation of the antisense RNA to the mRNA.

More broadly, a method of down regulating an activity of a cell by inhibiting expression of an intact integrin subunit or a MAP kinase may comprise contacting the cell with a first nucleic acid molecule that is capable of interacting with a target nucleic acid sequence coding for the subunit or MAP kinase, or which first nucleic acid molecule is capable of being transcribed to a nucleic acid molecule capable of interacting with the target sequence whereby the interaction of the first nucleic acid molecule with the target sequence inhibits expression of the integrin subunit or MAP kinase.

Reference to the first nucleic acid molecule is to be understood as a reference to any nucleic acid molecule which directly or indirectly facilitates reduction, inhibition or other form of down regulation of the expression of the integrin molecule or MAP kinase. Nucleic acid molecules which fall within the scope of this definition include antisense sequences administered to a cell and antisense sequences generated in situ which have sufficient complementarity with target sequence such as mRNA coding for the integrin subunit or MAP kinase or for instance, a transcription regulatory sequence controlling transcription of the gene coding for the integrin subunit or MAP kinase, to thereby be capable of hybridising with the target sequence and inhibit the expression of the integrin subunit or MAP kinase. The first nucleic acid molecule may also be a ribozyme capable for instance, specifically binding to that region of nucleic acid encoding the binding domain of an integrin subunit or MAP kinase or the binding domain of a MAP kinase for an integrin, and cleaving the nucleic acid.

Typically, an antisense strategy in accordance with the present invention will be directed toward inhibition of an intact integrin subunit to thereby down regulate cell activity via down regulation of interaction of the integrin with a MAP kinase.

On a priori grounds, targeting the expression of the β6 subunit in malignant cells such as in colon cancer by means of adenoviral-mediated antisense therapy is preferred because down-regulating β6 by means of a non-adenoviral approach may increase cell surface expression of the β5 subunit. The relevance to such therapy is that the vitronectin-binding integrin αvβ5 promotes adenovirus internalisation (Thomas et al, 1993). Given that abundant αvβ5 is always present on the surface of colon cancer cells for example, a secondary benefit of inhibiting β6 expression during the course of therapy may be the concomitant rise of β5 in cells already transduced with antisense β6 nucleic acid. This is likely to facilitate further virus uptake into such cells since the amount of integrin αvβ5 present has been shown to be closely related to levels of gene expression following adenovirus-mediated gene transfer (Takayama et al, 1998).

Typically, an antisense nucleic acid sequence will hybridise with all or part of that region of the target sense nucleic acid encoding the binding domain of an integrin subunit or the corresponding binding domain of a MAP kinase. An antisense nucleic sequence may for instance be capable of hybridising to exon and/or intron sequences of pre-mRNA. Preferably, an antisense nucleic acid sequence will be designed for specifically hybridising to mature mRNA in which intron sequences have been spliced out by normal cellular processing events.

It is not necessary that an antisense nucleic acid sequence have total complementarity with its target sequence only that substantial complementarity exists for specificity and to allow hybridisation under cellular conditions. Preferably, an antisense nucleic sequence will have a complementarity of about 70% or greater, more preferably about 80% or greater and most preferably, about 90% or 95% or greater. Preferred antisense sequences are oligonucleotides wherein the complementary sense nucleotides encode for about 50 amino acids or less, preferably about 35 or 30 amino acids or less, more preferably less than about 25 or 20 amino acids, most preferably about 15 amino acids or less and usually between about 5 to about 15 amino acids.

Antisense nucleic acid sequences may be generated in vivo by transcription of a suitable expression vector within a cell transformed with the vector, or ex vivo and then be introduced into a target cell to effect down regulation of the MAP kinase integrin interaction. Antisense sequences will desirably be designed to be resistant to endogenous exonucleases and/or endonucleases to provide in vivo stability in target cells. Modification to the phosphate backbone, sugar moieties or nucleic acid bases may also be made to enhance uptake by cells or for instance solubility, and all such modifications are expressly encompassed. Such modifications include modification of the phosphodiester linkages between sugar moieties, the utilisation of synthetic nucleotides and substituted sugar moieties, linkage to liphophilic moieties and the such like as described in U.S. Pat. No. 5,877,309. Methods for the construction of oligonucleotides for use in antisense therapy have previously been described (see Van der Krol et al, 1998 Biotechniques 6:958-976; and Stein et al, 1998 Cancer Res 48:2659-2668; Bachman et al, 1998, J. Mol. Med. 76:126-132).

Any means able to achieve the introduction of a gene or a nucleic acid into a target cell may be used. Gene transfer methods known in the art include viral and non-viral transfer methods. Suitable virus into which appropriate viral expression vectors may be packaged for delivery to target cells include adenovirus (Berkner, 1992; Gorziglia and Kapikian, 1992); vaccinia virus (Moss, 1992); retroviruses of avian (Petropoulos et al, 1992); murine (Miller, 1992) and human origin (Shimada et al, 1991); herpes viruses including Herpes Simplex Virus (HSV) and EBV (Margolskee, 1992; Johnson et al, 1992; Fink et al, 1992; Breakfield and Geller, 1997; Freese et al, 1990); papovaviruses such as SV40 (Madzak et al, 1992), adeno-associated virus (Muzyczka, 1992); BCG and poliovirus. Particularly preferred virus are replication deficient recombinant adenovirus (eg. He et al, 1998). Engineered virus may be administered locally or systemically to achieve delivery of the gene or nucleic acid sequence of interest into a target cell.

Gene transfer methods as described above may be used in the provision of transgenic animals for studying in vivo the effect of for instance, modifying the binding site of an integrin for a MAP kinase or the binding domain of the MAP kinase for the intergrin. A transgenic animal is one with cells that contain heterologous nucleic acid as a result of the deliberate introduction of the nucleic acid. The nucleic acid may be introduced indirectly by viral transfer as indicated above or directly by microinjection into a pronucleus of a fertilised egg prior to transfer of the egg to a surrogate mother for development to term. Alternatively, a gene or nucleic acid sequence of interest may be introduced into an embryonal stem (ES) cell in culture and the transformed cell injected into a recipient blastocyst which is then transferred to a surrogate mother for development to term. Techniques for generation of transgenic animals are for instance described in U.S. Pat. No. 4,873,191; Van der Putten, 1985; Thompson et al, 1989 and Lo, 1983.

A transgenic animal homozygous for a transferred gene for instance may be obtained by the mating of animals heterozygous for the gene as will be appreciated. Both animal cells expressing a heterologous gene or nucleic acid sequence and transgenic animals in which a particular gene has been mutagenised by homologous recombination may be provided. A transgenic animal may for instance be a mouse, rat, hamster or pig. Typically, the transgenic animal will be a mouse.

Agents for modulating the functional activity of a cell arising from the interaction of a MAP kinase like ERK2 or JNK-1 with a integrin include antagonists and inhibitors capable of associating with the integrin or MAP kinase to thereby inhibit the MAP kinase and integrin interaction. Antagonists and inhibitors include those agents that act by binding the integrin or MAP kinase adjacent to the relevant binding domain and stearically hindering the interaction of the MAP kinase with the integrin, as well as allostearic inhibitors that distort the binding domain upon associating with the integrin. Additional agents include agonists of a MAP kinase or an integrin, that are capable of binding to the pertinent binding domain involved in the MAP kinase integrin interaction.

A binding domain involved in the MAP kinase integrin interaction may be identified and characterised using protocols and techniques described herein. Specifically, a binding domain may be localised by assessing the capacity of respective overlapping peptide fragments of the cytoplasmic domain of an integrin subunit to bind with a MAP kinase or correspondingly, assessing the capacity of overlapping peptide fragments of the MAP kinase to bind with an integrin. The specific amino acid sequence which constitute the binding domain may then be determined utilising progressively smaller peptide fragments of a fragment observed to interact with the MAP kinase or the integrin. In particular, test peptides are readily synthesised to a desired length involving deletion of an amino acid or amino acids from either or both ends of the larger amino acid sequence, and tested for their ability to associate with the MAP kinase or integrin. This process is repeated until the minimum length peptide capable of binding with the MAP kinase or integrin substantially without compromising the optimum observed level of binding is identified.

The amino acids that play an active role in the MAP kinase integrin interaction may be achieved with the use of further synthesised test peptides in which one or more amino acids of the sequence are deleted or substituted with a different amino acid or amino acids to determine the effect on the ability of the peptide of associate with the MAP kinase or integrin. Typically, substitution mutagenesis will involve substitution of selected ones of the amino acid sequence with alanine or other relatively neutrally charged amino acid. By deletion is meant deletion of one or more of the amino acids between the N-terminal and C-terminal amino acid residues of the identified amino acid sequence.

Nucleotide and amino acid sequence data for the β6 integrin subunit for instance is found in Sheppard et al, 1990. The amino acid sequence for β6 is also set out in SEQ ID NO: 12. The nucleotide and amino acid sequence for ERK2 may be found in Boulton et al, 1991 and is set out in FIG. 39. Reference to such published data allows the ready design of peptide fragments of a MAP kinase or an integrin subunit cytoplasmic domain for use in the identification and localisation of the binding domain for the MAP kinase or the integrin as is applicable, and the identification of the corresponding nucleic acid sequence encoding such peptide fragments as well as the amino acid sequence of the binding domain.

Localisation and characterisation of a binding domain for a MAP kinase or integrin enables the design of agents for binding to the binding domain for modulation of cell activity either for down regulating the functional activity of the integrin or the MAP kinase and more particularly the MAP kinase integrin binding interaction, or as agonists of the MAP kinase or integrin. This will typically involve determining the physical properties of the binding domain such as size and charge distribution, and the tertiary structure of the binding domain.

Specifically, at least the region of the integrin containing the binding domain for the MAP kinase or the region of the MAP kinase containing the binding domain for the integrin is modelled taking into account the stereochemistry and physical properties of the binding domain such as size and charge distribution as well as its three dimensional structure as determined using x-ray chrstallography, nuclear magnetic resonance and/or commercially available computer modelling software. Such modelling techniques are well known in the art. In a variation of this approach, the modelling will take into account the interaction of the relevant binding domain with the MAP kinase or the integrin as the case may be such that any change in conformation arising from the interaction may be taken in to account in the design of an agent. Modelling flanking regions adjacent the binding domain also allows the design of agents for associating with such flanking regions but which are nevertheless capable of inhibiting the MAP kinase integrin interaction either by stearic hindrance or by distorting the conformation of the binding domain of the MAP kinase or integrin (eg. allostearic inhibitors).

The design of a mimetic of the binding domain of interest will usually involve selecting or deriving a template molecule onto which chemical groups are grafted to provide required physical and chemical characteristics. The selection of template molecule and chemical groups is based on ease of synthesis, likely pharmacological acceptability, risk of or potential for degradation in vivo, stability and maintenance of biological activity upon administration. Pharmacological acceptability and the like are also taken into consideration in the design of other agent types.

In order to constrain a polypeptide or other agent in a three dimensional conformation required for binding, it may be synthesised with side chain structures or otherwise be incorporated into a molecule with a known stable structure in vivo. In particular, a polypeptide or the like may be incorporated into an amino acid sequence at least part of which folds into a β-pleated sheet or helical structure such as an α-helix (eg. see Dedhar et al., 1997).

A polypeptide or other agent may also be cyclised to provide enhanced rigidity and thereby stability in vivo. Various methods for cyclising peptides, fusion proteins or the like are known (eg. Schiller et al., 1985). For example, a synthetic peptide incorporating two cysteine residues distanced from each other along the peptide may be cyclised by the oxidation of the thiol groups of the residues to form a disulfide bridge between them. Cyclisation may also be achieved by the formation of a peptide bond between the N-terminal and C-terminal amino acids of a synthetic peptide or for instance through the formation of a bond between the positively charged amino group on the side chain of a lysine residue and the negatively charged carboxyl group on the side chain of a glutamine acid residue. As will be understood, the position of the various amino acid residues between which such bonds are formed will determine the size of the cycle. Variation of cycle size for optimisation of binding affinity may be achieved by synthesising peptides in which the position of amino acids for achieving cyclisation has been altered. The formation of direct chemical bonds between amino acids or the use of any suitable linker to achieve cyclisation is also well within the scope of the skilled addressee.

Further strategies for identifying possible agents include large scale screening techniques as are known to the skilled addressee. For example, peptide library technology provides an efficient way of testing a vast number of potential agents. Such libraries and their use are well known. Prospective agents identified may be then further evaluated in suitable activity, competitive and other immunoassays. A method of screening for an agent or evaluating whether an agent is capable of binding to a MAP kinase or an integrin, and in particular the binding domain of a MAP kinase for an integrin or the binding domain of an integrin for a MAP kinase, and thereby inhibiting the MAP kinase integrin interaction or acting as a MAP kinase or integrin agonist, may for instance involve utilising the agent in an assay whereby the agent has the opportunity of binding to the MAP kinase or the integrin in the presence of the integrin or the MAP kinase as the case may be or prior to the addition of the integrin or the MAP kinase, and determining whether inhibition of binding of the MAP kinase to the integrin results. An alternate screening method may for instance involve selecting a test agent capable of binding with the integrin or MAP kinase, measuring cellular activity in the presence of the test agent, and comparing that activity with cellular activity in the absence of the test agent. Cellular activity may be assessed by cell growth as indicated by [$^3$H]-thymidine uptake or other measurement of cellular activity. As will be understood, a difference in observed functional activity in the presence of the test agent is indicative of the modulating effect provided by the test agent.

It will be understood that the integrin in the context of such assays may be an integrin subunit or polypeptide or fragment incorporating the binding domain of the integrin for the MAP kinase, or a homolog, analog, variant or derivative of such a molecule to which the MAP kinase is capable of binding. Similarly, a MAP kinase in this context may be an intact MAP kinase or a fragment thereof incorporating the binding domain for the integrin, or a homolog, analog, variant or derivative of such a molecule that is capable of binding with the binding domain of the integrin. In addition, determination of whether an agent is capable of binding to the binding domain of an integrin or MAP kinase may be achieved using a polypeptide or fragment as described herein consisting of the binding domain or a core amino acid sequence of the binding domain that directly participates in the binding interaction, or analogs or the like of such molecules.

It is not necessary that an agent be proteinaceous in character and indeed, mimetics may be prepared which may not be a polypeptide at all but which nevertheless possess the capability of binding with the integrin or MAP kinase.

Polypeptides including fusion proteins and fragments of a MAP kinase comprising the binding domain for an integrin or fragments of an integrin subunit comprising the binding domain for a MAP kinase, or which incorporate sufficient core amino acid sequence of the binding domain of the integrin or MAP kinase for binding by the MAP kinase or integrin are contemplated herein. Typically, a polypeptide will have a length of about 150 amino acids or less, more preferably about 100 or 50 amino acids or less and generally, less than about 40 amino acids. Preferably, the length will be from between about 5 to about 30 amino acids, and more preferably from between about 10 amino acids and about 25 amino acids. Preferably, a polypeptide will comprise or incorporate the amino acid sequence RSKAKWQTGTNPLYR (SEQ ID NO: 7), more usually the amino acid sequence RSKAKNPLYR (SEQ ID NO: 8), or one or both of sequences RSKAK (SEQ ID NO: 13) and NPLYR (SEQ ID NO: 14). Alternatively, a polypeptide may have the amino acid sequence HRDLKPSNLLLNTTCDLKICDFGLAR (SEQ ID NO: 1) or PSNLLLNTTCDLKIC (SEQ ID NO: 2).

Polypeptides and fusion proteins or the like may be synthesised or produced using conventional recombinant techniques. Nucleic acid encoding a fusion protein may for instance be provided via the joining together of separate DNA fragments encoding peptides or polypeptides having desired three dimensional conformations and/or other characteristics by employing blunt-ended termini and oligonucleotide linkers, digestion to provide staggered termini as appropriate, and ligation of cohesive ends prior to insertion of the resultant chimeric sequence into a suitable expression vector. Alternatively, PCR amplification of DNA fragments can be utilised employing primers which give rise to amplicons with complementary termini which can be subsequently ligated together (eg. see Current Protocols in Molecular Biology. John Wiley & Sons, 1992).

Nucleic acid sequences encoding for the polypeptides of the invention, mutagenised integrin subunits and the like as described herein are also encompassed as are the respective complementary antisense nucleic acid sequences.

Sense oligonucleotides encoding for the binding site of an integrin subunit or MAP kinase or a partial amino acid sequence of a binding domain, and the complementary antisense oligonucleotides are particularly suitable for use as primers in polymerase chain reaction (PCR) amplification methods or as probes for detection of the presence the respective target nucleic acid sequences with which they hybridise such as in Southern blotting protocols, or in affinity chromatography purification of the target nucleic acid sequence. Probes may be labelled with for instance commonly used isotopes such as $P^{32}$, fluorophores, chemiluminescent agents and enzymes (see eg. Essential Molecular Biology. A Practical Approach Vol. II, Oxford University Press, 1993; Current Protocols in Molecular Biology, Ausubel F M., John Wiley & Sons Inc., 1998). The choice of a label will vary depending on the degree of sensitivity required, ease of conjugation with the probe, safety and other factors.

Oligonucleotides for use as probes or primers will usually have a length of less than about 60 nucleotides, usually less than about 50 or 40 nucleotides preferably, between about 14 and about 30 nucleotides, and more preferably, between about 14 and about 25 nucleotides. While it is desirable that a primer or probe has 100% complementarity with its target sequence, oligonucleotides may be designed with less complementarity but which nevertheless hybridise with the target sequence. Typically, a primer or probe will have a complementarity of about 70% or greater, more preferably about 80% or greater and most preferably about 90% or 95%, or greater. A probe will generally be designed for being capable of hybridising with its target nucleic acid sequence under moderate or high stringency wash conditions. Moderate stringency wash conditions are for example those that employ 0.2×SSC (0.015M NaCl/0.0015M sodium citrate)/0.1% SDS (sodium dodecylsulfate) wash buffer at 42° C. High stringency wash conditions employ for instance, 0.1× SSC wash buffer at 68° C. Generally, the content of purine relative to the content of pyrimidine nucleotides in the region of target nucleic acid of interest will be taken into account in the design of such primers and probes as will be their length in accordance with well accepted principles known in the art.

In addition, the present invention provides vectors incorporating nucleic acid sequences of the invention. The term "vector" is to be taken to mean a nucleic acid molecule capable of facilitating the transport of a nucleic acid sequence inserted therein into a cell and includes expression vectors and cloning vectors.

Suitable expression vectors include plasmids and cosmids capable of expression of a DNA (eg. genomic DNA or cDNA) insert. An expression vector will typically include transcriptional regulatory control sequences to which the inserted nucleic acid sequence is operably linked. By "operably linked" is meant the nucleic acid insert is linked to the transcriptional regulatory control sequences for permitting transcription of the inserted sequence without a shift in the reading frame of the insert. Such transcriptional regulatory control sequences include promotors for facilitating binding of RNA polymerase to initiate transcription, expression control elements for enabling binding of ribosomes to transcribed mRNA, and enhancers for modulating promotor activity. A promotor may be a tissue specific promotor which facilitates transcription of the nucleic acid insert only in specific cell lineages and not in other cell types or only to a relatively low level in such other cell types. The design of an expression vector will depend on the host cell to be transfected, the mode of transfection and the desired level of transcription of the nucleic acid insert.

Numerous expression vectors suitable for transfection of prokaryotic (eg. bacterial) or eukaryotic (eg yeast, insect or mammalian cells) are known in the art. Expression vectors suitable for transfection of eukaryotic cells include pSV2neo, pEF.PGK.puro, pTk2, pRc/CNV, pcDNAI/neo, non-replicating adenoviral shuttle vectors incorporating the polyadenylation site and elongation factor 1-α promotor and pAdEasy based expression vectors most preferably incorporating a cytomegalovirus (CMV) promotor (eg. see He et al, 1998). For expression in insect cells, baculovirus expression vectors may be utilised examples of which include pVL based vectors such as pVL1392, and pVL941, and pAcUW based vectors such as pAcUW1. Viral expression vectors are particularly preferred.

Typical cloning vectors incorporate an origin of replication (ori) for permitting efficient replication of the vector, a reporter or marker gene for enabling selection of host cells transformed with the vector, and restriction enzyme cleavage sites for facilitating the insertion and subsequent excision of the nucleic acid sequence of interest. Preferably, the cloning vector has a polylinker sequence incorporating an array of restriction sites. The marker gene may be drug-resistance gene (eg. $Amp^r$ for ampicillin resistance), a gene encoding an enzyme such as chloramphenicol acetyltransferase (CAT), β-lactamase, adenosine deaminase (ADA), aminoglycoside phosphotransferase (APH), dihydrofolate reductase (DHFR), hygromycin-B-phosphotransferase (HPH), thymidine kinase (TK), or for instance β-galactosidase encoded by the *E. coli* lacZ gene (LacZ'). Yeast reporter genes include imidazole glycerolphosphate dehydratase (HIS3), N-(5'-phosphoribosyl)-anthranilate isomerase (TRP1) and β-isopropylmalate dehydrogenase (LEU2). As will be appreciated, expression vectors of the invention may also incorporate such marker genes.

Cloning vectors include cloning vectors for mammalian, yeast and insect cells. Particular vectors that may find application include pBR322 based vectors and pUC vectors such as pUC118 and pUC119. Suitable expression and cloning vectors are for instance described in Molecular Cloning. A Laboratory Manual., Sambrook et al., 2nd Ed. Cold Spring Harbour Laboratory., 1989.

Host cells suitable for being transformed by vectors of the invention include bacteria such as *E. coli, Bacillus* such as *B. subtilis, Streptomyces* and *Pseudomonas* bacterial strains, yeast such as *Sacchromyces* and *Pichia*, insect cells, avian cells and mammalian cells such as Chinese Hamster Ovary cells (CHO), COS, HeLa, HaRas, WI38, SW480, and NIH3T3 cells. Host cells may be cultured in a suitable culture medium and under conditions for facilitating expression of nucleic acid sequences of the invention or replication of cloning vectors, prior to purification from the host cells, and/or supernatants as the case may be using standard purification techniques.

Rather than utilising viral mediated transfection of cells, nucleic acid sequences and other molecules of the invention may also be delivered to a cell in vitro or in vivo by liposome mediated transfection. The liposomes may carry targeting molecules for maximising delivery of the agent or agents contained therein to specific cell types of interest. Such targeting molecules may be for instance antibodies, ligands or cell surface receptors for facilitating fusion of liposomes to the specific cells of interest. Agents may also be intracellularly delivered in vitro using conventional cold or heat shock techniques or for instance, calcium phosphate coprecipitation or electroporation protocols. Yet another strategy is to design the agent to have the inherent ability to pass across the lipid bilayer of a cell.

A particularly preferred way of achieving intracellular delivery of an agent is to use "carrier peptides" which have the ability to deliver macro-molecules across cell membranes in an energy-independent manner (Prociantz, 1996). Indeed, such peptides provide the possibility of both testing potential agents in cell culture without drastically altering cell membrane integrity and of delivering agents in vivo. Carrier peptides that are known in the art include penetratins and variants thereof (Derossi et al, 1994, 1996), human immunodeficiency virus Tat derived peptide (Prociantz, 1996), and transportan derived peptide (Pooga et al. 1998). Indeed, carrier peptides have been successfully used to facilitate internalisation of mimetics of Src homology 2 binding sites, and peptides which inhibit protein kinase C mediated axon development and CD44 (hyaluronate receptor) dependent migration (Theodore et al, 1995; Williams et al, 1997; Peck Isacke, 1998; Derossi et al, 1998).

Specific targetting to β6-expressing cancer cells may also be achieved by coupling humanised anti-β6 antibody to carrier molecules such as penetratin coupled to an agent capable of inhibiting binding of a MAP kinase with an integrin expressed by the cell or down regulation of the expression of the integrin. Coupling may for instance be by a peptide bond or disulfide bridge. Given that β6 expression enhances effective proteolysis at the cell surface by matrix metalloproteinase-9 (Agrez et al, 1999), such targetting approaches may include engineering an MMP-9 cleavage site between the antibody and the carrier peptide penetratin to facilitate internalisation of the pentratin-agent complex. Another approach may employ coupling the penetratin-agent complex to β6 integrin receptor-targetted peptides, targetted for binding to the extracellular β6 domain by virtue of their DLXXL sequence. For example, a ligand recognition motif for αVβ6 integrin, RTDLDSLRTYTL (Kraft et al, 1999) may be used in conjunction with or without an engineered MMP-9 cleavage site to release the penetratin-agent complex at the cell surface. Further protocol for targetting nucleic acids to cells by targetting integrins is described in Bachmann et al, 1998.

The toxicity profile of an agent of the invention may be tested on normal and malignant cells by evaluation of cell morphology, trypan-blue exclusion, assessment of apoptosis and cell proliferation studies (eg cell counts, $^3$H-thymidine uptake and MTT assay).

Agents of the invention may be co-administered with one or more other compounds or drugs. For example, an agent or agents may be administered in combination with antisense therapy or chemotherapeutic drugs. Alternatively, an agent may be administered in conjunction with antisense therapy and/or chemotherapeutic drugs. By "co-administered" is meant simultaneous administration in the same formulation or in two different formulations by the same or different routes, or sequential administration by the same or different routes. By "sequential" administration is meant a time difference of between the administration of the agents, drugs and other therapies which can be administered in any order. The time difference may range from very short times up to hours or for instance days or weeks.

The agent or agents will typically be formulated into pharmaceutical composition incorporating pharmaceutically acceptable carriers, diluents and/or excipients for administration to the intended subject.

Pharmaceutical forms include sterile aqueous solutions suitable for injection, (where the agent or agents is water soluble) and sterile powders for the extemporaneous preparation of sterile injectable solutions. Such injectable compositions will be fluid to the extent that the syringability exists and typically, will be stable to allow for storage after manufacture. The carrier may be a solvent or dispersion medium containing one or more of ethanol, polyol (eg glycerol, propylene glycol, liquid polyethylene glycol and the like), vegetable oils, and suitable mixtures thereof. Fluidity may be maintained by the use of a coating such as lecithin, by the maintenance of the required particle size in the case of a dispersion and by the use of surfactants.

Sterile injectable solutions will typically be prepared by incorporating the active agents in the desired amount in the appropriate solvent with various other components enumerated above, prior to sterilising the solution by filtration. Generally, dispersions will be prepared by incorporating the sterile active agents into a sterile vehicle which contains the dispersion medium and other components. In the case of sterile powders for the preparation of sterile injectable solutions, preferred methods of preparation are vacuum drying and freeze-drying techniques which yield a powder of the active agent plus any additional desired ingredient from previously sterile filtered solutions thereof.

For oral administration, the active agents may be formulated into any orally acceptable carrier deemed suitable. In particular, the active ingredient may be formulated with an inert diluent, an assimilable edible carrier or it may be enclosed in a hard or soft shell gelatin capsule. Alternatively, it may be incorporated directly into food. Moreover, an active agent may be incorporated with excipients and used in the form of ingestable tablets, buccal tablets, troches, capsules, elixirs, suspensions, syrups, and the like.

Such compositions will generally contain at least about 1% by weight of the active agent or agents. The percentage may of course be varied and may conveniently be between about 5 to about 80% w/w of the composition or preparation. As will be appreciated, the amount of active agent or agents in such compositions will be such that a suitable effective dosage will be delivered to the subject taking into account the proposed mode of administration. Preferred oral compositions according to the invention will contain between about 0.1 μg and 2000 mg of each active agent, respectively.

Active agents may also be formulated into topically acceptable carriers conventionally used for forming creams, lotions, ointments and the like for internal or external application. Topical formulations may be applied to a site to be treated by dressings and the like impregnated with the formulation.

Typically, a composition of the invention will incorporate one or more preservatives such as parabens, chlorobutanol, phenol, sorbic acid, and thimersal. In many cases, a composition may furthermore include isotonic agents such as sugars or sodium chloride. In addition, prolonged absorption of the composition may be brought about by the use in the compositions of agents for delaying absorption such as aluminium monosterate and gelatin.

Tablets, troches, pills, capsules and the like may also contain one or more of the following: a binder such as gum tragacanth, acacia, corn starch or gelatin; excipients such as dicalcium phosphate; a disintegrating agent such as corn starch, potato starch, alginic acid and the like; a lubricant such as magnesium sterate; a sweetening agent such as sucrose, lactose or saccharin or a flavouring agent such as peppermint, oil of wintergreen, orange or cherry flavouring. When the dosage unit form is a capsule, it may contain in addition to one or more of the above ingredients a liquid carrier. Various other ingredients may be present as coatings or to otherwise modify the physical form of the dosage unit. For instance, tablets, pills or capsules may be coated with shellac, sugars or both. In addition, an active agent may be incorporated into any suitable sustained-release preparation or formulation.

Pharmaceutically acceptable carriers, diluents and/or excipients include any suitable conventionally known solvents, dispersion media and isotonic preparations or solutions. Use of such ingredients and media for pharmaceutically active substances is well known. Except insofar as any conventional media or agent is incompatible with the active agent, use thereof in therapeutic and prophylactic compositions is contemplated. Supplementary active ingredients can also be incorporated into the compositions if desired.

It is particularly preferred to formulate parenteral compositions in dosage unit form for ease of administration and uniformity of dosage. Dosage unit form as used herein is to be taken to mean physically discrete units suited as unitary dosages for the subject to be treated, each unit containing a predetermined quantity of active agent calculated to produce the desired therapeutic or prophylactic effect in association with the relevant carrier, diluent and/or excipient.

A unit dosage formed will generally contain each active agent in amounts ranging from about 0.5 μg to about 2000 mg/ml of carrier respectively.

A pharmaceutical composition may also comprise vectors capable of transfecting target cells where the vector carries a nucleic acid molecule for modulating functional activity or expression of an integrin or MAP kinase. The vector may for instance, be packaged into a suitable virus for delivery of the vector into target cells as described above.

The dosage of an active agent will depend on a number of factors including whether the agent is to be administered for prophylactic or therapeutic use, the condition for which the agent is intended to be administered, the severity of the condition, the age of the subject, and related factors including weight and general health of the subject as may be determined by the physician or attendant in accordance with accepted principles. Indeed, a low dosage may initially be given which is subsequently increased at each administration following evaluation of the subjects response. Similarly, frequency of administration may be determined in the same way that is, by continuously monitoring the subjects response between each dosage and if necessary, increasing the frequency of administration or alternatively, reducing the frequency of administration.

The route of administration of a pharmaceutical composition will again depend on the nature of the condition for which the composition is to be administered. Suitable routes of administration include but are not limited to respiritoraly, intratracheally, nasopharyngeally, intraveneously, intraperitonealy, subcutaneously, intracranialy, intradermially, intramuscularly, intraoccularly, intrathecally, intranasally, by infusion, orally, rectally, via IV group patch, topically and by implant. With respect to intravenous routes, particularly suitable routes are via injection into blood vessels which supply a tumour or particular organs to be treated. Agents may also be delivered into cavities such for example the pleural or peritoneal cavity, or be injected directly into tumour tissue.

The production of antibodies and monoclonal antibodies is well established in the art (eg. see Antibodies, A Laboratory Manual. Harlow & Lane Eds. Cold Spring Harbour Press, 1988). For polyclonal antibodies, a mammal such as a sheep or rat for instance is immunised with a polypeptide of the invention and antisera subsequently isolated prior to purification of the antibodies therefrom by standard affinity chromatography techniques such as Sepharose-Protein A chromatography. Desirably, the mammal is periodically challenged with the relevant antigen to establish and/or maintain high antibody titre. To produce monoclonal antibodies, B lymphocytes can be isolated from the immunised mammal and fused with immortalising cells (eg. myeloma cells) by standard somatic cell fusion techniques (eg. utilising polyethylene glycol) to produce hybridoma cells (Kohler and Milstein, 1975; see also Handbook of Experimental Immunology, Weir et al Eds. Blackwell Scientific Publications. 4th Ed. 1986). The resulting hybridoma cells may then be screened for production of antibodies specific for the peptide by an enzyme linked immunosorbant assay (ELISA) or other immunoassay. Conventionally used methods for preparing monoclonal antibodies include those involving the use of Epstein-Barr virus (Cole et al. Monoclonal Antibodies and Cancer Therapy, Allen R. Liss Inc. pp. 77-96, 1985). The term “antibody” or “antibodies” as used herein is to be taken to include within its scope entire intact antibodies as well as binding fragments thereof such as Fab and $(Fab')_2$ fragments which may be obtained by papain or pepsin proteolytic cleavage, respectively.

An antibody of the invention may be labelled for enabling detection of antibody binding in immunoassays including competitive inhibition assays. A “label” may be any molecule which by its nature is capable of providing or causing the production of an analytically identifiable signal which allows the detection of an antibody and antigen complex. Such detection may be qualitative or quantitative. An antibody can for instance be labelled with radioisotopes including $^{32}P$, $^{125}I$ or $^{131}I$, an enzyme, a fluorescent label, chemiluminescent molecule or for instance an affinity label such as biotin, avidin, streptavidin and the like.

An enzyme can be conjugated with an antibody by means of coupling agents such as gluteraldehyde, carbodiimides, or for instance periodate although a wide variety of conjugation techniques exist. Commonly used enzymes include horseradish peroxidase, glucose oxidase, β-galactosidase and alkaline phosphatase amongst others. Detection utilising enzymes is achieved with use of a suitable substrate for the selected enzyme. The substrate is generally chosen for the production upon hydrolysis of a detectable colour change. However, fluorogenic substrates may also be used which yield a fluorescence product rather than a chromogen. Suitable fluorescent labels are those capable of being conjugated to an antibody substantially without altering the binding capacity of the antibody and include fluorescein, phycoerythrin (PE) and rhodamine which emit light at a characteristic wavelength in the colour range following illumination with light at a different wavelength. Methods for labelling of antibodies can be found in Current Protocols in Molecular Biology. Ausubel F M., John Wiley & Sons Inc.

Immunoassays in which antibodies of the invention may be utilised include radioimmunoassays (RIA) and ELISA (eg., see Handbook of Experimental Immunology, Weir et al., Vol. 1-4, Blackwell Scientific Publications 4th Edition, 1986). Such assays include those in which a target antigen is detected by direct binding with a labelled antibody, and those in which the target antigen is bound by a first antibody, typically immobilised on a solid substrate (eg., a microtitre tissue culture plate formed from a suitable plastics material such as polystyrene or the like) and a labelled second antibody specific for the first antibody used to form an antigen-first antibody-second antibody complex that is detected by a signal emitted by the label. Sandwich techniques in which the antigen is immobilised by an antibody for presentation to a labelled second antibody specific for the antigen are also well known. An antibody can be bound to a solid substrate covalently utilising commonly used amide or ester linkers, or by adsorption. Optimal concentrations of antibodies, temperatures, incubation times and other assay conditions can be determined by the skilled addressee with reference to conventional assay methodology and the application of routine experimentation.

Antibodies and other molecules of the invention including polypeptides and oligonucleotides as described herein when bound to a solid support can be used in affinity chromatography for the purification of a binding partner for which they are specific. In particular, a polypeptide either alone or as a fusion protein comprising or consisting of the binding domain for a MAP kinase for instance can be utilised in the purification, isolation or concentration of an integrin or fragment thereof or other molecule capable of binding to the binding domain of the MAP kinase for the integrin. It may also be used for assaying levels of the integrin for instance in cell extracts. Similarly, an antibody or other such molecule as described herein that specifically binds to the binding domain of a MAP kinase has use in the purification of the MAP kinase or fragments thereof incorporating a binding domain for the integrin from a relatively crude preparation or mixture.

Suitable solid supports include agarose, sepharose and other commercially available supports such as beads formed from latex, polystyrene, polypropylene, dextran, glass or synthetic resins, typically packed in an affinity column through which the relevant sample containing the binding partner is passed at a pH and conditions (eg., low salt concentration) under which the binding partner becomes bound by the antibody, polypeptide or other such molecule. The column is then washed utilising a suitable buffer whereby the binding partner is retained bound on the column, prior to being eluted therefrom utilising a suitable elution buffer (eg., with a higher salt concentration and at an altered pH, typically pH 2.5 or pH 11) that facilitates the release of the binding partner from the affinity column, and collected. Protocols for affinity chromatography are described in Current Protocols in Molecular Biology-Ausubel F M., John Wiley & Sons Inc. Buffers and conditions utilised for the purification, isolation or concentration of a binding partner will vary depending on the affinity the antibody, polypeptide or the like for the binding partner.

A kit for use in assays as described herein may include one or more of an antibody, polypeptide, vector, nucleic acid or other molecule of the invention. The kit may also comprise one or more other reagents such as washing solutions, dilution buffers and the like together with instructions for use. The antibody or other molecule of the invention may or may not be labelled, bound to a solid support or be coupled with another molecule. Particularly preferred kits are those provided for use in affinity chromotography or RIA, ELISA or other type of immunoassay.

The present invention will be described herein after with reference to a number of examples.

EXAMPLE 1

Anti-integrin antibodies and antibodies against the β1 subunit have been shown to inhibit proliferation of retinal pigment epithelial cells (Hergott et al, 1993). In endothelial cells, inhibition of cell-matrix interactions by anti-integrin antibodies specifically against α2β1 converts the cells from a proliferative to a differentiated phenotype (Gamble et al, 1993). In another study, synthetic peptides containing the integrin recognition sequence arginine-glycine-aspartate (RGD) have been shown to inhibit tumour cell invasion in vitro and tumour metastases from melanoma in an animal model (Humphries et; al, 1986; Gehlsen et al, 1988).

In colon cancer, the contribution made by the α5β1 receptor to regulation of growth appears to be ligand (fibronectin)-dependent. For example, induced expression of α5β1 in human colon cancer cells constitutively lacking this integrin has been shown to result in decreased tumour cell proliferation in vitro (Varner et al, 1995). Interestingly, when the appropriate ligand was present, cell proliferation was restored, indicating that the unoccupied receptor mediated a negative growth signal in these cells (Varner et al, 1995). Moreover, induction of α5β1 expression was associated with a marked reduction of tumourigenicity in immune-deficient mice. Failure to ligate all of the tumour cell α5β1 molecules with sufficient murine fibronectin most likely accounts for the in vivo tumour suppression in these studies (Varner et al, 1995). In the present study the effect of down-regulating αvβ6 expression on colon cancer growth was examined.

1.1 Methods 1.1.1 Generation of sense and antisense β6 constructs in pEF.PGK.puro vector. For β6 antisense constructs, β6 cDNA was excised from the vector pcDNA1neo β6 (Weinacker et al, 1994) using the restriction enzymes SnaB1 and Xba1. This produced a 5' overhang (Xba1) and a 3' blunt end (SnaB1). The 5' overhang was blunted with Klenow (Promega) prior to ligation. pEF.PGK.puro vector (a gift from D. Huang, the Walter & Eliza Hall Institute, Melbourne Australia) was cut with EcoRV which produced blunt ends. The pEF.puro vector was de-phosphorylated using calf intestinal alkaline phosphatase (CIAP, Promega) and the β6 cDNA ligated overnight into pEF.puro using T4 DNA ligase (Promega) at a ratio of vector:insert of 1:5. After ligation all the reaction mix was used for transformation into competent JM109 cells and the cells plated onto LB plates containing ampicillin. After overnight incubation at 37° C., colonies were selected, the plasmid DNA extracted by microprepping, and the DNA cut with BstE11 to confirm the antisense orientation of β6. Digestion with BstE11 produced the expected two fragments, one of 6.0 basepairs and the other 3.5 basepairs.

To provide β6 sense constructs, β6 cDNA was also excised from the pcDNA1neo b6 vector using the restriction enzymes Snab1 and Xba1 as described above. The pEF.puro vector was then cut with Xba1 and EcoRV and the insert was ligated in sense direction into the pEF.PGK.puro vector without having to blunt the insert. The ligation reaction was prepared at a ratio of vector:insert of 1:1. Digestion with BstE11 produced two expected fragments, one of 7.5 basepairs and the other 2.0 basepairs.

1.1.2 Transfection of WiDr and HT29 Colon Cancer Cells

The human colon cancer cell lines, WiDr and HT29 were obtained from the American Type Culture Collection (ATCC), Rockville, Md., USA and maintained as monolayers in standard medium comprising Dulbecco's Modified Eagle's medium (DMEM; 4.5 gm/litre of glucose) with 10% heat-inactivated foetal bovine serum (FBS) supplemented with HEPES and penicillin/streptomycin. WiDr and HT29 cell lines constitutively express αvβ6. Stable transfectants of WiDr and HT29 cells expressing β6 in sense and antisense direction were generated using lipofectamine and puromycin as the selection antibiotic. One stable antisense β6 transfectant from HT29 cells and three stable clones from WiDr cells were successfully established for use in all experiments. Mock transfectants using vector alone were also generated as controls. Initial killing curves performed using a range of concentrations of puromycin established that WiDr and HT29 cells could be stably transfected with puromycin concentrations of 1.0 µg and 2.5 µg/ml, respectively.

1.1.3 Assessment of β6 Expression in the Transfected Cell Lines

β6 expression was assessed by means of FACScan analyses of parent cell lines and clones generated therefrom by means of limiting-dilution experiments. Stability of the transfectants was confirmed regularly by repeated FACScan analyses, and surface biotinylation and immunoprecipitation as described below.

1.1.4 FACScan Analyses

Monolayer cultures of cell lines were harvested with trypsin/EDTA and then blocked with goat serum at 4° C. for 10 min. Cells were washed once with PBS, incubated with primary antibody against integrin subunits for 20 min at 4° C. and then washed twice with PBS. Cells were then stained with secondary antibody conjugated with phycoerythrin for 20 min at 4° C., washed twice with PBS and resuspended in 0.5 ml PBS prior to FACScan analysis (Becton Dickinson, Rutherford, N.J., USA).

1.1.5 Integrin Immunoprecipitation

Cells were harvested with trypsin/EDTA, the trypsin neutralised with standard culture medium, and the cell pellets washed once with cold PBS. Cell pellets were then exposed to biotin-CNHS-ester (Sigma) in biotinylation buffer (10 mM sodium borate, 150 mM sodium chloride, pH 8.8) for 30 mins at 4° C. with continuous slow mixing. Cell pellets were then centrifuged at 4° C., washed twice with cold PBS and exposed to lysis buffer (containing 100 mM Tris, 150 mM NaCl, 1 mM $CaCl_2$, 1% Triton, 0.1% SDS and 0.1% NP-40 at pH 7.4 and containing 1 mM phenylmethylsulfonyl fluoride (PMSF)) for 30 min at 4° C. Lysates were then clarified by ultracentrifugation (10,000 g) for 30 min and the protein content measured using the BCA protein assay reagent kit. Lysates containing equal protein amounts were pre-cleared with rabbit anti-mouse (RAM) immunoglobulin coupled to Sepharose-4B beads for 12 hrs. Immunoprecipitations were carried out indirectly using RAM-Sepharose 4B and analysed by 7.5% SDS-PAGE under non-reducing conditions.

1.1.6 Reverse Transcriptase-PCR (RT-PCR)

mRNA levels for β6 expression were evaluated by reverse transcriptase-polymerase chain reaction (RT-PCR). Total RNA was extracted from cell cultures using the commercial TriPure isolation reagent based on the method of Chomozynski and Sacchi (1987). 0.4-2 μg of RNA was used to prepared cDNA by reverse transcription. Briefly, a reaction mixture in a final volume of 40 μl containing 8 μl of 5×RT reaction buffer (250 mM Tris, 15 mM $MgCl_2$, 375 mM KCL, pH 8.3), 8 μl of 2.5 mM of each dNTP, 4 μl of 100 mM DTT, 40 U of an Rnase inhibitor, Rnasin (Promega, Madison, Wis., USA), 0.5 μg of random hexamers (Promega) and 200 U of Moloney murine leukaemia virus (M-MLV) reverse transcriptase (Promega) were mixed and incubated at 38° C. for a minimum of 90 min. The reaction was stopped by heating at 95° C. for 5 min and cDNA stored at 4° C. until PCR. 2-5 μl of this cDNA was combined with 5 μl of 10×PCR buffer (100 mM Tris, 500 mM KCl, 15 mM $MgCl_2$, pH8.3) 8 μl of 1.25 mM dNTP each and 1.25 μl of 20 μM of both forward and reverse primers. The forward primer sequence was 5'AGGATAGTTCTGTTTC-CTGC3' (SEQ ID NO: 15) and the reverse primer sequence 5'ATCATAGGAATATTTGGAGG3' (SEQ ID NO: 16). The reaction was initiated by 2.5 U of Taq polymerase in a final volume of 50 μl. After an initial 5 min incubation at 94° C., 30 cycles of amplification were performed under the following conditions: 94° C. 1 min, 54° C. 1 min and 72° C. for 1 min. The reaction was stopped by incubating at 72° C. for 10 min. To verify that equal amounts of RT product from cells were subjected to PCR amplification, the same amounts of cDNA were amplified for the "house-keeping" gene GAPDH using specific primers. The same reaction conditions were used except that the annealing temperature was changed to 48° C. and PCR amplification performed for 35 cycles.

1.2 Results 1.2.1 αvβ6 Expression in HT29 and WiDr Transfected Cell Lines

Transfection of the colon cancer cell lines HT29 and WiDr with the β6 gene construct in an antisense orientation resulted in a marked reduction of β6 expression at the transcript level and on the cell surface as shown in FIGS. 1 to 4. Transfection of cells with β6 in the sense orientation did not enhance β6 surface expression. However, a consequence of down-regulation of the β6 subunit in antisense transfectants was a marked increase in surface expression of the β5 subunit. The changes in surface expression of β6 and β5 subunits noted on FACScan analyses of antisense β6 transfectants was confirmed by surface-labelling cells with biotin and immunoprecipitating integrin subunits with either anti-β6 mAb (R6G9) or anti-β5 mAb (P1F6).

1.2.2 Effect of Suppression of αvβ6 Expression on Cell Binding to Fibronectin

The major substrate for αvβ6 is fibronectin and to investigate the effect that reduction in β6 surface expression in antisense β6 transfectants might have on cell-matrix adhesion, WiDr and HT29 antisense β6 transfectants were seeded on fibronectin in adhesion assays. Since both cell lines can adhere to fibronectin through members of the β1 integrin subfamily (either α3β1 or α5β1) αvβ6-mediated adhesion to fibronectin was assessed in the absence/presence of blocking anti-β1 antibody.

The cell-adhesion assays were performed in wells of non-tissue culture-treated polystyrene 96-well flat bottom microtitre plates (Nunc, Roskilde, Denmark). Culture wells were coated with fibronectin, washed with phosphate-buffered saline (PBS) and then blocked with 0.5% bovine serum albumin (Sigma) in PBS for 1 hr at 37° C. Harvested cells were seeded at a density of $10^5$ cells/well for HT29 and $1.5\times10^5$ cells/well for WiDr cells in 200 μl of standard DMEM which lacked FBS but contained 0.5% bovine serum albumin. To block adhesion, cells were incubated with anti-β1 blocking antibodies for 15 min at 4° C. before plating. The plates were centrifuged (top side up) at 10×g for 5 min, then incubated for 1 hr at 37° C. in humidified 5% carbon dioxide. Non-adherent cells were removed by centrifugation top side down at 48×g for 5 min. The attached cells were fixed and stained with 0.5% crystal violet (in 20% methanol and 1% formaldehyde) and the wells washed with phosphate-buffered saline. The relative number of cells in each well was evaluated by measuring the absorbance at 595 nm in a Microplate Reader (Bio-Rad).

With reduction in cell surface expression of β6, β1-independent adhesion of cells to fibronectin was reduced compared with mock transfectants (containing vector alone) which express surface β6 at similar levels to wild-type cells. The further addition of blocking anti-αv antibody completely prevented binding to fibronectin.

1.2.3 Effect of Suppression of αvβ6 Expression on Tumour Cell Proliferation and Tumour Growth In Vivo To investigate the effect of diminished αvβ6 surface expression on cell proliferation in vitro, WiDr and HT29 antisense β6 transfectants were seeded as monolayers in 96-well microtitre culture plates (5,000 viable cells per well) in standard culture medium containing the puromycin selection antibiotic. Cells were pulsed with 1 μCi ($^3$H)-thymidine (Amersham) per well for the last 24 hours of each experiment before automated harvesting and measurement of radioactivity. WiDr wild-type, mock and antisense β6 transfectants, and HT29 wild-type, mock, sense β6 and antisense β6 transfectants were harvested second daily during a six-day culture period.

A marked increase in thymidine incorporation was observed for WiDR and HT29 cells expressing normal levels of αvβ6 compared with antisense β6 transfectants (see FIGS. 5 and 6).

1.2.4 Effect of Suppression of αvβ6 Expression on Tumour Formation

The ability of HT29 antisense β6 transfactants to form tumours in immune-deficient mice was assessed.

BALB/C female athymic mice (8 weeks of age purchased from the Animal Resource Centre, Perth, Western Australia) were maintained under pathogen-free conditions and fed standard mouse chow and water ad lib. The mice were divided into groups of ten each and all mice within each group inoculated with a single cell line. Cells used were WiDr mock (transfected with vector alone) and antisense β6 transfected clones (clones 1-3) and HT29 mock, sense and antisense β6 cell lines. Mice received subcutaneous flank injections of $10^6$ viable tumour cells suspended in 0.2 ml of standard DMEM culture medium. Animal weights and tumour sizes (breadth and length as measured with calipers) were recorded weekly. Six weeks following the last injection, visible subcutaneous tumours were excised, weighed and fixed in 4% formalin. At the time of euthanasia, all internal organs were routinely inspected for presence of metastases.

Tumour growth after six weeks following inoculation of HT29 mock and antisense β6 transfectants is shown in FIG. 7. Measurements of tumour growth for WiDr and HT29 cells are shown in FIGS. 8 and 9, respectively. Similar tumour growth profiles for mock and antisense β6 WiDr clones 2 and 3 each inoculated into 10 mice are not shown. Of a total of 40 mice injected with cells expressing antisense β6 (HT29-10 mice and WiDr cells lines, 3 clones-30 mice) tumours completely disappeared in 93% of animals. In the remaining 3 animals tumour sizes diminished to 1 $mm^2$ in size during the six week period compared with tumours at least 15 $mm^2$ in size from cells expressing normal levels of β6. To confirm the presence of tumour xenografts histologically at one week following subcutaneous inoculation of mock and antisense β6 transfectants, tumour nodules were excised, fixed in formalin and stained with haematoxylin and eosin.

1.2.5 Effect of Suppression of αvβ6 Expression on Gelatinase B Secretion

Serum-free tumour-conditioned medium was collected from each of the 3 WiDr mock and antisense β6 clones and concentratedx44 for measurement of gelatinase B using the Biotrak MMP-9 activity assay system (Amersharn Pharmacia Biotech, Uppsala Sweden). Down-regulation of αvβ6 expression resulted in a marked reduction in gelatinase B secretion.

1.3 Discussion of Results

Induced expression of β6 in Chinese hamster ovary (CHO) cells has been shown to result in decreased surface expression of the β5 integrin subunit which also partners αv (Weinacker et al, 1994). The concept of integrin switching depends on the availability of the promiscuous αv partner subunit. In the present study, the reverse was observed. As a consequence of down-regulation of β6 in colon cancer cells which constitutively express αvβ6, β5 surface expression increased, most likely secondary to increased availability of the αv subunit partner.

Heterologous expression of αvβ6 in colon cancer cells has previously been reported to enhance tumour growth in immune-deficient mice (Agrez et al, 1994). Suppression of αvβ6 expression in the present study was shown to result in nearly complete disappearance of tumours in 93% of animals following subcutaneous inoculation of tumour cells. Moreover, in the remaining 7% of animals, a 95% reduction in tumour size was observed over a six week period compared with large tumours seen in all animals injected with cells in which αvβ6 expression had not been perturbed. Similar findings have been described with loss of the classical vitronectin receptor αvβ3 in melanoma. For example, in experimental animal models, the loss of αvβ3 expression in melanoma cells has been shown to lead to reduced in vivo proliferation which is restored upon re-expression of the receptor (Felding-Habermann et al, 1992).

Although the mechanisms involved in αvβ6-mediated tumour growth remain to be elucidated, the present in vitro data show that loss of β6 expression is associated with decreased proliferative capacity of the cells. Taken together with the marked reduction in gelatinase B secretion seen for colon cancer cells transfected with antisense β6, the findings reported in the present study suggest that intracellular signalling pathways activated via the integrin αvβ6 play a major role in promoting progression of this tumour type.

EXAMPLE 2

The association of αvβ6 expression and MAP kinase activity were evaluated using WiDr, HT29 and SW480 cell lines.

2.1 Methods 2.1.1 SW480 Colon Cancer β6 Transfectants

Stable transfectants of SW480 colon cancer cells (ATCC) expressing gene constructs of either wild-type or mutant forms of the β6 integrin subunit or the expression plasmid only (pcDNA1neo) have been previously described (Agrez et al, 1994). The transfected SW480 cell lines were maintained in standard medium supplemented with the neomycin analogue G418. Stable transfectants of WiDr and HT29 cells expressing wild-type β6 in antisense orientation were generated as described in Example 1.1.2 and maintained in standard medium supplemented with puromycin.

2.1.1 MAP Kinase Assay.

Cultures of WiDr and HT29 mock and antisense β6 transfectants were established by seeding $1\times10^6$ cells/5 ml of culture medium in 25 $cm^2$ tissue culture flasks. Cells were incubated at 37° C. in humidified $CO_2$ for 24 hours before serum starvation in serum-free medium for the next 16 hours. Foetal calf serum was then added to a final concentration of 10% for 30 mins before MAP kinase assays were performed. Before each experiment the cells were washed twice with PBS, resuspended in extraction buffer (10 mM Tris-HCl, 150 mM NaCl, 2 mM EDTA, 2 mM DTT, 1 mM orthovanadate, 1 mM PMSF, 4 μg/ml aprotonin, 2 μg/ml leupeptin and 1 μg/ml pepstatin, pH 7.4) and sonicated at a setting of 7, using a Soniprep 150 watt ultrasonic disintegrator for a total of 90 seconds in three 30 second pulses with an interval of 30 seconds between each pulse. Cellular debris was removed by centrifugation at 900 g for 10 min at 4° C. The assay was performed on equal cell numbers using a MAP kinase assay system (Amersham Pharmacia Biotech, Uppsala Sweden). The ability of cells to transfer phosphate from [$\gamma^{32}$P]-ATP to a synthetic peptide that contains specifically a p42/p44 MAP kinase phosphorylation site was measured as described in the manufacturer's instructions. [$^{32}$P]-labelled peptides were spotted onto PEI-cellulose paper, unbound radioactivity was washed with 75 mM phosphoric acid and bound [$^{32}$P]-labelled peptides were measured by liquid scintillation counting. Protein estimation was performed on each cell lysate used and enzyme activity calculated as described in the manufacturer's instructions. Where MEK inhibitors, PD98059 and U0126 were used, cells were cultured as described above and the inhibitors, at a final concentration of 40 μM, were added one hour before the addition of serum to the medium.

2.1.2 Western Blotting

To detect the MAP kinases ERK1/2, cells were lysed in lysis buffer containing 100 mM Tris, 150 mM NaCl, 1 mM CaCl2, 1% Triton, 0.1% SDS and 0.5% NP-40 at pH7.4, supplemented with enzyme inhibitors (1 mM PMSF, 1 mM sodium orthovanadate, 1 μg/ml pepstatin A, 2.5 μg/ml aprotonin, 1 mM benzamidine, 1 μg/ml leupeptin). Lysates were clarified by ultracentrifugation and equal protein loads electrophoresed in 8% or 10% SDS-PAGE under non-reducing conditions. Electrophoresed proteins were transferred to nitrocellulose membranes (Biotrace NT, Gelman Sciences, Ann Arbor, Mich.) in transfer buffer (25 mM Tris, 192 mM glycine, 20% methanol, 0.1% SDS) for 2 hours at a constant voltage of 40 volts in a Transfer Blot Cell (Bio-Rad). Membranes were blocked with 5% casein for 1 hr at room temperature and probed with monoclonal anti-ERK antibodies (E10 which recognises only phosphorylated ERK1/2 (New England BioLabs) and SC-1647 which recognises total ERKs, non-phosphorylated and phosphorylated (Santa Cruz Biotechnology). In some experiments, membranes were probed with polyclonal anti-ERK antibody (New England BioLabs) which also recognises total ERKs. Membranes were then washed three times in Tris buffered saline, containing 0.1% Tween and incubated with HRP-conjugated goat anti-mouse or goat anti-rabbit antibody. Blots were visualised by the enhanced chemi-luminescence detection system according to the manufacturer's instructions (Du Pont).

2.1.3 Integrin β-Subunit Immunoprecipitations

Tumour cells were harvested and divided into two equal aliquots based on cell counts. One aliquot was surface biotinylated and the cells lysed for integrin immunoprecipitations as described in Example 1.1.5, with the exception that three sequential rounds of immuno-precipitation were performed to deplete the lysates of integrin subunits β5 and β6. Lysis buffer was the same as that used for Western blotting. The other aliquot, intended for subsequent ERK2 immunoblotting to examine the effect of integrin immunodepletion on ERKs was not biotinylated but lysed immediately and divided into three samples each at a protein concentration of 1 mg/ml. Three sequential rounds of immunoprecipitation were performed against anti-β6 monoclonal antibody, R6G9 (using isotype matched antibody, IgG2A, and anti-β5 monoclonal antibody, P1F6, in control immunoprecipitations).

The integrin-depleted lysates were electrophoresed in 8% or 10% SDS-PAGE under non-reducing conditions and transferred to nitrocellulose membranes. Membranes were blocked with casein as for Western blotting and probed with anti-ERK monoclonal antibodies E10 and SC-1647. In parallel experiments, the sequentially immunoprecipitated β6 subunit bound to rabbit anti-mouse (RAM) coupled Sepharose B4 beads was also electrophoresed in 10% SDS-PAGE under non-reducing conditions, transferred to nitrocellulose membranes, and the membranes probed with anti-ERK monoclonal antibody E10 which recognises only phosphorylated forms of ERK1/2.

2.3 Results 2.3.1 Effect of Serum on MAP Kinase Activity

The effect of MEK (MAP kinase) inhibitors UO126 and PD98059 on MAP kinase activity in WiDr and HT29 wild-type cells was tested in the absence/presence of serum. Adherent cell monolayers on plastic were grown for 24 hrs in standard culture medium, then washed three times in PBS followed by 16 hrs in culture under serum-free conditions. Serum was then added for 30 min and MAP kinase activity assessed before and after addition of serum. The addition of serum markedly stimulated MAP kinase activity for both cell lines and was inhibitable by both MEK inhibitors.

2.3.2 Effect of Altered β6 Expression on MAP Kinase Activity Following Serum Stimulation.

In these experiments, WiDr transfectants (3 mock and 3 antisense β6 clones), HT29 transfectants (mock and antisense β6) and SW480 β6 transfectants (mock and sense β6) were serum-starved for 16 hrs followed by 30 mins exposure to serum. Increased expression of αvβ6 was associated with a marked increase in MAP kinase activity upon serum stimulation compared with cells lacking αvβ6 altogether (SW480 mock). Cells in which β6 expression had been down-regulated (antisense β6 transfectants) exhibited suppressed MAP kinase activity. Induced expression of β6 in the non-β6-expressing colon cancer cell line SW480 resulted in a three fold increase in serum-dependent MAP kinase activity.

2.3.3 αvβ6 Binds an Extracellular Signal-Related Kinase (ERK).

A highly surprising finding arising from phage display screening which underpins the present work is that the integrin β6 cytoplasmic domain binds a MAP kinase. Use of phage display to screen a $\gamma gt^{11}$ cDNA colon cancer cell library with the β6 cytoplasmic domain as bait yielded a clone which coded for ERK2 at the 3' end with 100% nucleotide sequence identity (across 393 bases) to the published sequence of ERK2 (Boulton et al, 1991). This putative association was investigated further.

Integrin immunoprecipitations were performed on equal protein loads of tumour cell lysates and the transferred proteins blotted with antibodies recognising phosphorylated and non-phosphorylated forms of ERK1/2. The specificity of this interaction was examined in integrin immunoprecipitations against β1, β5, β6 and αv integrin subunits. As shown in FIG. 10, the anti-ERK mAb'SC-1647 identified a β6-specific band migrating at the position of purified ERK2 protein. The integrin-associated ERK band was identified only in immunoprecipitations of the β6 subunit and its partner αv and not in immunoprecipitations of the β1/β5 subunits or in immunoprecipitations using isotype-matched control antibodies.

2.3.4 Effect of Altered β6 Expression on Total Cellular ERK and β6-Bound ERK.

Equal protein loads from one representative clone each from WiDr mock and antisense β6 transfectants were electrophoresed, transferred to nitrocellulose and blotted with anti-ERK mAb (SC-1647) as shown in FIG. 11(A). β6 immuno-precipitates from equal protein loads of the WiDr mock and antisense β6 clones were electrophoresed, transferred and probed with anti-ERK mAb (E10) as shown in FIG. 11(B). As indicated, suppression of β6 expression resulted in a reduction of both total cellular and phosphorylated integrin-associated ERK compared with WiDr mock transfectants. Similarly, β6 immunoprecipitations from SW480 β6 transfected clones expressing high and low levels of β6 (confirmed by FACScan and β6 immunoprecipitations) showed parallel changes in β6-bound phosphorylated ERK (FIG. 12).

2.3.5 Effect of β6 Immunodepletion on Total Cellular ERK and β6-Bound ERK

WiDr wild-type cells were surface biotinylated and the cell lysates immunodepleted of β6 in three rounds of sequential immunoprecipitation using anti-β6 mAb (R6G9) resulting in a marked loss of β6 from the lysates as shown in FIG. 13(A). β6-immunodepleted lysates were then transferred and blotted with anti-ERK1/2 antibody (SC-1647), which recognises both phosphorylated and non-phosphorylated forms of ERK1/2. As shown in FIG. 13(B), following three rounds of β6 immunodepletion, levels of ERK1/2 in β6-depleted lysates compared with non-immunodepleted lysates, were markedly reduced suggesting a significant contribution of β6-bound ERK to total cellular ERK. In contrast, immunodepletion of β5 by three successive rounds of immunoprecipitation with mAb P1F6 or isotype-matched control antibody IgG2A did not result in any reduction of cellular ERK levels compared with non-immunodepleted cell lysates.

2.3.6 Effect of ERK Immunodepletion on β6-Bound ERK

Cell lysates from WiDr wild-type cells were immunodepleted of ERK1/2 by means of sequential immunoprecipitations using the anti-ERK mAb, SC-1647. ERK-immunodepleted cell lysates probed with either E10 or SC-1647 mAbs contained markedly less ERKs. To examine the effect of ERK-immunodepletion on β6-bound ERK, the ERK-immunodepleted cell lysates were immunoprecipitated with anti-β6 mAb (R6G9) and the β6-immunoprecipitates probed with anti-ERK mAb (E10 recognising phosphorylated ERK1/2). ERK immunodepletion effectively reduced levels of β6-bound ERK.

2.3.7 Effect of Preventing Cell Attachment on αvβ6-Bound ERK

SW480 mock and β6 expressing transfected cells were grown to 80-90% confluency. Cells were washed twice with PBS and harvested after trypsinization. Cells were divided into three equal portions (approximately $4\times10^6$/batch). The first group was plated on a 75 $cm^2$ plastic flask in normal 10% serum containing medium (attached cells) while the other two groups were plated on 0.3% agarose underlay in serum free medium (non-attached cells). Cells were allowed to grow for 24 hours at 37° C., after which in one group of 0.3% agarose underlay, 15 ml of serum-free medium was added while in the other an equal volume of 10% serum-containing medium was added for 30 mins. Cells were collected washed with PBS and lysed in cell lysis buffer (100 mM Tris-HCl pH-7.5, 150 mM NaCl, 1 mM CaCl2, 1% Triton, 0.1% SDS, 0.1% Np-40, 1 mM vanadate, 1 μg/ml pepstatin, 1 mM PMSF, 5 μg/ml aprotonin and 1 μg/ml of leupeptin). 10 μl (10 μg of protein) was used for the analyses of cell lysates after adding equal volumes of non-reducing Laemmli buffer. For SW480-β6-transfected cells the rest of the cell lysate was used for immunoprecipitation of αvβ6 integrin. Cell lysates and β6 immunoprecipitates were subjected to western blotting and probed with E10 monoclonal antibody (recognising phosphorylated ERK1/2).

Cell lysates from the non-attached cells were found to require serum factors to maintain phosphorylation of total cellular ERK. In contrast, non-attached SW480 β6 colon cancer cells do not require serum factors to maintain the activation phosphorylation) state of β6-bound ERK.

2.3.8 Effect of PP2A Phosphatase on αvβ6-Bound ERK

In experiments to examine the effect of protein phosphatase 2A (PP2A) on β6-bound ERK, SW480 β6-transfected cells were sonicated in buffer comprising 5 mM Tric-HCl (pH 8.0), 10 mM $MgCl_2$ and 0.01 mM EGTA together with enzyme inhibitors, and cell lysates from both serum-starved and serum-induced cells treated with 0.5 units of PP2A (Promega) at 30° C. for 10 minutes. The reaction mixture was stopped by addition of equal volumes of non-reducing Laemmli sample buffer. In parallel, PP2A-treated cell lysates were immunoprecipitated with mAb R6G9 (anti-β6) followed by Western blot with anti-ERK mAb E10. MAP kinase activity assays were performed according to the manufacturer's instructions (Amersham Pharmacia Biotec) using $\gamma^{32}$P-ATP.

Exposure of cell lysates prepared from serum-supplemented and serum-starved cells to the PP2A catalytic subunit resulted in dephosphorylation of total ERK. In contrast, dephosphorylation of β6-bound ERK was not observed in β6 immunoprecipitates prepared from serum-supplemented or serum-starved cells β6 Bound ERK may therefore serve to maintain adjacent growth factor receptors in an activated state and thereby alter their sensitivity to exogenous co-factors.

2.3.9 Inhibition of MAP Kinase Activity Inhibits Secretion of Gelatinase B.

SW480 β6 transfectants were cultured under serum-free conditions for 48 hours in the absence/presence of the MEK inhibitor PD98059 (40 μM) or DMSO (vehicle control). Tumour-conditioned medium was assayed for gelatinase B by analysis of equal protein loads in a gelatin zymogram.

Inhibition of MAP kinase activity by the MEK inhibitor reduced gelatinase B secretion compared with controls.

2.3.10 β6-ERK2 Association in HaCaT and HaRas Cell Lines

β6 immunoprecipitates were prepared from human kerotinocyte cell lines (HaCaT and HaRas were obtained from Prof N. Fusenig, The German Cancer Research Institute, Heidelberg, Germany) using mAb R6G9 (anti-β6) and the immunoprecipitates probed with mab E10 (against phosphorylated ERK 1/2). FIG. 14 shows that ERK2 associates with β6 in both of HaCat and HaRas cells.

2.4 Discussion of Results

The MAP kinase pathway has been shown to be important in experimental tumour metastases (Mansour et al, 1994) and recent data implicate MAP kinases in tumour growth and invasiveness of colon cancer cells (Sebolt-Leopold et al, 1999). In the present study, up-/down-regulation of β6 expression in various colon cancer cell lines was shown to enhance/suppress respectively, MAP kinase activity. The presence of serum induced a three-fold increase in MAP kinase activity above that observed for serum-starved β6-expressing cells. In contrast, only a one-fold increase in serum-dependent MAP kinase activity was observed for cells in which β6 had been down-regulated consequent upon transfection with antisense β6. Moreover, induced expression of β6 in the non-β6-expressing colon cancer cell line SW480, was associated with a three-fold increase in serum-dependent MAP kinase activity. Serum contains a mixture of growth factors raising the possibility that one role for αvβ6 in colon cancer cells is to lower the threshold for activation of MAP kinase signalling pathways at times when the supply of serum-containing growth factors is limited.

The ERK band co-immunoprecipitated with β6 migrated either at or 1-2 kD higher than the mobility of purified phosphorylated ERK2 depending on the acrylamide concentration used in SDS-PAGE showing that the kinase does indeed, associate with the β6 subunit. Slight differences in mobility of the β6-associated ERK band compared with the pure ERK protein could arise if β6-bound ERK is hyper-phosphorylated and/or exists in an altered conformation consequent upon its association with β6. ERK bound to β6 may also be an alternatively spliced variant of ERK2 causing it to migrate differently. Finally, the purified ERK2 protein is derived from mouse which differs slightly from human ERK2 by being two amino acid residues shorter and also containing a single amino acid substitution.

In the present study, increased/decreased β6 expression in colon cancer cell lines was associated with increased/decreased β6-bound ERK, respectively. In addition, immunodepletion experiments suggest that β6-bound ERK makes a substantial contribution to total phosphorylated ERK within the cell and overall MAP kinase activity (see FIGS. 15(A) and 15(B)).

The observation that β6-mediated colon cancer growth in vitro is inhibitable by a matrix metalloproteinase inhibitor (Agrez et al, 1999) suggests that the increased gelatinase B secretion by β6-expressing colon cancer cells contributes to tumour progression. Taken together with the finding that inhibition of MAP kinase activity by the MEK inhibitor PD98059 diminished gelatinase B secretion in β6-expressing cells, it seems that activation of MAP kinase signalling plays a role, at least in part, in β6-mediated induction of gelatinase B secretion.

EXAMPLE 3

3.1 Identification of the Binding Domain on the β6 Subunit Cytoplasmic Tail Domain for ERK2

Peptide fragments corresponding to regions of the cytoplasmic tail domain of the β6 subunit were screened in an enzyme-linked immunosorbent assay (ELISA) for binding with ERK2. The 52 amino acid long β6 cytoplasmic tail is shown in FIG. 16 as are the amino acid sequences for the cytoplasmic domains of the β1 to β3 subunits. In particular, four synthetic peptides designated fragment 1 to fragment 4 were prepared and biotinylated at the N-terminal end of each, respectively (Auspep Pty Ltd, Melbourne Australia).

The region of the β6 tail to which each corresponds is indicated in FIG. 16 and set out below.

| | |
|---|---|
| Fragment 1: | HDRKEVAKFEAERSKAKWQTGT (SEQ ID NO: 17) |
| Fragment 2: | RSKAKWQTGTNPLYRGSTST (SEQ ID NO: 18) |
| Fragment 3: | NPLYRGSTSTFKNVTYKHRE (SEQ ID NO: 19) |
| Fragment 4: | FKNVTYKHREKQKVDLSTDS (SEQ ID NO: 20) |

The fragments overlap by 10 amino acids and are each 20 amino acids long with the exception of the fragment 1 with a length of 22 amino acids. Fragment 4 was synthesised with a terminal serine rather than a cysteine as found in wild-type β6 to avoid formation of a disulfide bridge between peptides.

Overlapping biotinylated fragments 1 to 4 were coated onto streptavidin coated polystyrene plates (Pierce, Rockford Ill. USA, Cat No. 15125) and the ELISA performed substantially according to manufacturers instructions. Briefly, wells are washed with 3×200 μl of wash buffer (TBS, 0.1% BSA, 0.05% Tween 20 or SuperBlock™ blocking buffer in TBS, Pierce, Prod. No. 37535) prior to addition of biotinylated peptides (100 μl) and incubation for 1 hr at room temperature to allow for capture of the peptides on the plate. Following another washing step, peptides were overlayed with GST-ERK, ERK (or JNK-1) alone at a volume of 100 μl per well, and the plates incubated for a further 1 hr at room temperature before removal of any unbound ERK by further washing.

Binding of ERK to the peptides is detected using 100 μl anti-ERK1/2 mAb SC1647 (Santa Cruz) as the primary antibody at a dilution of 1:700 (isotype matched antibody IgG2b is used as a control). This is followed by another washing step and addition of 100 μl rabbit anti-mouse antibody (Biorad) conjugated to alkaline phosphatase at a concentration of 1:1000 for 30 minutes again at room temperature. A 10 aliquot of detection reagent (alkaline phosphatase detection kit-Biorad) is then introduced into each well after a final washing step and allowed to react for 15-30 minutes at room temperature in the dark before absorbance is measured at 405 nm. All dilutions of peptides, MAP kinase and antibodies were performed using the wash buffer. GST-ERK is a fusion protein consisting of ERK coupled to glutathione-S-transferase and purified from host cells transfected with pGEX vector.

As shown in FIG. 17, significant binding of non-phosphorylated GST.ERK2 (0.25 μg/100 μl) to peptide fragment 2 was observed (1 μg/100 μl) while only negligible or low level binding for the other fragments was found.

Significant binding of non-phosphorylated ERK2 to both fragment 2 and β6 cytoplasmic tail peptide compared to fragments 1, 3 and 4 over a range of concentrations of ERK2 was also observed (see FIG. 18). Similar results were observed using a range of concentrations of the peptide fragments as shown in FIG. 19.

To further localise the binding domain on the cytoplasmic tail of the β6 subunit, progressively shorter peptides from the region of the β6 cytoplasmic tail corresponding to peptide fragment 2 were synthesised, biotinylated and the capacity to associate or otherwise bind to ERK2 assessed as described above. The binding of GST.ERK2 to a 15 mer test peptide (seq. 4) having the amino acid sequence RSKAKWQTGT-NPLYR (SEQ ID NO: 7) and a 10 mer test peptide having the sequence RSKAKWQTGT (SEQ ID NO: 21) is shown in FIG. 20 compared to fragment 2 over a range of concentrations of the peptides. As can be seen, no reduction in binding to the seq. 4 peptide compared to fragment 2 was found. Binding of ERK2 to the seq. 3 peptide was substantially less than that observed for seq. 4.

The region of the β6 tail to which each corresponds is indicated in FIG. 16 and set out below.

Fragment 1: HDRKEVAKFEAERSKAKWQTGT (SEQ ID NO: 22)

Fragment 2: RSKAKWQTGTNPLYRGSTST (SEQ ID NO: 23)

Fragment 3: NPLYRGSTSTFKNVTYKHRE (SEQ ID NO: 24)

Fragment 4: FKNVTYKHREKQKVDLSTDS (SEQ ID NO: 25)

The fragments overlap by 10 amino acids and are each 20 amino acids long with the exception of the fragment 1 with a length of 22 amino acids. Fragment 4 was synthesised with a terminal serine rather than a cysteine as found in wild-type β6 to avoid formation of a disulfide bridge between peptides.

A number of 10 mer biotinylated peptides corresponding to regions of fragment 2 or fragment 3 were then tested. The amino acid sequence for each peptide is as follows and their location in the β6 cytoplasmic domain is indicated in FIG. 21.

| | |
|---|---|
| 10(1): | NPLYRGSTST |
| 10(2): | WQTGTNPLYR |
| 10(3): | KFEAERSKAK |

The results are set out in FIG. 22 and show that GST.ERK binding to the 10 mer peptides is substantially reduced compared to binding to the seq. 4 peptide suggesting that opposite end regions of seq. 4 participate in the binding of ERK2.

Comparable binding of ERK2 to seq. 4 was found using a further 10 mer peptide identified as 10(4) in which amino acid sequence WQTGT of seq. 4 is omitted indicating that WQTGT is a linker sequence that does not participate directly in the binding of ERK to seq. 4. Negligible binding of ERK2 to the 5 mer peptide RSKAK was observed as shown in FIG. 23. ERK2 cleaved from GST-ERK2 by thrombin was used in this assay. Results (not shown) indicate that greater than a 3 fold increase in assay sensitivity can be achieved using thrombin cleaved ERK2 rather than GST-ERK2.

EXAMPLE 4

4.1 MAP Kinase JNK-1 Binds to the Cytoplasmic Tail Domain of β6

In view of the observation that ERK2 associates with the cytoplasmic tail of the β6 subunit, the MAP kinase JNK-1 was tested to evaluate whether it also could associate with the cytoplasmic tail of β6.

Briefly, 0.05-1.5 μm/100 μl of JNK-1 (Santa Cruz) was aliquoted into wells of a 96 well culture place containing increasing concentrations of the β6 cytoplasmic domain tail peptide used in Example 3. For comparison purposes, non-phosphorylated GST-ERK2 (0.05-1.5 μm/100 μl) was aliquoted into wells containing β6 cytoplasmic tail peptide or peptide fragments 1 or 2, respectively. Binding of JNK-1 was detected using mouse anti-JNK-1 mAb SC 474-G (Santa Cruz) and HRP-conjugated goat anti-mouse antibody. Absorbance was read at 405 nm and the results are shown in FIG. 24. Significant binding of JNK-1 to the β6 cytoplasmic tail peptide was found.

EXAMPLE 5

5.1 Evaluation of Ability of ERK2 to Bind to β6 Δ746-764 Deletion Mutant.

To examine the role of the amino acid sequence RSKAKWQTGTNPLYR (SEQ ID NO: 7) in the β6 cytoplasmic domain in situ, a β6 deletion construct lacking the coding sequence for EAERSKAKWQTGTNPLYRG (SEQ ID NO: 26) was transfected into colon cancer cell line SW480 which does not constitutively express the αVβ6 integrin using the calcium phosphate method previously described for transfections into this cell line (Agrez et al, 1994). The location of the β6 Δ746-764 deletion is indicated in FIG. 25. Construction of the β6 Δ746-764 deletion mutant in the vector pcDNA1neo and failure of the expressed receptor to localise to focal adhesions in Chinese hamster ovary cells has been reported (Cone et al, 1994). Facscan analysis revealed comparable levels of surface expression of mutant β6 to that seen for the full length wild-type receptor (see FIG. 26).

Equal protein loads of cell lysates prepared from SW480 cells were immunoprecipitated with either anti-β6 monoclonal antibody (mAb R6G9) or matched isotype control antibody. Surface biotinylation prior to immunoprecipitation confirmed equal surface expression of mutant and wild-type β6 (see FIG. 27(A). Aliquots of the immunoprecipitates were electrophoresed and transferred to nitrocellulose for Western blotting using monoclonal antibody E10 which recognises ERK1/2. As seen in FIG. 27(B), loss of the RSKAKWQTGTNPLYR (SEQ ID NO: 7) sequence in the β6 cytoplasmic domain reduced levels of β6-bound ERK by greater than approximately 75% of that observed for the wild type receptor.

EXAMPLE 6

6.1 Growth Inhibition Study.

HT29 and SW480 β6-expressing colon cancer cell lines were seeded into wells of 96-well microtitre plates (Nunclon) in Dulbecco's Modified Eagle's Medium (DMEM) supplemented with 10% foetal bovine serum, glutamine, Hepes, and antibiotics. Seeding cell densities were $3\times10^3$ cells per triplicate well for each condition tested and after 24 hours incubation of cell cultures in 5% $CO_2$, 100% humidity at 37° C., the culture medium was exchanged for serum-free DMEM medium supplemented with insulin, transferrin, selenous acid, hydrocortisone, non-essential amino acids, glutamine, Hepes and antibiotics containing either peptide RSKAKWQTGTNPLYR (SEQ ID NO: 7) alone or penetratin-peptide complex at a concentration of 10 μm for HT29 cells or 30 μm for SW480 β6-expressing cells. Cell cultures were incubated for a further 24 hours following which cultures were photographed (Kodak Techpan Film at 100 ASA setting) and the experiments terminated by addition of the cell proliferation reagent WST-1 (Boehringer Mannheim) to monitor effects of the peptide on cell growth. The cell proliferation reagent WST-1 is designed to be used for the non-radioactive, spectrophotometric quantification of cell growth and viability in proliferation and chemosensitivity assays. The colourmetric assay is based on the cleavage of the tetrazolium salt WST-1 by mitochondrial dehydrogenase in viable cells.

Specifically, at the termination of experiments, 30 μl of WST-1 was added to 270 μl culture medium volume in each microtitre well and the colour change quantitated in an ELISA plate reader by measuring absorbance of the formazan product at 450 mn (using a reference wavelength of more than 600 nm). The mean absorbance readings from triplicate wells (±standard error of the means) after subtraction of background control wells (culture medium without cells) was determined. Only the carrier penetratin-peptide complex was effective in inhibiting cell proliferation in contrast to either peptide or penetratin alone as shown in FIGS. 28 and 29 indicating that the penetratin-peptide complex was internalised by both the HT29 and SW480 cells resulting in the observed suppression of colon cancer growth. Photographs of the SW480 cells treated with penetratin alone or the penetratin-peptide complex are shown in FIGS. 30(A) to (C).

EXAMPLE 7

7.1 Growth Inhibition in SW480 Mock and SW480 β6 Transfectants.

SW480 mock and SW480 β6 transfectants were cultured in DMEM medium supplemented with 1% foetal bovine serum in the presence of 20 μM seq. 4 coupled to penetratin. Percentage inhibition was assessed by the WST-1 colorimetric dehydrogenase assay described in Example 6. The percentage inhibition of growth observed for the −β6 and +β6 expressing cells was 17% and 50%, respectively as indicated in FIG. 31A. The −β6 and +β cultured cells are shown in FIG. 31B.

EXAMPLE 8

The proliferation of SW480 cells expressing a β6 Δ746-764 deletion mutant was compared with non-β6 expressing SW480 cells and SW480 cells expressing full length wild-type β6. Cells were cultured for 10 days within a 3-dimensional collagen type I matrix. Collagen gels were prepared as bilayers (upper layer cell-containing and lower layer minus cells) in 24 well culture plates as previously described (Agrez, 1989; Agrez, 1994) except for the use of 5% foetal bovine serum as the supplement for DMEM. Colonies were photographed in the gel FIG. 32(A) at 10 days (bar represents 200μ) and following dissolution of the collagen with collagenase FIG. 32(B) prior to visual colony counting of all colonies exceeding 200μ in diameter within each well FIG. 32(C). As can be seen, significant proliferation of the SW480 cells expressing the full length wild-type β6 was observed compared to the non-β6 expressing cells and cells expressing the β6 Δ746-764 deletion mutant.

EXAMPLE 9

Growth inhibition of SW480 cells expressing full length wild-type β6 exposed to seq.4 coupled to penetratin or RSKAKWQTGTNPLYR (SEQ ID NO: 7) peptide coupled to penetratin (5, 10, 20, 30 μM in DMEM minus foetal bovine serum) but which peptide contained alanine substitutions at the four positions indicated was assessed. As shown in FIG. 33(A) and FIG. 33(B), progressive inhibition of proliferation in a dose-response manner was observed for the seq.4 penetratin complex compared with the alanine substituted peptide-penetratin complex which was without effect at all doses tested.

EXAMPLE 10

Binding of ERK2 to the seq.4 peptide (RSKAKWQTGTNPLYR) (SEQ ID NO: 7) was compared with peptides corresponding to regions of the cytoplasmic domain of integrin subunits β1, β2, β3 and β5. The amino acid sequences for those peptides is shown below:

β1 KFEKEKMNAKWDTGENPIYK (SEQ ID NO: 27)

β2 KEKLKSQWNNDNPLFK (SEQ ID NO: 28)

β3 RARAKWDTANNPLYK (SEQ ID NO: 29)

β5 RSRARYEMASNPLYR (SEQ ID NO: 30)

As shown in FIG. 34, significant binding of ERK2 to the seq. 4 peptide was observed. Binding of ERK2 to the β5 and β3 peptides was also found. The results have been corrected for non-specific binding and indicate a hierarchy of binding of ERK2 to integrin subunits.

EXAMPLE 11

Angiogenesis, the growth of new blood vessels, plays a role in diverse disease states including progression of cancer, diabetic retinopathy, rheumatoid arthritis, psoriasis, atherosclerosis, pregnancy and endometriosis. For examples, in cancers, the ability of microscopic tumour deposits to enlarge beyond 1-2 mms in diameter is dependent upon tumour-induced angiogenesis or sprouting of new host-derived blood vessels to nourish enlarging tumour cell nodules. The mitogen activated protein (MAP) kinase signalling pathway is critical for endothelial cell proliferation and new blood vessel formation. Moreover, a relationship exists between extracellular signal-regulated (ERK) kinase 1/2 activation and vascular endothelial growth factor (VEGF) expression with each activating the other (Gupta et al, 1999; Yu & Sato, 1999: Pages et al, 2000).

Two growth factor-dependant pathways of angiogenisis have now been shown to exist defined by their dependency on the distinct vascular integrins αvβ3 and αvβ5 (Friedlander et al, 1995: Eliceiri and Cheresh, 1999). It is noteworthy that the vascular system lacks αvβ6 expression (Breuss et al, 1993). Antibodies against αvβ5 and inhibition of protein kinase C signalling have both been shown to block VEGF-induced angiogenesis (Freidlander et al, 1995). The importance of αvβ5 in neovascularisation is further highlighted by the observation that β3 integrin-deficient mice exhibit normal blood vessel development in contrast to αv-deficient mice which implicates other beta integrin partners such as β5 (Eliceiri and Cheresh, 1999).

11.1 The β5 Integrin Subunit Binds ERK in Cells that Either Lack β6 or Express β6 Lacking the Binding Site for ERK2

The SW480 cell line expresses abundant αvβ5 but only minimal levels of αvβ3 and lacks αvβ1 and αvβ6. SW480 cells provide a model, therefore, with which to test whether the β5 integrin subunit can co-immunoprecipitate with ERK either in the absence of constitutive β6 expression or in the presence of β6 that lacks the binding site for ERK2 (RSKAKWQTGTNPLYR (SEQ ID NO: 7).

To evaluate this, cell lysates containing equal protein loads were prepared from SW480 wild-type cells and SW480 cells transfected with either vector alone (mock transfectants), wild type β6 or the β6 deletion mutant Δ746-764 (lacking the sequence EAERSKAKWQTGTNPLYRG (SEQ ID NO: 26), Cone et al, 1994). The lysates were immunoprecipitated with mAbs R6G9 (anti-β6), P1F6 (anti-β5) or murine IgG control antibody (mIgG). Western blotting of the immunoprecipitates with mAb E10 recognising phosphorylated ERK1 and 2 revealed no β5-bound ERK in the SW480 β6 transfectants expressing wild-type β6 in contrast to β5-associated ERK observed for the cell lines which either lack β6 or express the deletion mutant lacking the ERK2 binding sequence (FIGS. 35A and 35B). To determine whether β5 can bind ERK2 in vitro, a 15-mer peptide fragment derived from the β5 cytoplasmic domain corresponding to the ERK binding domain on β6 was tested for its ability to bind ERK2 in an ELISA.

In vitro MAP kinase activity assays were performed using a non-radioactive assay kit (Cell Signalling Technology, Beverley, Mass.) which measures phosphorylation of the ERK1 and 2 substrate Elk-1 presented as a fusion protein comprising the Elk-1 codons 307-428 coupled to GST. In the assay, ERK kinase is first immunoprecipitated from complete or integrin-immunodepleted soluble cell lysates and relative enzyme activity determined by the in vitro phosphorylation of GST-Elk-1.

Dose-dependant binding of the β5 fragment ($^{761}$RSRARYEMASNPLYR$^{775}$) (SEQ ID NO: 30) to ERK2 was observed as shown in FIG. 35C although less avidly than the 15-mer β6 peptide. In contrast, a synthetic peptide derived from the cytoplasmic domain of the β1 subunit ($^{765}$KFEKEKMNAKWDTGENPIYK$^{784}$) (SEQ ID NO: 27) which corresponds to the ERK binding domain on β6 failed to bind ERK2 (FIG. 35C).

11.2 The Increase in Cytosolic MAP Kinase Activity Upon Growth-Factor Stimulation is All Accounted for by β5-Bound ERK in Human Umbilical Vein Endothelial Cells that Lack β6

To determine the amount of ERK 1/2 activity associated with β5 following the activation of the MAP kinase pathway, the activity of ERK1/2 was compared in non-β5 immunodepleted lysates with that in β5 immunodepleted lysates derived from human umbilical vein endothelial cells (HUVECs) before and after stimulation with epidermal growth factor (EGF). Sequential immunodepletion of the β5 integrin subunit from cell lysates prepared from HUVECs results in total loss of all epidermal growth factor-induced MAP kinase (ERK 1/2) activity as determined by an Elk-1 phosphorylation assay (FIG. 36). Briefly, HUVECs were cultured in the absence/presence of 50 ng/ml epidermal growth factor (EGF) for 10 minutes after a prior 24 hour culture period in serum-free and growth factor-free medium. Bands show MAP kinase activity from immunodepleted cell lysates (anti-β5 or control IgG or anti-β6 immunodepletions, five rounds each) prepared from HUVECs before and after EGF stimulation. Non-phosphorylated and phosphorylated Elk-1 controls are shown in the left hand two lanes.

These results demonstrate that in β5-expression endothelial cells, the rise in cytosolic MAP kinase activity above basal levels upon EGF stimulation is completely accounted for by β5-bound ERK. The findings also indicate that a hierarchy of integrin-ERK2 interactions exists within cells specified by β6 over β5 in β6-expressing epithelial cells and β5 over other β integrins in endothelial cells.

Given the critical requirement of ERK1/2 activity in the process or angiogenesis and responsiveness of endothelial cells to various growth factors these findings show, for the first time, how the αvβ5 integrin may regulate angiogenesis through maintaining activated ERK at the plasma membrane. Accordingly, targeting the binding site on β5 for ERK2 or the binding site on ERK2 for the integrin offers a means of inhibiting new blood vessel formation. Moreover, the findings allow for anti-angiogenic therapies to benefit patients with a range of disorders including not only cancer, but also diabetic retinopathy, arthritis and other inflammatory conditions.

EXAMPLE 12

The β6 integrin immunodepletion/ERK immunoblotting experiments together with the antisense nucleic acid strategies reported herein show that the β6 integrin subunit contributes substantially to the total MAP kinase activity with for instance, colon cancer cells. Moreover, the fact β6-bound phosphorylated ERK2 is reduced by more than 75% in colon cancer cells lacking constitutive β6 expression stably transfected with a β6 deletion mutant in which the precise ERK2 binding domain is lacking, and that tumour growth is also reduced significantly compared with β6-expressing cells, shows that ERK2 plays a significant role in promoting cancer growth.

Accordingly, interruption of the β6-MAP kinase pathway has important implications not only for control of advanced colon cancer, but epithelial cancers in general given the wide expression of this integrin in other cancer types such as oropharyngeal, breast and ovarian cancer. Hence, identification of the ERK2 binding sequence to β6 facilitates the development of mimetics which interrupt the β6-MAP kinase growth-promoting axis in cancer.

12.1 ELISA Methodology for Determination of β6-Binding Domain in ERK2.

To determine the β6-binding domain(s) of ERK2, a biotinylated β6 cytoplasmic tail peptide spanning the cytoplasmic tail of β6 was incubated with a soluble ERK2 peptide fragment in a total incubation volume of 20 μl phosphate buffered saline (PBS). The mixture was stood for 45 minutes at room temperature (RT). Soluble ERK2 in PBS was then added and the solution left for a further 30 minutes. Following incubation the reaction volume was made to 400 μl with carbonate buffer (0.015 M $Na_2CO_3$ and 0.035M $NaHCO_3$ at pH 9.6) and 100 μl of this mixture added to each of 4 wells of a polystyrene ELISA plate (Nunc, Maxicorp). ERK2/peptides were allowed to attach to the plastic substrate for 18 to 20 hours at RT in the dark. After immobilisation the overlying buffer was flicked from the wells and excess solid surface blocked with casein (0.5% skim milk) in PBS for 60 minutes at RT. Wells were washed (×3) with was buffer (PBS plus 0.5% skim milk powder, 0.05% Tween-20) prior to incubation with the anti-β6 antibody SC-6632 (Santa Cruz) diluted 1:500 v/v in wash buffer (2 wells) or a control antibody (2 wells). Incubation with the primary antibody was carried out for 30 minutes at RT. The ELISA plate was flicked to remove the antibody mixture before washing 3 times with wash buffer. Wells were then incubated with anti-species alkaline phosphatase (AP) conjugated antibody (1:2000 v/v in wash buffer) for 30 minutes at RT, flicked and washed as above. Specific binding events were quantitatively determined using a colourimetric substrate system by measuring absorbency at 405 mm (Bio-Rad, AP substrate kit).

12.2 Identification of β6-Binding Domain of ERK2.

In a preliminary study, ERK peptides were probed in small groups to identify a possible ERK2 competing peptide that binds with the β6 cytoplasmic tail peptide. Overlapping ERK2 peptides 1 to 14 comprising the full length ERK2 sequence (360 amino acids) were utilised, and an inhibitory effect on β6-ERK2 binding was identified within the group comprising peptides 7, 8, and 9 (data not shown). The amino acid sequences for the peptides and position within ERK2 are shown below.

1. MAAAAAAGAGPEMVRGQVFDVGPRYTNLSY (SEQ ID NO: 31)
2. YTNLSYIGEGAYGMVCSAYDNVNKVRVAIK (SEQ ID NO: 32)
3. VRVAIKKISPFEHQTYCQRTLREIKILLRF (SEQ ID NO: 33)
4. KILLRFRHENIIGINDIIRAPTIEQMKDVY (SEQ ID NO: 34)
5. QMKDVYIVQDLMETDLYKLLKTQHLSNDHI (SEQ ID NO: 35)

-continued

6. LSNDHICYFLYQILRGLKYIHSANVLHRDLK (SEQ ID NO: 36)
7. HRDLKPSNLLLNTTCDLKICDFGLAR (SEQ ID NO: 1)
8. DFGLARVADPDHDHTGFLTEYVATRWYRAPEIMLNSKGY (SEQ ID NO: 37)
9. NSKGYTKSIDIWSVGCILAEMLSNRPIFPG (SEQ ID NO: 38)
10. PIFPGKHYLDQLNHILGILGSPSQEDLNCI (SEQ ID NO: 39)
11. DLNGIINLKA RNYLLSLPHKNKVPWNRLFP (SEQ ID NO: 40)
12. NRLFPNADSKALDLLDKMLTFNPHKRIEVE (SEQ ID NO: 41)
13. RIEVEQALAHPYLEQYYDPSDEPIAEAPFK (SEQ ID NO: 42)
14. EAPFKFDMELDDLPKEKLKELIFEETARFQPGYRS (SEQ ID NO: 43)

Individual overlapping peptides of the ERK2 sequence were then tested at equimolar concentrations for the ability to inhibit the β6-ERK interaction. Only peptide 7 (HRDLKPSNLLLNTTCDLKICDFGLAR) (SEQ ID NO: 1)) was found to be effective (see FIG. 37). Repeat testing using adjacent ERK2 overlapping peptides as controls yielded the same result (see FIG. 38).

Importantly, β6 bound to ERK2 does not interfere with ERK2 binding to the well, thereby confirming the validity of the ERK2 peptide competition assay. To optimise the assay, β6 cytoplasmic tail peptide was incubated at increasing concentrations with ERK2. Maximal β6 detected when bound to ERK was found to be at a concentration of 0.25 μM (data not shown).

β6 cytoplasmic tail peptide (0.25 μM) was then either pre-incubated with ERK peptides 2, 7, 8 or 10 in the competition assay or directly with ERK2 (positive control). An inhibition of 83% for β6-ERK2 binding was again demonstrated for sequence 7 (see FIG. 39). To demonstrate that neither β6 alone or ERK2 peptide fragments 2, 7, 8 and 10 interfered with ERK2 binding to the plate, parallel samples of each condition identified in FIG. 38 were probed with anti-ERK2 antibody. None of the peptide or β6 coincubations with ERK2 interfered with ERK binding to the ELISA plate.

EXAMPLE 13

13.1 Induction of Wound Healing Response

Keratinocytes in vivo in unwounded skin do not express β6 integrin but do so after sub-culturing in vitro. Hence, to avoid the conflicting presence of integrin αvβ6, the epithelial cell line SW480 which lacks αvβ6 expression was chosen in order to examine the effect of peptide β6 agonists on cell migration following artificial wounding in vitro.

The wound assay was performed by seeding $2\times10^5$ cells into 24 well (1.6 cm diameter) tissue culture plates in Dulbecco's modified Eagles medium (DMEM) supplemented by 10% foetal calf serum, HEPES, glutamine and antibiotics. The confluent cell monolayers were streaked with the tip of a plastic pipette in a cross-wire fashion, and loose non-adherent cells washed off gently with medium before replacing the culture medium with DMEM supplemented with 1% foetal calf serum. In addition, RSKAKWQTGTNPLYR (SEQ ID NO: 7) peptide ligated to penetratin (carrier peptide) by means of cysteine Cys (Npys) bonding was added to each well at a final concentration in the range of 1.25-10 μM. Cell migration across the wounded (streaked) area was photographed (Techpan, Kodachrome, ASA100) after a further 48 hours in culture. As shown in FIGS. 40A to 40D, a dose-dependent wound repair process (enhanced cell migration) was observed for the peptide-agonist complexed with the intracellular delivery vehicle penetratin. The conditions utilised in the assay were as follows: A: no peptide-penetratin complex added, B: 2.5 μM peptide-penetratin complex added, C: 5 μM peptide-penetratin complex added, D: 10 μM peptide-penetratin complex added.

Cell migration was not stimulated by either the peptide-agonist uncoupled to penetratin or penetratin alone (not shown). The bar length shown in FIG. 40D represents 80 μM in length.

13.2 Discussion

The activity of ERK2 is tightly regulated. Dual phosphorylation events, one on residue 185 (Y) and one on residue 183 (T) are required for ERK2 activation (Zhang et al, 1995). In unphosphorylated ERK2, Y185 is found largely buried within the molecule whereas T183 is exposed.

In particular, the phosphorylation lip of ERK2 consists of 15 amino residues from residue 173 (D) to residue 187 (A) namely DPDHDHTGFLTEYVA (SEQ ID NO: 44). This sequence is near the mouth of the active site (Zhang et al, 1995).

The 26 mer peptide fragment of ERK2 (peptide 7) found to inhibit binding of β6 cytoplasmic domain to ERK2 stretches from amino acid residue 145 (H) to residue 170 (R). This inhibitory binding sequence lies adjacent to the phosphorylation lip of ERK2. The reason for low stability of the phosphorylation lip in ERK2 is uncertain, but may be due to the unusual cluster of three positively charged amino acids namely residue 146 (R), 170 (R) and 201 (K) (Zhang et al, 1995). Residues 146 (R) and 170 (R) of ERK2, both of which are included within peptide 7, appear to be conserved among many serine/threonine specific kinases. For conserved amino acid residue 146 (R) to bind to a phosphate ion, it must lose its interaction with the backbone of the loop defined by amino acid residues 199 to 205 of ERK2 adjacent to the phosphorylation lip (residues 173 (D) to 187 (A)). Accordingly, β6 may bind to the 15 mer PSNLLLNTTCDLKIC (SEQ ID NO: 2) within peptide 7 and break the interaction between residue 146 (R) and the backbone loop allowing ERK to be phosphorylated on residue 183 (T) and 185 (Y).

Although the present invention has been described hereinbefore with reference to a number of preferred embodiments, the skilled addressee will understand that numerous variations and modifications are possible without departing from the scope of the invention.

REFERENCES CITED

Agrez, M. V. and Bates R. C., Colorectal cancer and the integrin family of cell adhesion receptors: current status and future directions. European Journal of Cancer 30A, 2166-2170 (1994).

Agrez, M. V., Human colon cancer and fibroblast cell lines cultured in and on collagen gels. Aust. N. Z. J. Surg. 59, 415-420 (1989).

Agrez, M. V., Bates R. C., Mitchell, D., Wilson, N., Ferguson, N., Anseline, P. and Sheppard. D., Multiplicity of fibronectin-binding αv integrin receptors in colorectal cancer. Br. J. Cancer 73, 887-892 (1996).

Agrez, M. V., Cell adhesion molecules and colon cancer. A. N. Z. J. Surgery. 66, 789-796 (1996).

Agrez, M. V., Chen, A., Cone, R. I., Pytela, R. and Sheppard, D., The αvβ6 integrin promotes proliferation of colon carcinoma cells through a unique region of the β6 cytoplasmic domain. J. Cell Biol. 127, 547-556 (1994).

Agrez, M. V., Gu, X., Turton, J., Meldrum, C., Niu, J., Antalis, T. and Howard, E. W., The αvβ6 integrin induces gelatinase B secretion in colon cancer cells. Int. J. Cancer 81, 90-97 (1999).

Bachmann, A. S., Surovoy, A., Jung, G. and Moelling, K, Integrin receptor-targeted transfer peptides for efficient delivery of antisense oligodeoxynucleotides. J. Mol. Med. 76, 126-132 (1998).

Berkner, Curr. Top. Microbiol. Immunology 158, 39-61 (1992).

Bookstein, R., Demers, W., Gregory, R., et al, p53 gene therapy in vivo for hepatocellular and liver metastatic colorectal cancer. Seminars Oncol. 23, 66-77 (1996)

Boudreau, N., Sympson, C. J., Werb, Z. and Bissell, M., Suppression of ICE and apoptosis in mammary epithelial cells by extracellular matrix. Science 267, 891-893 (1995).

Boulton, T. G., Nye, S. H. and Robbins, D. J., ERKs: a family of protein-serine/threonine kinases that are activated and tyrosine phosphorylated in response to insulin and NGF. Cell 65, 663-675 (1991).

Breakfield and Geller, Mol. Neurobiol. 1, 337-371 (1987).

Breuss, J. M., Gallo, J., De Lisser, H. M., Klimanskaya, I. V., Folkesson, H. G., Pittet, J. F., Nishimura, S. L., Aldape, K., Landers, D. V., Carrenter, W., Gillet, N., Sheppard, D., Mathay, M., Albeda, S. M., Kramer, R. H., and Pytela, R., Expression of the β6 integrin in development, neoplasia and tissue repair suggests a role in epithelial remodelling. J. Cell Sci. 108, 2241-2251 (1995).

Breuss, J. M., Gillet, N., Lu, L., Sheppard, D. and Pytela, R., Restricted distribution of integrin beta 6 mRNA in primate epithelial tissues. J. Histochem. Cytochem. 41, 1521-1527 (1993).

Brooks, P. C., Montgomery, A. M. P., Rosenfeld, M., Reisfeld, R. A., Hu, T., Klier, G. and Cheresh, D. A., Integrin alpha v beta 3 antagonists promote tumor regression by inducing apoptosis of angiogenic blood vessels. Cell 79, 1157-1164 (1994).

Brooks, P. C., Stromblad, S., sanders, L. C., von Schalscha, T. L., Aimes, R. T., Stetler-stevenson, W. G., Quigley, J. P. and Cheresh, D. A., Localization of matrix metalloproteinase MMP-2 to the surface of invasive cells by interaction with integrin αvβ3. Cell 85, 683-693 (1996).

Busk, M., Pytela, R. and Sheppard, D., Characterisation of the αvβ6 as a fibronectin-binding protein. J. Biol. Chem. 267, 5790-5796 (1992).

Chen, Q., Kinch, M. S. and Lin, T. H., Integrin-mediated cell adhesion activates mitogen-activated protein kinases. J. Biol. Chem. 269, 26602-26605 (1994).

Chomczynski, P. and Sacchi, N., Single-step method of RNA isolation by acid guanidium thiocyanate-phenol-chloroform extraction. Anal. Biochem. 162, 156-159 (1987).

Clark, R. A., Ashcroft, G. S., Spencer, M. J., Larjava, H. and Ferguson, M. W., Re-epithelialization of normal human excisional wounds is associated with a switch from alpha v beta 5 to alpha v beta 6 integrins. Br. J. Dermatol. 135, 46-51 (1996).

Cone, R. I., Weinacker, A., Chen, A. and Sheppard, D., Effects of beta subunit cytoplasmic domain deletions on the recruitment of the integrin alpha v beta 6 to focal contacts. Cell Adhes. Comm. 2, 101-113 (1994).

Coppolino, M., Leung-Hagesteijn, C. Dedhar, S. and Wilkins, J., Inducible interaction of integrin alpha 2 beta 1 with calreticulin. Dependence of the activation state of the integrin. J. Biol. Chem. 270, 23132-23138 (1995).

Dedhar, S. and Hannigan, G. E., Integrin cytoplasmic interactions and bidirectional transmembrane signalling. Curr. Opin. Cell Biol. 8, 657-669 1996).

Dedhar et al., J. Cell. Biol. 104, 585 (1997).

Derossi, D., Calvet, S., Trembleau, A., et al, Cell internalization of the third helix of the Antennapedia homeo domain is receptor-independent. J. Biol. Chem. 271, 18188-18193 (1996).

Derossi, D., Joliot, A. H., Chassaing, G. and Prochiantz, A., The third helix of the Antennapedia homeodomain translocates through biological membranes. J. Biol. Chem. 269, 10444-10450 (1994).

Eliceira B. P. and Cheresh D. A., The role of αv integrins during angiogenesis: insights into potential mechanisms of action and clinical development. J. Clin Invest. 103 (9): 1227-30 (1999).

Felding-Habermann, B., Mueller, B. M., Romerdahl, C. A. and Cheresh, D., Involvement of integrin αv gene expression in human melanoma tumorigenicity. J. Clin. Invest. 89, 2018-2022 (1992).

Fink et al., Hum. Gene Ther. 3, 11-19 (1992).

Freese et al., Biochem. Pharmacol. 40, 2189-2199 (1990).

Friedlander M, Brooks P. C., Shaffer R. W., Kincaid C. M., Varner J. A., Cheresh D. A., Definition of two angiogenic pathways by distrinct αv integrins. Science. 270(5241): 1500-2 (1995).

Gamble, J. R., Matthias, L. J., Meyer, G., Kaur, P., Russ, G., Faull, R., Berndt, M. C. and Vadas, M. A., Regulation of in vitro capillary tube formation by anti-integrin antibodies. J. Cell Biol. 121, 931-43 (1993).

Garrington, T. P., and Johnson, G. L., Organization and regulation of mitogen-activated protein kinase signaling pathways. Curr. Opin. Cell Biol. 11, 211-218 (1999).

Giancotti, F. G. and Ruoslahti, E., Integrin signalling. Science 285, 1028-1032 (1999).

Gorgziglia and Kapikian, J. Virol. 66, 4407-4412 (1992).

Grammer, T. C. and Blenis, J., Evidence for MEK-independent pathways regulating the prolonged activation of the ERK-MAP kinases. Oncogene 14, 1635-1642 (1997).

Guan, J. L. and Shalloway, D., Regulation of focal adhesion-associated protein tyrosine kinase by both cellular adhesion and oncogenic transformation. Nature 358, 690-692 (1992).

Gupta, K., Kshirsagar, S., Li, W., Gui, L., Ramakrisban, S., Gupta, P., Law, P. Y., Hebbel, R. P., VEGF prevents apoptosis of human microvascular endothelial cells via opposing effects on MAPK/ERK and SAPK/JNK signalling. Exp Cell Res. 247(2): 495-504 (1999).

Haapasalmi, K., Zhang, K, Tonneson, M., Olerud, J., Sheppard, D., Salo, T., Kramer, R., Clark, R. A. F., Uitlo, V-J. and Larjava, H., Keratinocytes in human wounds express avb6 integrin. J. Invest. Dermatol. 106, 42-48 (1996).

Hannigan, G. E., Leung-Hagesteijn, C., Fitz-Gibbon, L., Coppolino, M. G., Radeva, G., Filmus, J., Bell, J. C. and Dedhar, S., Regulation of cell adhesion and anchorage-dependent growth by a new beta 1-integrin-linked protein kinase. Nature 379, 91-96 (1996).

He, T-C., Zhou, S., Da Costa, L. T., Yu, J., Kinzier, K. W. and Vogelstein, B. A simplified system for generating recombinant adenoviruses. Proc., Natl. Acad. Sci. USA 95, 2509-2514 (1998).

Hemler, M. E., Integrin associated proteins. Curr. Opin. Cell Biol. 10, 578-585 (1998).

Hergott, G. J., Nagai, H. and Kalnins, V. I., Inhibition of retinal pigment epithelial cell migration and proliferation with monoclonal antibodies against the beta 1 integrin subunit during wound healing in organ culture. Invest. Ophthalmol. Vis. Sci. 34, 2761-2768 (1993).

Horwitz, A., Duggan, K., Buck, C., Beckerle, M. C. and Burridge, K., Interaction of plasma membrane fibronectin receptor with talin-a transmembrane linkage. Nature 320, 531-533 (1986).

Howe, A., Aplin, A. E., Alahari, S. K and Juliano, R. L., Integrin signaling and cell growth control. Curr. Opin. Cell Biol. 10, 220-231 (1998)

Hynes, R. O., Integrins: versatility, modulation and signaling in cell adhesion. Cell 69, 11-25 (1992).

Johnson et al., J. Virol. 66, 2952-2965 (1992).

Jones, J., Watt, F. M. and Speight, P. M., Changes in the expression of alpha v integrins in oral squamous cell carcinomas. J. Oral Path. & Med. 26, 63-68 (1997).

Klemke, R, L., Cai, S. Giannini, A. L., Gallagher, P. J., de Lanerolle, P. and Cheresh, D. A., Regulation of cell motility by mitogen-activated protein kinase. J. Cell Biol. 137, 481-492 (1997).

Knezevic, I., Leisner, T. M. and Lam, S C-T., Direct binding of the platelet integrin alpha IIb beta 3 (GPIIb-IIIa) to talin. Evidence that interaction is mediated through the cytoplasmic domains of both alpha IIb and beta 3. J. Biol. Chem. 271, 16416-16421 (1996).

Kohler G and Milstein C. Continuous cultures of fused cells secreting antibody of predefined specificity. Nature 256, 495-497 (1975).

Kornberg, L., Earp, H. S., Parsons, J. T., Schaller, M. and Juliano, R. L., Cell adhesion or integrin clustering increases phosphorylation of a focal adhesion-associated tyrosine kinase. J. Biol. Chem. 267, 23439-23442 (1992).

Kraft, S., Dienfenbach, B., Mebta, R., Jonczyk, A., Luckenbach, G. A. and Goodman, S. L., Definition of an unexpected ligand recognition motif for αVβ6 integrin. J. Biol. Chem. 274 (4) 1979-1985 (1999).

Lengauer, C., Kinzler, K. W. and Vogelstein, B., Genetic instability in colorectal cancers. Nature 386, 623-7 (1997).

Licato, L. L., Keku, T. O. and Wurzelmann, J. I., In vivo activation of mitogen-activated protein kinases in rat intestinal neoplasia. Gastroenterology 113, 1589-1598 (1997).

Lindberg, F. P., Gresham, H. D., Reinhold, M. I. and Brown, E. J., Integrin-associated protein immunoglobulin domain is necessary for efficient vitronectin bead binding. J. Cell Biol. 134, 1313-1322 (1996).

Liu, S., Thomas, S. M., Woodside, D. G., Rose, D. M., Klosses, W. B., Pfaff, M. and Ginsberg, M. H., Binding of paxillin to alpha 4 integrins modifies integrin-dependent biological responses. Nature 402, 676-680 (1999).

Lo C. W., Transformation by iontophoretic microinjection of DNA: Multiple integrations without tandem insertions. Mol. Cell. Biol. 3, 1803 (1983).

Loftus, J. C., Smith, J. W. and Ginsberg, M. H., Integrin-mediated cell adhesion: the extracellular face. J. Biol. Chem. 269, 25235-25238 (1994).

Madzak et al., J. Gen. Virol. 73, 1533-1536 (1992).

Mainiero, F., Murgia, C., Wary, K. K., Curatoia, A. M., Pepe, A., Blumemberg, M., Westwick, J. K., Der, C. J. and Giancotti, F. G., The coupling of alpha 6 beta 4 integrin to Ras-MAP kinase pathways mediated by Shc controls keratinocyte proliferation. EMBO J. 16, 2365-2375 (1997).

Maniero, F., Pepe, A., Wary, K. K., Spinardi, L., Mohammadi, M., Schiessinger, J. and Giancotti F. G., Signal transduction by the alpha 6 beta 4 integrin: distinct beta 4 subunits mediate recruitment of Shc/Grb2 and association with the cytoskeleton of hemidesmosomes. EMBO J. 14, 4470-4481 (1995).

Mansour, S. J., Matten, W. T., Hermann, A. S., Candia, J. M., Rong, S., Fukasawa, K., Vande-Woude, G. F. and Ahn, N. G., Transformation of mammalian cells by constitutively active MAP kinase kinase. Science 265, 966-670 (1994).

Margoiskee, Curr. Top. Microbiol. Immunol. 158, 67-90 (1992).

Meredith, J. E. Jr, Fazeli, B. and Schwartz, M. A., The extracellular matrix as a cell survival factor. Mol. Biol. Cell 4, 953-961 (1993).

Miller, Current. Top. Microbiol. Immunol. 158, 1-24 (1992).

Miranti, C. K., Ohno, S. and Brugge, J. S., Protein Kinase C regulates integrin-induced activation of the extracellular regulated kinase pathway upstream of Shc. J. Biol. Chem. 274, 10571-10581 (1999).

Montgomery, A. M. P., Reisfeld, R. A. and Cheresh, D. A., Integrin αvβ3 rescues melanoma cells form apoptosis in three-dimensional dermal collagen. Proc. Natl. Acad. Sci. USA 91, 8856-8860 (1994).

Moss, Curr. Top. Microbiol. Immunol. 158, 25-38 (1992).

Munger, J. S., Huang, X., Kawakatsu, H., Griffiths, M. J. D., Dalton, S. L., Wu, J., Pittet, J. F., Kaminski, N., Garat, C., Matthoy, M. A., Rifkin, D. B. and Sheppard, D., The integrin avb6 binds and activates latent TGFb1: a mechanism for regulating pulmonary inflammation and fibrosis. Cell 96, 319-328 (1999).

Muzyczka, Curr. Top. Microbiol. Immunol. 158, 97-123 (1992).

Otey, C. A., Pavalko, F. M. and Burridge, K., An interaction between alpha-actinin and the beta 1 integrin subunit in vitro. J. Cell Biol. 111, 721-729 (1990).

Pages, G., Milanini, J., Richard, D. E., Berra, E., Gothie, E., Vinals, F., Pouyssegur, J., Signalling angiogenesis via p42-p44 MAP kinase cascade. Ann N Y Acad. Sci. 902: 187-200 (2000).

Payne, D. M., Rossomando, A. J., Martino, P., et al, Identification of the regulatory phosphorylation sites in pp42/mitogen-activated protein kinase (MAP kinase). EMBO J. 10, 885-892 (1991).

Petropoulos et al., J. Virol. 66, 3391-3397 (1992).

Pfaff, M., Liu, S., Erle, D. J., Ginsberg, M. H., Integrin beta cytoplasmic domains differentially bind to cytoskeletal proteins. J. Biol. Chem. 273, 6104-6109 (1998).

Reszka, A. A., Hayashi, Y. and Horwitz, A. F., Identification of amino acid sequences in the integrin beta 1 cytoplasmic domain implicated in cytoskeletal association. J. Cell Biol. 117, 1321-1330 (1992).

Rojiani, M. V., Finlay, B. B., Gray, V. and Dedhar, S., In vitro interaction of a polypeptide homologous to human Ro/SS-A antigen (calreticulin) with a highly conserved amino acid sequence in the cytoplasmic domain of integrin alpha subunits. Biochemistry 30, 9859-9866 (1991).

Schaller, M. D., Otey, C. A., Hilderbrand, J. D. and parsons, J. T., Focal adhesion kinase and paxillin bind to peptides mimicking beta integrin cytoplasmic domains. J. Cell Biol. 130, 1181-1187 (1995).

Schiller et al. Int. J. Pept. Prot. Res. 25, 175 (1985).

Schlaepfer, D. D., Hanks, S. K., Hunter, T. and van der Geer, P., Integrin-mediated signal transduction linked to Ras pathway by GRB2 binding to focal adhesion kinase. Natural 372, 786-791 (1994).

Schneller, M., Vuori, K. and Ruoslahti, E., alpha v beta 3 integrin associates with activated insulin and PDGF beta receptors and potentiates the biological activity of PDGF. EMBO J. 16, 5600-5607 (1997).

Sebolt-Leopold, J. S., Dudley, D. T. and Herrera, R., Blockade of the MAP kinase pathway suppresses growth of colon tumors in vivo. Nature Med. 5, 810-816 (1999).

Sheppard, D., Rozzo, C., Starr, L., Quaranta, V., Erie, D. J. and Pytela, R., Complete amino acid sequence of a novel integrin β subunit (β6) identified in epithelial cells using the polymerase chain reaction. J. Biol. Chem. 265, 11502-11507 (1990).

Shimada, J. Clin. Invest. 88, 1043-1047 (1991).

Smythe, W. R, Lebel, E., Bavaria, J. E., Kaiser, L. R. and Albelda, S. M., Integrin expression in non-small cell carcinoma of the lung. Cancer & Metastasis Reviews 14, 229-239 (1995).

Spitz, F. R., Nguyen, D., Skibber, J. M., et al, In vivo adenovirus-mediated p53 tumor suppresor gene therapy for colorectal cancer. Anticancer Res. 16, 3415-3422 (1996).

Stein C. A., and Cohen J. S., Oligodeoxynucleotides as inhibitors of gene expression: A review. Cancer Res. 48(10), 2659-2668 (1998).

Takayama, K., Ueno, H., Pei, X. H., et al, The levels of integrin alpha v beta 5 may predict the susceptibility to adenovirus-mediated gene transfer in human lung cancer cells. Gene Ther. 5, 361-368 (1998).

Takiuchi, H., Kanokogi, M., Fujimoto, N., Hanafusa, T., Kyo, M., Ichikawa, Y., Nagano, S., Fukunisbi, T., Yabumoto, H. and Ihara, H., Expression of integrin molecule in urological tumour cell lines by using RT-PCR method. Jap. J. Urology 85, 584-588 (1994).

Thomas, G. J., Jones, J. and Speight, P. M., Integrins and oral cancer. Oral Oncology 33, 381-388 (1997).

Thomas, J. W., Mathias, P., Cheresh, D. A. and Nemeron, G., Integrins alpha v beta 3 and alpha v beta 5 promote adenovirus internalisation but not virus attachment. Cell 73, 309-319 (1993).

Thompson S., Clark A. R., Pow A. M., Hooper M. L., and Melton D. W., Germ line transmission and expression of a corrected HPRT gene produced by gene targeting in embryonic stem cells. Cell 27, 56 (2) 313-321 (1989).

Van der Krol A. R., Mol J. N., and Stuitje A. R., Modulation of eukaryotic gene expression by complementary RNA or DNA sequences. Biotechniques 6, 958-976 (1998).

Van der Putten H., Botteri F. M., Miller A. D., Rosenfeld M. G., Fan H., Evans R. M., and Verma I. M., Efficient insertion of genes into the mouse germ line via retroviral vectors. Proc. Natl. Acad. Sci. USA. 82, 6148 (1988).

Varner, J. A., Emerson, D. A. and Juliano, R. L., Integrin alpha 5 beta 3 expression negatively regulates cell growth: reversal by attachment to fibronectin. Mol. Biol. Cell 6, 725-740 (1995), Wang, A., Yokosaki, Y., Ferrando, R., Balmes, J. and Sheppard, D., Differential regulation of airway epithelial integrins by growth factors. Am. J. Respira. Cell & Mol. Biol. 15, 664-672 (1996).

Wary, K. K., Mainiero, F., Isakoff, S. J., Marcantonio, E. E. and Giancotti, F. G., The adaptor protein Shc couples a class of integrins to the control of cell cycle progression. Cell 87, 733-743 (1996).

Weinacker, A., Ferrando, R., Elliott, M. Hogg, J., Balmes, J. and Sheppard, D., Distribution of integrins alpha v beta 6 and alpha 9 beta 1 and their known ligands, fibronectin and tenascin, in human airways. Am. J. Respira. Cell & Mol. Biol. 12, 547-556 (1995).

Widmann, C., Gibson, S., Jarpe, B and Johnson, G. L., Mitogen-activated protein kinase: conservation of a three-kinase module from yeast to human. Phys. Rev. 79, 143-180 (1999).

Williams, E. J., Dunican, D. J., Green, P. J., Howell, F. V., Derossi, D., Walsh, F. S. and Doherty, P., Selective inhibition of growth factor-stimulated mitogenesis by a cell-permeable Grb2-binding peptide. J. Biol. Chem. 272, 22349-22354 (1997).

Yu, Y. and Sato J. D., MAP kinases, phosphatidylinositol 3-kinase, and p70 S6 kinase mediate the mitogenic response of human endothelial cells to vascular endothelial growth factor. J Cell Physiol. 178(2): 235-46 (1999).

Zambruno, G., Marchisio, P. C., Marconi, A., Vaschieri, C., Melchiori, A., Giannetti, A. and De Luca, M., Transforming growth factor—β1 modulates β1 and β5 integrin receptors and induces the de novo expression of the αvβ6 heterodimer in normal human keratinocytes: implications for wound healing. J. Cell Biol. 129, 853-865 (1995).

Zhu, X. and Assoian, R. K., Integrin-dependent activation of MAP kinase: a link to shape-dependent cell proliferation. Mol. Biol. Cell 6, 273-282 (1995).

The invention claimed is:

1. An isolated or purified polypeptide consisting of the amino acid sequence HRDLKPSNLLLNTTCDLKICDFGLAR (SEQ ID NO: 1), or a variant form of said amino acid sequence having greater than 80% sequence identity with SEQ ID NO: 1 that binds to a binding domain of a β6 integrin subunit for extracellular signal-regulated kinase-2 (ERK2), or a fragment of said amino acid sequence having 10 to 25 amino acids of SEQ ID NO: 1 that binds to a binding domain of a β6 integrin subunit for ERK2.

2. A fusion protein incorporating a polypeptide consisting of the amino acid sequence HRDLKPSNLLLNTTCDLKICDFGLAR (SEQ ID NO: 1), or a variant form of said amino acid sequence having greater than 80% sequence identity with SEQ ID NO: 1 that binds to a binding domain of a β6 integrin subunit for extracellular signal-regulated kinase-2 (ERK2), or a fragment of said amino acid seciuence having 10 to 25 amino acids of SEQ ID NO: 1 that binds to a binding domain of a β6 integrin subunit for ERK2, the polypeptide being coupled to adjoining amino acids thereby forming a chimeric sequence.

3. A fusion protein according to claim 2 further comprising a moiety for facilitating the passage of the polypeptide across the cell membrane of the cell.

4. A fusion protein according to claim 2 further comprising a protease cleavage site allowing release of the polypeptide after passing across the cell membrane.

5. A composition for inhibiting growth of a cancer cell, comprising:

a polypeptide consisting of the amino acid sequence HRDLKPSNLLLNTTCDLKICDFGLAR (SEQ ID NO: 1), or a variant form of said amino acid sequence having greater than 80% sequence identity with SEQ ID NO: 1 that binds to a binding domain of a β6 integrin subunit for extracellular signal-regulated kinase-2 (ERK2), or a fragment of said amino acid sequence having 10 to 25 amino acids of SEQ ID NO: 1 that binds to a binding domain of a β6 integrin subunit for ERK2; and a moiety coupled to the polypeptide for facilitating passage of the polypeptide across the outer membrane of the cell.

6. A pharmaceutical composition comprising a polypeptide consisting of the amino acid sequence HRDLKPSNLLLNTTCDLKICDFGLAR (SEQ ID NO: 1), or a variant form of said amino acid sequence having greater than 80% sequence identity with SEQ ID NO: 1 that binds to a binding domain of a β6 integrin subunit for extracellular signal-regulated kinase-2 (ERK2), or a fragment of said amino acid sequence having 10 to 25 amino acids of SEQ ID NO: 1 that binds to a binding domain of a β6 integrin subunit for ERK2, together with a pharmaceutically acceptable carrier.

7. A pharmaceutical composition comprising a fusion protein as defined in claim 2 together with a pharmaceutically acceptable carrier.

8. A pharmaceutical composition comprising an agent as defined in claim 5, together with a pharmaceutically acceptable carrier.

* * * * *

UNITED STATES PATENT AND TRADEMARK OFFICE

CERTIFICATE OF CORRECTION

PATENT NO. : 7,422,883 B2
APPLICATION NO. : 10/451291
DATED : September 9, 2008
INVENTOR(S) : Michael Valentine Agrez et al.

It is certified that error appears in the above-identified patent and that said Letters Patent is hereby corrected as shown below:

Column 2, line 67, "a chain" should read --α chain--;

Column 5, line 13, "Fynu" should read --Fyn--;

Column 6, line 17, "a chain" should read --α chain--;

Column 15, line 35, "(GAPDHu)" should read --(GAPDH)--;

Column 42, line 4, "mAb' SC-1647" should read --mAbSC-1647--;

Column 43, line 7, "CaC12," should read --Cac12,--;

Column 43, line 21, "phosphorylation)" should read --(phosphorylation)--;

Column 43, line 26, "5 mM" should read --50mM--;

Column 45, line 38, "10" should read --100μl--;

Column 83, claim 2, line 53, "seciuence" should read --sequence--; and

Column 84, claim 8, line 62, "comprising an agent as" should read --comprising composition as--.

Signed and Sealed this

Sixteenth Day of March, 2010

David J. Kappos
*Director of the United States Patent and Trademark Office*

SEQUENCE LISTING

<160> NUMBER OF SEQ ID NOS: 46

<210> SEQ ID NO 1
<211> LENGTH: 26
<212> TYPE: PRT
<213> ORGANISM: Artificial Sequence
<220> FEATURE:
<223> OTHER INFORMATION: ERK2 fragment

<400> SEQUENCE: 1

His Arg Asp Leu Lys Pro Ser Asn Leu Leu Leu Asn Thr Thr Cys Asp
1 5 10 15

Leu Lys Ile Cys Asp Phe Gly Leu Ala Arg
20 25

<210> SEQ ID NO 2
<211> LENGTH: 15
<212> TYPE: PRT
<213> ORGANISM: Artificial Sequence
<220> FEATURE:
<223> OTHER INFORMATION: ERK2 fragment

<400> SEQUENCE: 2

Pro Ser Asn Leu Leu Leu Asn Thr Thr Cys Asp Leu Lys Ile Cys
1 5 10 15

<210> SEQ ID NO 3
<211> LENGTH: 52
<212> TYPE: PRT
<213> ORGANISM: Artificial Sequence
<220> FEATURE:
<223> OTHER INFORMATION: Synthetic cytoplasmic domain of integrin beta 6

<400> SEQUENCE: 3

His Asp Arg Lys Glu Val Ala Lys Phe Glu Ala Glu Arg Ser Lys Ala
1 5 10 15

Lys Trp Gln Thr Gly Thr Asn Pro Leu Tyr Arg Gly Ser Thr Ser Thr
20 25 30

Phe Lys Asn Val Thr Tyr Lys His Arg Glu Lys Gln Lys Val Asp Leu
35 40 45

Ser Thr Asp Ser
50

<210> SEQ ID NO 4
<211> LENGTH: 41
<212> TYPE: PRT
<213> ORGANISM: Artificial Sequence
<220> FEATURE:
<223> OTHER INFORMATION: Cytoplasmic domain of integrin beta 1

-continued

<400> SEQUENCE: 4

His Asp Arg Arg Glu Phe Ala Lys Phe Glu Lys Glu Lys Met Asn Ala
1               5                   10                  15

Lys Trp Asp Thr Gly Glu Asn Pro Ile Tyr Lys Ser Ala Val Thr Thr
            20                  25                  30

Val Val Asn Pro Lys Tyr Glu Gly Lys
        35                  40

<210> SEQ ID NO 5
<211> LENGTH: 40
<212> TYPE: PRT
<213> ORGANISM: Artificial Sequence
<220> FEATURE:
<223> OTHER INFORMATION: Cytoplasmic domain of integrin beta 2

<400> SEQUENCE: 5

Ser Asp Leu Arg Glu Tyr Arg Arg Phe Glu Lys Glu Lys Leu Lys Ser
1               5                   10                  15

Gln Trp Asn Asn Asp Asn Pro Leu Phe Lys Ser Ala Thr Thr Thr Val
            20                  25                  30

Met Asn Pro Lys Phe Ala Glu Ser
        35                  40

<210> SEQ ID NO 6
<211> LENGTH: 41
<212> TYPE: PRT
<213> ORGANISM: Artificial Sequence
<220> FEATURE:
<223> OTHER INFORMATION: Cytoplasmic domain of integrin beta 3

<400> SEQUENCE: 6

His Asp Arg Lys Glu Phe Ala Lys Phe Glu Glu Glu Arg Ala Arg Ala
1               5                   10                  15

Lys Trp Asp Thr Ala Asn Asn Pro Leu Tyr Lys Glu Ala Thr Ser Thr
            20                  25                  30

Phe Thr Asn Ile Thr Tyr Arg Gly Thr
        35                  40

<210> SEQ ID NO 7
<211> LENGTH: 15
<212> TYPE: PRT
<213> ORGANISM: Artificial Sequence
<220> FEATURE:
<223> OTHER INFORMATION: Fragment of beta 6 cytoplamic domain

<400> SEQUENCE: 7

Arg Ser Lys Ala Lys Trp Gln Thr Gly Thr Asn Pro Leu Tyr Arg
1               5                   10                  15

<210> SEQ ID NO 8
<211> LENGTH: 10
<212> TYPE: PRT
<213> ORGANISM: Artificial Sequence
<220> FEATURE:
<223> OTHER INFORMATION: Synthetic peptide

<400> SEQUENCE: 8

Arg Ser Lys Ala Lys Asn Pro Leu Tyr Arg
1               5                   10

-continued

<210> SEQ ID NO 9
<211> LENGTH: 18
<212> TYPE: PRT
<213> ORGANISM: Artificial Sequence
<220> FEATURE:
<223> OTHER INFORMATION: ERK2 fragment

<400> SEQUENCE: 9

His Arg Asp Leu Lys Pro Ser Asn Leu Leu Leu Asn Thr Thr Cys Asp
1 5 10 15

Leu Lys

<210> SEQ ID NO 10
<211> LENGTH: 358
<212> TYPE: PRT
<213> ORGANISM: Artificial Sequence
<220> FEATURE:
<223> OTHER INFORMATION: MAP kinase ERK2 fragment

<400> SEQUENCE: 10

Met Ala Ala Ala Ala Ala Ala Gly Pro Glu Met Val Arg Gly Gln Val
1 5 10 15

Phe Asp Val Gly Pro Arg Tyr Thr Asn Leu Ser Tyr Ile Gly Glu Gly
20 25 30

Ala Tyr Gly Met Val Cys Ser Ala Tyr Asp Asn Leu Asn Lys Val Arg
35 40 45

Val Ala Ile Lys Lys Ile Ser Pro Phe Glu His Gln Thr Tyr Cys Gln
50 55 60

Arg Thr Leu Arg Glu Ile Lys Ile Leu Leu Arg Phe Arg His Glu Asn
65 70 75 80

Ile Ile Gly Ile Asn Asp Ile Ile Arg Ala Pro Thr Ile Glu Gln Met
85 90 95

Lys Asp Val Tyr Ile Val Gln Asp Leu Met Glu Thr Asp Leu Tyr Lys
100 105 110

Leu Leu Lys Thr Gln His Leu Ser Asn Asp His Ile Cys Tyr Phe Leu
115 120 125

Tyr Gln Ile Leu Arg Gly Leu Lys Tyr Ile His Ser Ala Asn Val Leu
130 135 140

His Arg Asp Leu Lys Pro Ser Asn Leu Leu Leu Asn Thr Thr Cys Asp
145 150 155 160

Leu Lys Ile Cys Asp Phe Gly Leu Ala Arg Val Ala Asp Pro Asp His
165 170 175

Asp His Thr Gly Phe Leu Thr Glu Tyr Val Ala Thr Arg Trp Tyr Arg
180 185 190

Ala Pro Glu Ile Met Leu Asn Ser Lys Gly Tyr Thr Lys Ser Ile Asp
195 200 205

Ile Trp Ser Val Gly Cys Ile Leu Ala Glu Met Leu Ser Asn Arg Pro
210 215 220

Ile Phe Pro Gly Lys His Tyr Leu Asp Gln Leu Asn His Ile Leu Gly
225 230 235 240

Ile Leu Gly Ser Pro Ser Gln Glu Asp Leu Asn Cys Ile Ile Asn Leu
245 250 255

Lys Ala Arg Asn Tyr Leu Leu Ser Leu Pro His Lys Asn Lys Val Pro
260 265 270

Trp Asn Arg Leu Phe Pro Asn Ala Asp Ser Lys Ala Leu Asp Leu Leu
275 280 285

-continued

```
Asp Lys Met Leu Thr Phe Asn Pro His Lys Arg Ile Glu Val Glu Gln
    290                 295                 300

Ala Leu Ala His Pro Tyr Leu Glu Gln Tyr Tyr Asp Pro Ser Asp Glu
305                 310                 315                 320

Pro Ile Ala Glu Ala Pro Phe Lys Phe Asp Met Glu Leu Asp Asp Leu
                325                 330                 335

Pro Lys Glu Lys Leu Lys Glu Leu Ile Phe Glu Glu Thr Ala Arg Phe
            340                 345                 350

Gln Pro Gly Tyr Arg Ser
        355
```

<210> SEQ ID NO 11
<211> LENGTH: 1074
<212> TYPE: DNA
<213> ORGANISM: Artificial Sequence
<220> FEATURE:
<223> OTHER INFORMATION: MAP kinase ERK2 fragment

<400> SEQUENCE: 11

```
atggcggcgg cggcggcggc gggcccggag atggtccgcg ggcaggtgtt cgacgtgggg     60

ccgcgctaca ctaatctctc gtacatcgga gaaggcgcct acggcatggt ttgttctgct    120

tatgataatc tcaacaaagt tcgagttgct atcaagaaaa tcagtccttt tgagcaccag    180

acctactgtc agagaaccct gagagagata aaaatcctac tgcgcttcag acatgagaac    240

atcatcggca tcaatgacat catccgggca ccaaccattg agcagatgaa agatgtatat    300

atagtacagg acctcatgga gacagatctt tacaagctct tgaagacaca gcacctcagc    360

aatgatcata tctgctattt tctttatcag atcctgagag gattaaagta tatacattca    420

gctaatgttc tgcaccgtga cctcaagcct tccaacctcc tgctgaacac cacttgtgat    480

ctcaagatct gtgactttgg ccttgcccgt gttgcagatc cagaccatga tcatacaggg    540

ttcttgacag agtatgtagc cacgcgttgg tacagagctc cagaaattat gttgaattcc    600

aagggttata ccaagtccat tgatatttgg tctgtgggct gcatcctggc agagatgcta    660

tccaacaggc ctatcttccc aggaaagcat taccttgacc agctgaatca catcctgggt    720

attcttggat ctccatcaca ggaagatctg aattgtataa taaatttaaa agctagaaac    780

tatttgcttt ctctcccgca caaaaataag gtgccgtgga acaggttgtt cccaaacgct    840

gactccaaag ctctggattt actggataaa atgttgacat ttaaccctca caagaggatt    900

gaagttgaac aggctctggc ccacccgtac ctggagcagt attatgaccc aagtgatgag    960

cccattgctg aagcaccatt caagtttgac atggagctgg acgacttacc taaggagaag   1020

ctcaaagaac tcatttttga agagactgct cgattccagc caggatacag atct         1074
```

<210> SEQ ID NO 12
<211> LENGTH: 788
<212> TYPE: PRT
<213> ORGANISM: Artificial Sequence
<220> FEATURE:
<223> OTHER INFORMATION: Integrin beta 6

<400> SEQUENCE: 12

```
Met Gly Ile Glu Leu Leu Cys Leu Phe Phe Leu Phe Leu Gly Arg Asn
1               5                   10                  15

Asp Ser Arg Thr Arg Trp Leu Cys Leu Gly Gly Ala Glu Thr Cys Glu
            20                  25                  30

Asp Cys Leu Leu Ile Gly Pro Gln Cys Ala Trp Cys Ala Gln Glu Asn
        35                  40                  45
```

-continued

```
Phe Thr His Pro Ser Gly Val Gly Glu Arg Cys Asp Thr Pro Ala Asn
    50                  55                  60

Leu Leu Ala Lys Gly Cys Gln Leu Asn Phe Ile Glu Asn Pro Val Ser
65                  70                  75                  80

Gln Val Glu Ile Leu Lys Asn Lys Pro Leu Ser Val Gly Arg Gln Lys
                85                  90                  95

Asn Ser Ser Asp Ile Val Gln Ile Ala Pro Gln Ser Leu Ile Leu Lys
            100                 105                 110

Leu Arg Pro Gly Gly Ala Gln Thr Leu Gln Val His Val Arg Gln Thr
        115                 120                 125

Glu Asp Tyr Pro Val Asp Leu Tyr Tyr Leu Met Asp Leu Ser Ala Ser
    130                 135                 140

Met Asp Asp Asp Leu Asn Thr Ile Lys Glu Leu Gly Ser Gly Leu Ser
145                 150                 155                 160

Lys Glu Met Ser Lys Leu Thr Ser Asn Phe Arg Leu Gly Phe Gly Ser
                165                 170                 175

Phe Val Glu Lys Pro Val Ser Pro Phe Val Lys Thr Thr Pro Glu Glu
            180                 185                 190

Ile Ala Asn Pro Cys Ser Ser Ile Pro Tyr Phe Cys Leu Pro Thr Phe
        195                 200                 205

Gly Phe Lys His Ile Leu Pro Leu Thr Asn Asp Ala Glu Arg Phe Asn
    210                 215                 220

Glu Ile Val Lys Asn Gln Lys Ile Ser Ala Asn Ile Asp Thr Pro Glu
225                 230                 235                 240

Gly Gly Phe Asp Ala Ile Met Gln Ala Ala Val Cys Lys Glu Lys Ile
                245                 250                 255

Gly Trp Arg Asn Asp Ser Leu His Leu Leu Val Phe Val Ser Asp Ala
            260                 265                 270

Asp Ser His Phe Gly Met Asp Ser Lys Leu Ala Gly Ile Val Ile Pro
        275                 280                 285

Asn Asp Gly Leu Cys His Leu Asp Ser Lys Asn Glu Tyr Ser Met Ser
    290                 295                 300

Thr Val Leu Glu Tyr Pro Thr Ile Gly Gln Leu Ile Asp Lys Leu Val
305                 310                 315                 320

Gln Asn Asn Val Leu Leu Ile Phe Ala Val Thr Gln Glu Gln Val His
                325                 330                 335

Leu Tyr Glu Asn Tyr Ala Lys Leu Ile Pro Gly Ala Thr Val Gly Leu
            340                 345                 350

Leu Gln Lys Asp Ser Gly Asn Ile Leu Gln Leu Ile Ile Ser Ala Tyr
        355                 360                 365

Glu Glu Leu Arg Ser Glu Val Glu Leu Glu Val Leu Gly Asp Thr Glu
    370                 375                 380

Gly Leu Asn Leu Ser Phe Thr Ala Ile Cys Asn Asn Gly Thr Leu Phe
385                 390                 395                 400

Gln His Gln Lys Lys Cys Ser His Met Lys Val Gly Asp Thr Ala Ser
                405                 410                 415

Phe Ser Val Thr Val Asn Ile Pro His Cys Glu Arg Arg Ser Arg His
            420                 425                 430

Ile Ile Ile Lys Pro Val Gly Leu Gly Asp Ala Leu Glu Leu Leu Val
        435                 440                 445

Ser Pro Glu Cys Asn Cys Asp Cys Gln Lys Glu Val Glu Val Asn Ser
    450                 455                 460
```

-continued

```
Ser Lys Cys His His Gly Asn Gly Ser Phe Gln Cys Gly Val Cys Ala
465                 470                 475                 480

Cys His Pro Gly His Met Gly Pro Arg Cys Glu Cys Gly Glu Asp Met
                485                 490                 495

Leu Ser Thr Asp Ser Cys Lys Glu Ala Pro Asp His Pro Ser Cys Ser
            500                 505                 510

Gly Arg Gly Asp Cys Tyr Cys Gly Gln Cys Ile Cys His Leu Ser Pro
        515                 520                 525

Tyr Gly Asn Ile Tyr Gly Pro Tyr Cys Gln Cys Asp Asn Phe Ser Cys
    530                 535                 540

Val Arg His Lys Gly Leu Leu Cys Gly Gly Asn Gly Asp Cys Asp Cys
545                 550                 555                 560

Gly Glu Cys Val Cys Arg Ser Gly Trp Thr Gly Glu Tyr Cys Asn Cys
                565                 570                 575

Thr Thr Ser Thr Asp Ser Cys Val Ser Glu Asp Gly Val Leu Cys Ser
            580                 585                 590

Gly Arg Gly Asp Cys Val Cys Gly Lys Cys Val Cys Thr Asn Pro Gly
        595                 600                 605

Ala Ser Gly Pro Thr Cys Glu Arg Cys Pro Thr Cys Gly Asp Pro Cys
    610                 615                 620

Asn Ser Lys Arg Ser Cys Ile Glu Cys His Leu Ser Ala Ala Gly Gln
625                 630                 635                 640

Ala Gly Glu Glu Cys Val Asp Lys Cys Lys Leu Ala Gly Ala Thr Ile
                645                 650                 655

Ser Glu Glu Glu Asp Phe Ser Lys Asp Gly Ser Val Ser Cys Ser Leu
            660                 665                 670

Gln Gly Glu Asn Glu Cys Leu Ile Thr Phe Leu Ile Thr Thr Asp Asn
        675                 680                 685

Glu Gly Lys Thr Ile Ile His Ser Ile Asn Glu Lys Asp Cys Pro Lys
    690                 695                 700

Pro Pro Asn Ile Pro Met Ile Met Leu Gly Val Ser Leu Ala Thr Leu
705                 710                 715                 720

Leu Ile Gly Val Val Leu Leu Cys Ile Trp Lys Leu Leu Val Ser Phe
                725                 730                 735

His Asp Arg Lys Glu Val Ala Lys Phe Glu Ala Glu Arg Ser Lys Ala
            740                 745                 750

Lys Trp Gln Thr Gly Thr Asn Pro Leu Tyr Arg Gly Ser Thr Ser Thr
        755                 760                 765

Phe Lys Asn Val Thr Tyr Lys His Arg Glu Lys Gln Lys Val Asp Leu
    770                 775                 780

Ser Thr Asp Cys
785


<210> SEQ ID NO 13
<211> LENGTH: 5
<212> TYPE: PRT
<213> ORGANISM: Artificial Sequence
<220> FEATURE:
<223> OTHER INFORMATION: Fragment of beta 6 cytoplamic domain

<400> SEQUENCE: 13

Arg Ser Lys Ala Lys
1               5
```

-continued

<210> SEQ ID NO 14
<211> LENGTH: 5
<212> TYPE: PRT
<213> ORGANISM: Artificial Sequence
<220> FEATURE:
<223> OTHER INFORMATION: Fragment of beta 6 cytoplamic domain

<400> SEQUENCE: 14

Asn Pro Leu Tyr Arg
1 5

<210> SEQ ID NO 15
<211> LENGTH: 20
<212> TYPE: DNA
<213> ORGANISM: Artificial Sequence
<220> FEATURE:
<223> OTHER INFORMATION: Forward primer for beta 6

<400> SEQUENCE: 15
aggatagttc tgtttcctgc 20

<210> SEQ ID NO 16
<211> LENGTH: 20
<212> TYPE: DNA
<213> ORGANISM: Artificial Sequence
<220> FEATURE:
<223> OTHER INFORMATION: Reverse primer for beta 6

<400> SEQUENCE: 16
atcataggaa tatttggagg 20

<210> SEQ ID NO 17
<211> LENGTH: 22
<212> TYPE: PRT
<213> ORGANISM: Artificial Sequence
<220> FEATURE:
<223> OTHER INFORMATION: Fragment of beta 6 cytoplasmic domain

<400> SEQUENCE: 17

His Asp Arg Lys Glu Val Ala Lys Phe Glu Ala Glu Arg Ser Lys Ala
1 5 10 15

Lys Trp Gln Thr Gly Thr
20

<210> SEQ ID NO 18
<211> LENGTH: 20
<212> TYPE: PRT
<213> ORGANISM: Artificial Sequence
<220> FEATURE:
<223> OTHER INFORMATION: Fragment of beta 6 cytoplasmic domain

<400> SEQUENCE: 18

Arg Ser Lys Ala Lys Trp Gln Thr Gly Thr Asn Pro Leu Tyr Arg Gly
1 5 10 15

Ser Thr Ser Thr
20

<210> SEQ ID NO 19
<211> LENGTH: 20
<212> TYPE: PRT
<213> ORGANISM: Artificial Sequence
<220> FEATURE:
<223> OTHER INFORMATION: Fragment of beta 6 cytoplasmic domain -continued

<400> SEQUENCE: 19

```
Asn Pro Leu Tyr Arg Gly Ser Thr Ser Thr Phe Lys Asn Val Thr Tyr
1               5                   10                  15

Lys His Arg Glu
            20
```

<210> SEQ ID NO 20
<211> LENGTH: 20
<212> TYPE: PRT
<213> ORGANISM: Artificial Sequence
<220> FEATURE:
<223> OTHER INFORMATION: Fragment of beta 6 cytoplasmic domain

<400> SEQUENCE: 20

```
Phe Lys Asn Val Thr Tyr Lys His Arg Glu Lys Gln Lys Val Asp Leu
1               5                   10                  15

Ser Thr Asp Ser
            20
```

<210> SEQ ID NO 21
<211> LENGTH: 10
<212> TYPE: PRT
<213> ORGANISM: Artificial Sequence
<220> FEATURE:
<223> OTHER INFORMATION: Fragment of beta 6 cytoplasmic domain

<400> SEQUENCE: 21

```
Arg Ser Lys Ala Lys Trp Gln Thr Gly Thr
1               5                   10
```

<210> SEQ ID NO 22
<211> LENGTH: 10
<212> TYPE: PRT
<213> ORGANISM: Artificial Sequence
<220> FEATURE:
<223> OTHER INFORMATION: Fragment of beta 6 cytoplasmic domain

<400> SEQUENCE: 22

```
Asn Pro Leu Tyr Arg Gly Ser Thr Ser Thr
1               5                   10
```

<210> SEQ ID NO 23
<211> LENGTH: 10
<212> TYPE: PRT
<213> ORGANISM: Artificial Sequence
<220> FEATURE:
<223> OTHER INFORMATION: Fragment of beta 6 cytoplasmic domain

<400> SEQUENCE: 23

```
Trp Gln Thr Gly Thr Asn Pro Leu Tyr Arg
1               5                   10
```

<210> SEQ ID NO 24
<211> LENGTH: 10
<212> TYPE: PRT
<213> ORGANISM: Artificial Sequence
<220> FEATURE:
<223> OTHER INFORMATION: Fragment of beta 6 cytoplasmic domain

<400> SEQUENCE: 24

```
Lys Phe Glu Ala Glu Arg Ser Lys Ala Lys
1               5                   10
```

-continued

<210> SEQ ID NO 25
<211> LENGTH: 52
<212> TYPE: PRT
<213> ORGANISM: Artificial Sequence
<220> FEATURE:
<223> OTHER INFORMATION: Cytoplasmic domain of integrin beta 6

<400> SEQUENCE: 25

```
His Asp Arg Lys Glu Val Ala Lys Phe Glu Ala Glu Arg Ser Lys Ala
1               5                   10                  15

Lys Trp Gln Thr Gly Thr Asn Pro Leu Tyr Arg Gly Ser Thr Ser Thr
            20                  25                  30

Phe Lys Asn Val Thr Tyr Lys His Arg Glu Lys Gln Lys Val Asp Leu
        35                  40                  45

Ser Thr Asp Cys
    50
```

<210> SEQ ID NO 26
<211> LENGTH: 19
<212> TYPE: PRT
<213> ORGANISM: Artificial Sequence
<220> FEATURE:
<223> OTHER INFORMATION: Fragment of beta 6 cytoplasmic domain

<400> SEQUENCE: 26

```
Glu Ala Glu Arg Ser Lys Ala Lys Trp Gln Thr Gly Thr Asn Pro Leu
1               5                   10                  15

Tyr Arg Gly
```

<210> SEQ ID NO 27
<211> LENGTH: 20
<212> TYPE: PRT
<213> ORGANISM: Artificial Sequence
<220> FEATURE:
<223> OTHER INFORMATION: Fragment of beta 1 cytoplasmic domain

<400> SEQUENCE: 27

```
Lys Phe Glu Lys Glu Lys Met Asn Ala Lys Trp Asp Thr Gly Glu Asn
1               5                   10                  15

Pro Ile Tyr Lys
            20
```

<210> SEQ ID NO 28
<211> LENGTH: 16
<212> TYPE: PRT
<213> ORGANISM: Artificial Sequence
<220> FEATURE:
<223> OTHER INFORMATION: Fragment of beta 2 cytoplasmic domain

<400> SEQUENCE: 28

```
Lys Glu Lys Leu Lys Ser Gln Trp Asn Asn Asp Asn Pro Leu Phe Lys
1               5                   10                  15
```

<210> SEQ ID NO 29
<211> LENGTH: 15
<212> TYPE: PRT
<213> ORGANISM: Artificial Sequence
<220> FEATURE:
<223> OTHER INFORMATION: Fragment of beta 3 cytoplasmic domain

<400> SEQUENCE: 29

```
Arg Ala Arg Ala Lys Trp Asp Thr Ala Asn Asn Pro Leu Tyr Lys
1               5                   10                  15
```

-continued

<210> SEQ ID NO 30
<211> LENGTH: 15
<212> TYPE: PRT
<213> ORGANISM: Artificial Sequence
<220> FEATURE:
<223> OTHER INFORMATION: Fragment of beta 5 cytoplasmic domain

<400> SEQUENCE: 30

```
Arg Ser Arg Ala Arg Tyr Glu Met Ala Ser Asn Pro Leu Tyr Arg
1               5                   10                  15
```

<210> SEQ ID NO 31
<211> LENGTH: 30
<212> TYPE: PRT
<213> ORGANISM: Artificial Sequence
<220> FEATURE:
<223> OTHER INFORMATION: ERK2 fragment

<400> SEQUENCE: 31

```
Met Ala Ala Ala Ala Ala Ala Gly Ala Gly Pro Glu Met Val Arg Gly
1               5                   10                  15

Gln Val Phe Asp Val Gly Pro Arg Tyr Thr Asn Leu Ser Tyr
            20                  25                  30
```

<210> SEQ ID NO 32
<211> LENGTH: 30
<212> TYPE: PRT
<213> ORGANISM: Artificial Sequence
<220> FEATURE:
<223> OTHER INFORMATION: ERK2 fragment

<400> SEQUENCE: 32

```
Tyr Thr Asn Leu Ser Tyr Ile Gly Glu Gly Ala Tyr Gly Met Val Cys
1               5                   10                  15

Ser Ala Tyr Asp Asn Val Asn Lys Val Arg Val Ala Ile Lys
            20                  25                  30
```

<210> SEQ ID NO 33
<211> LENGTH: 30
<212> TYPE: PRT
<213> ORGANISM: Artificial Sequence
<220> FEATURE:
<223> OTHER INFORMATION: ERK2 fragment

<400> SEQUENCE: 33

```
Val Arg Val Ala Ile Lys Lys Ile Ser Pro Phe Glu His Gln Thr Tyr
1               5                   10                  15

Cys Gln Arg Thr Leu Arg Glu Ile Lys Ile Leu Leu Arg Phe
            20                  25                  30
```

<210> SEQ ID NO 34
<211> LENGTH: 30
<212> TYPE: PRT
<213> ORGANISM: Artificial Sequence
<220> FEATURE:
<223> OTHER INFORMATION: ERK2 fragment

<400> SEQUENCE: 34

```
Lys Ile Leu Leu Arg Phe Arg His Glu Asn Ile Ile Gly Ile Asn Asp
1               5                   10                  15

Ile Ile Arg Ala Pro Thr Ile Glu Gln Met Lys Asp Val Tyr
            20                  25                  30
```

-continued

<210> SEQ ID NO 35
<211> LENGTH: 30
<212> TYPE: PRT
<213> ORGANISM: Artificial Sequence
<220> FEATURE:
<223> OTHER INFORMATION: ERK2 fragment

<400> SEQUENCE: 35

Gln Met Lys Asp Val Tyr Ile Val Gln Asp Leu Met Glu Thr Asp Leu
1 5 10 15

Tyr Lys Leu Leu Lys Thr Gln His Leu Ser Asn Asp His Ile
20 25 30

<210> SEQ ID NO 36
<211> LENGTH: 31
<212> TYPE: PRT
<213> ORGANISM: Artificial Sequence
<220> FEATURE:
<223> OTHER INFORMATION: ERK2 fragment

<400> SEQUENCE: 36

Leu Ser Asn Asp His Ile Cys Tyr Phe Leu Tyr Gln Ile Leu Arg Gly
1 5 10 15

Leu Lys Tyr Ile His Ser Ala Asn Val Leu His Arg Asp Leu Lys
20 25 30

<210> SEQ ID NO 37
<211> LENGTH: 39
<212> TYPE: PRT
<213> ORGANISM: Artificial Sequence
<220> FEATURE:
<223> OTHER INFORMATION: ERK2 fragment

<400> SEQUENCE: 37

Asp Phe Gly Leu Ala Arg Val Ala Asp Pro Asp His Asp His Thr Gly
1 5 10 15

Phe Leu Thr Glu Tyr Val Ala Thr Arg Trp Tyr Arg Ala Pro Glu Ile
20 25 30

Met Leu Asn Ser Lys Gly Tyr
35

<210> SEQ ID NO 38
<211> LENGTH: 30
<212> TYPE: PRT
<213> ORGANISM: Artificial Sequence
<220> FEATURE:
<223> OTHER INFORMATION: ERK2 fragment

<400> SEQUENCE: 38

Asn Ser Lys Gly Tyr Thr Lys Ser Ile Asp Ile Trp Ser Val Gly Cys
1 5 10 15

Ile Leu Ala Glu Met Leu Ser Asn Arg Pro Ile Phe Pro Gly
20 25 30

<210> SEQ ID NO 39
<211> LENGTH: 30
<212> TYPE: PRT
<213> ORGANISM: Artificial Sequence
<220> FEATURE:
<223> OTHER INFORMATION: ERK2 fragment -continued

<400> SEQUENCE: 39

```
Pro Ile Phe Pro Gly Lys His Tyr Leu Asp Gln Leu Asn His Ile Leu
1               5                   10                  15

Gly Ile Leu Gly Ser Pro Ser Gln Glu Asp Leu Asn Cys Ile
            20                  25                  30
```

<210> SEQ ID NO 40
<211> LENGTH: 30
<212> TYPE: PRT
<213> ORGANISM: Artificial Sequence
<220> FEATURE:
<223> OTHER INFORMATION: ERK2 fragment

<400> SEQUENCE: 40

```
Asp Leu Asn Cys Ile Ile Asn Leu Lys Ala Arg Asn Tyr Leu Leu Ser
1               5                   10                  15

Leu Pro His Lys Asn Lys Val Pro Trp Asn Arg Leu Phe Pro
            20                  25                  30
```

<210> SEQ ID NO 41
<211> LENGTH: 30
<212> TYPE: PRT
<213> ORGANISM: Artificial Sequence
<220> FEATURE:
<223> OTHER INFORMATION: ERK2 fragment

<400> SEQUENCE: 41

```
Asn Arg Leu Phe Pro Asn Ala Asp Ser Lys Ala Leu Asp Leu Leu Asp
1               5                   10                  15

Lys Met Leu Thr Phe Asn Pro His Lys Arg Ile Glu Val Glu
            20                  25                  30
```

<210> SEQ ID NO 42
<211> LENGTH: 30
<212> TYPE: PRT
<213> ORGANISM: Artificial Sequence
<220> FEATURE:
<223> OTHER INFORMATION: ERK2 fragment

<400> SEQUENCE: 42

```
Arg Ile Glu Val Glu Gln Ala Leu Ala His Pro Tyr Leu Glu Gln Tyr
1               5                   10                  15

Tyr Asp Pro Ser Asp Glu Pro Ile Ala Glu Ala Pro Phe Lys
            20                  25                  30
```

<210> SEQ ID NO 43
<211> LENGTH: 35
<212> TYPE: PRT
<213> ORGANISM: Artificial Sequence
<220> FEATURE:
<223> OTHER INFORMATION: ERK2 fragment

<400> SEQUENCE: 43

```
Glu Ala Pro Phe Lys Phe Asp Met Glu Leu Asp Asp Leu Pro Lys Glu
1               5                   10                  15

Lys Leu Lys Glu Leu Ile Phe Glu Glu Thr Ala Arg Phe Gln Pro Gly
            20                  25                  30

Tyr Arg Ser
        35
```

-continued

```
<210> SEQ ID NO 44
<211> LENGTH: 15
<212> TYPE: PRT
<213> ORGANISM: Artificial Sequence
<220> FEATURE:
<223> OTHER INFORMATION: ERK2 fragment

<400> SEQUENCE: 44

Asp Pro Asp His Asp His Thr Gly Phe Leu Thr Glu Tyr Val Ala
1               5                   10                  15


<210> SEQ ID NO 45
<211> LENGTH: 15
<212> TYPE: PRT
<213> ORGANISM: Artificial Sequence
<220> FEATURE:
<223> OTHER INFORMATION: ERK2 fragment

<400> SEQUENCE: 45

Pro Ser Asn Leu Leu Leu Asn Thr Thr Cys Asp Leu Lys Ile Cys
1               5                   10                  15


<210> SEQ ID NO 46
<211> LENGTH: 12
<212> TYPE: PRT
<213> ORGANISM: Artificial Sequence
<220> FEATURE:
<223> OTHER INFORMATION: Ligand recognition motif for alpha V beta 6
      integrin

<400> SEQUENCE: 46

Arg Thr Asp Leu Asp Ser Leu Arg Thr Tyr Thr Leu
1               5                   10
```